(12) United States Patent
Wang et al.

(10) Patent No.: US 8,735,622 B2
(45) Date of Patent: May 27, 2014

(54) HISTONE DEMETHYLASE INHIBITORS AND METHODS FOR USING THE SAME

(71) Applicants: Xiang Wang, Superior, CO (US); Wenqing Xu, Boulder, CO (US)

(72) Inventors: Xiang Wang, Superior, CO (US); Wenqing Xu, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 13/691,507

(22) Filed: Nov. 30, 2012

(65) Prior Publication Data
US 2013/0137720 A1     May 30, 2013

Related U.S. Application Data

(60) Provisional application No. 61/565,456, filed on Nov. 30, 2011.

(51) Int. Cl.
*C07C 271/00* (2006.01)

(52) U.S. Cl.
USPC .......................................................... 560/27

(58) Field of Classification Search
USPC .......................................................... 560/27
See application file for complete search history.

(56) References Cited

PUBLICATIONS

Luo et al., A Selective Inhibitor and Probe of the Cellular Functions of Jumonji C Domain-Containing Histone Demethylases, J. Am. Chem. Soc. May 17, 2011, 133, 9451-9456.*
WHO, Pharmaceutical excipients—an overview including considerations fpr paediatric dosing, Beijing, Jun. 21 to 25, 2010.*
Drugs.com, Pregelatinized Starch.*
Rose et al., Selective Inhibitors of the JMJD2 Histone Demethylases: Combined Nondenaturing Mass Spectrometric Screening and Crystallographic Approaches, J. Med. Chem. 2010, 53, pp. 1810-1818.*
Testa Prodrug research: futile or fertile? Biochemical Pharmacology 68 (2004) 2097-2106).*
Ettmayer et al., Lessons Learned from Marketed and investigational Prodrugs, Journal of Medicinal Chemistry, 47, 2004, pp. 2393-2404.*
Wermuth (Similarity in drugs: reflections on analogue design, Drug Discovery Today, Apr. 11, 2006, pp. 348-354.*
Tsukada, Hydroxylation mediates chromatin demethylation, Journal of Biochemistry Advance Access published Jan. 13, 2012, pp. 1-51.*
Klose et al., "Regulation of histone methylation by demethylimination and demethylation," Nat. Rev. Mol. Cell Biol., 2007, 8, 307-318.
Luco et al., "Regulation of Alternative Splicing by Histone Modifications," Science, 2010, 327, 996-1000.
Tong et al., "Chromatin deacetylation by an ATP-dependent nucleosome remodelling complex," Nature, 1998, 395, 917-921.
Shi et al., "Histone Demethylation Mediated by the Nuclear Amine Oxidase Homolog LSD1," Cell 2004, 119, 941-953.
Lan et al., "Mechanisms involved in the regulation of histone lysine demethylases," Curr. Opin. Cell. Biol., 2008, 20, 316-325.
Wissmann et al., "Cooperative demethylation by JMJD2C and LSD1 promotes androgen receptor-dependent gene expression," Nat. Cell Biol. 2007, 9, 347-353.
Ciccone et al., "KDM1B is a histone H3K4 demethylase required to establish maternal genomic imprints." Nature, 2009, 461, pp. 415-418.
Cole, "Chemical Probes for Histone-Modifying Enzymes," Nat. Chem. Biol. 2008, 4, 590-597.
Culhane et al., "A Mechanism-Based Inactivator for Histone Demethylase LSD1," J. Am. Chem. Soc., 2006, 128, 4536-4537.
Ueda et al., "Identification of Cell-Active Lysine Specific Demethylase 1-Selective Inhibitors," J. Am. Chem. Soc., 2009, 131, 17536-17537.
Huang et al., "Inhibition of lysine-specific demethylase 1 by polyamine analogues results in reexpression of aberrantly silenced genes," Proc. Natl. Acad. Sci. U.S.A., 2007, 104, 8023-8028.
Cloos et al., "The putative oncogene GASC1 demethylates tri- and dimethylated lysine 9 on histone H3," Nature, 2006, 442, 307-311.
Rose et al., "Inhibitor Scaffolds for 2-Oxoglutarate-Dependent Histone Lysine Demethylases," J. Med. Chem., 2008, 51, 7053-7056.
Hamada et al., "Synthesis and activity of N-oxalylglycine and its derivatives as Jumonji C-domain-containing histone lysine demethylase inhibitors," Bioorg. Med. Chem. Lett. 2009, 19, 2852-2855.
Rose et al., "Selective Inhibitors of the JMJD2 Histone Demethylases: Combined Nondenaturing Mass Spectrometric Screening and Crystallographic Approaches," J. Med. Chem., 2010, 53, 1810-1818.
Chen et al., "Structural Insights into Histone Demethylation by JMJD2 FamilyMembers," Cell, 2006, vol. 125, pp. 691-702.
NG et al., "Crystal structures of histone demethylase JMJD2A reveal basis for substrate specificity," Nature, 2007, 448, 87-91.
Asikainen et al., "Activation of hypoxia-inducible factors in hyperoxia through prolyl 4-hydroxylase blockade in cells and explants of primate lung," Proc. Natl. Acad. Sci. U.S.A. 2005, vol. 102, pp. 10212-10217.
Ivan et al., "HIFa Targeted for VHL-Mediated Destruction by Proline Hydroxylation: Implications for O2 Sensing," Science 2001, 292, 464-468.

* cited by examiner

*Primary Examiner* — Wu-Cheng Winston Shen
*Assistant Examiner* — Blaine G Doletski
(74) *Attorney, Agent, or Firm* — Don D. Cha; Hamilton DeSanctis & Cha, LLP

(57) ABSTRACT

The present invention provides compounds, or derivatives or prodrugs thereof, that comprise a methyllysine mimic, and an α-ketoglutarate mimic that are attached through a linker and methods for using and producing the same. In some embodiments, compounds of the invention are of the formula: M-L-K, or a derivative or a prodrug thereof, wherein M is a methyllysine mimic, L is a linker, and K is an α-ketoglutarate mimic.

16 Claims, 12 Drawing Sheets

HISTONE DEMETHYLASE INHIBITORS AND METHODS FOR USING THE SAME

CROSS-REFERENCE TO RELATED APPLICATIONS

This application claims the priority benefit of U.S. Provisional Application No. 61/565,456, filed Nov. 30, 2011, which is incorporated herein by reference in its entirety.

FIELD OF THE INVENTION

The present invention relates to histone demethylase inhibitors and methods for using the same.

BACKGROUND OF THE INVENTION

The covalent attachment of functional groups to chromatin, including DNA methylation and histone modifications, are associated with heritable changes that regulate cellular transcriptomes without altering DNA sequence. Histone methylation is one of the most important chromatin marks; these play important roles in transcriptional regulation, DNA-damage response, heterochromatin formation and maintenance, and X-chromosome inactivation. A recent discovery also revealed that histone methylation affects the splicing outcome of pre-mRNA by influencing the recruitment of splicing regulators. Histone methylation includes mono-, di-, and tri-methylation of lysines, and mono-, symmetric di-, and asymmetric di-methylation of arginines. These modifications can be either an activating or repressing mark, depending on the site and degree of methylation. Without being bound by any theory, two classes of enzymes are believed to regulate the maintenance of histone methylation: histone methyltransferases (HMTs) and histone demethylases (HDMs). HDMs are the most recent family of histone-modifying enzymes discovered. Since the human HDM, LSD1, was first detected in 1998 and characterized in 2004, over a dozen HDMs have been discovered that modify histone H3 lysine 4 (H3K4), H3K9, H3K27, H3K36, H3R2, or H4R3 methylations. However, HDMs that specifically modify H3K79 and H4K20 methylation have not yet been identified. Recent studies have shown HDMs often display tissue-specific expression and play critical roles in gene expression, meiosis, and embryonic stem cell self-renewal.

HDMs can be categorized into two classes based on their enzymatic mechanisms: flavin adenine dinucleotide (FAD)-dependent HDMs and Jumonji C domain-containing HDMs (JHDMs). There are two FAD-dependent HDMs, both of which are monoamine oxidases and can demethylate mono- and di-methylated H3K4 and H3K9. Compared with FAD-dependent HDMs, JHDMs are much more versatile in terms of their substrate scope. They can modify not only lysine and arginine residues at many different positions (e.g., H3R2, H3K4, H3K9, H3K27, and H3K36) on histone proteins, but also lysine and arginine at all methylation states. JHDMs are iron(II)- and α-ketoglutarate-dependent hydroxylases, which use molecular oxygen and α-ketoglutarate to generate the reactive iron(IV)-oxo species, which may in turn hydroxylate the methyl groups of N-methyl lysine residues. It is believed that the resulting hemiaminals collapse under physiological conditions to give the demethylated lysine and formaldehyde as a byproduct.

Small-molecule modulators of histone-modifying enzymes not only play important roles in understanding the structures and functions of these enzymes, but also provide unique opportunities for treating diseases such as cancer. Small molecules specifically inhibiting FAD-dependent HDMs have been discovered recently. A modified histone H3 peptide containing propargyl amine functionality was shown to be a specific inhibitor of LSD1 in vitro, and cyclopropylamine-containing lysine analogs were reported as cell-active specific inhibitors of LSD1. In addition, polyamine analogues have also been reported to inhibit LSD1 in cells, which resulted in re-expression of aberrantly silenced genes. As with other iron(II)- and α-ketoglutarate-dependent hydroxylases, JHDMs are inhibited by nickel(II), desferoxamine (DFO, an iron chelating agent), and α-ketoglutarate mimics such as N-oxalylglycine (NOG) and pyridine 2,5-dicarboxylate in vitro. The dimethyl ester of NOG (DMOG) has been proven to inhibit HDMs in vivo. Very recently, small-molecule inhibitors that show in vitro specificity for JMJD2 HDMs have been reported. Unfortunately, cell-active specific inhibitors of JHDMs have not been reported.

Since cell-active specific inhibitors of JHDMs can be used in a variety of therapeutic uses, there is a need for cell-active specific inhibitors of JHDMs.

SUMMARY OF THE INVENTION

Some aspects of the invention provide compounds comprising a methyllysine mimic and an α-ketoglutarate mimic that are attached to one another by a linker. Such compounds inhibit histone demethylases and can be used to treat a clinical condition associated with the activity and/or overexpression of Jumonji C Domain-Containing Histone Demethylase. In some embodiments, compounds of the invention are cell-active specific inhibitors of JHDMs.

Other aspects of the invention provide methods for using such a compound of the invention or a composition comprising a compound of the invention.

Still other aspects of the invention provide a pharmaceutical composition comprising a compound of the invention and a pharmaceutically acceptable excipients.

In one particular aspect, a compound of the invention is of the formula: M-L-K, or a derivative or a prodrug thereof, wherein M is a methyllysine mimic, L is a linker, and K is an α-ketoglutarate mimic. In some embodiments, the linker comprises from 2 to 12 chain atoms each of which is independently selected from the group consisting of C, O, and S, provided that no two heteroatoms are linked to one another. In other embodiments, the linker comprises $C_2$-$C_{12}$ carbon chain atoms. Typically, the linker is a $C_2$-$C_{12}$ alkylene, $C_2$-$C_{12}$ alkenylene, or $C_2$-$C_{12}$ alkynylene. Often the linker is a $C_2$-$C_{12}$ alkylene.

Still in other embodiments, the methyllysine mimic, M, is of the formula:

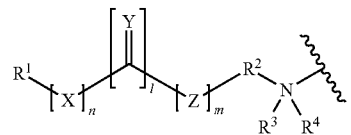

where
each of l, m and n is independently 0 or 1;
each of X and Z is independently O, S, or $NR^5$;
Y is O, S or $NR^5$;
$R^1$ is aryl, aralkyl, heteroaryl or fluorescein;
$R^2$ is alkylene or a moiety of the formula —$R^6$—$Ar^1$—$R^7$—, wherein each of $R^6$ and $R^7$ is independently alkylene, and $Ar^1$ is arylene;

R³ is hydrogen, alkyl, aralkyl, heteroalkyl, heteroaralkyl;
R⁴ is hydrogen, alkyl, or absent; and
each of R⁵ is independently hydrogen or alkyl.

In some embodiments, R¹ is phenyl, naphthyl, benzyl, naphthylalkyl, quinolinyl, or fluorescein, each of which is optionally substituted.

Yet in other embodiments, X is NH.
Still in other embodiments, Y is O.
In other embodiments, Z is O.
Yet still in other embodiments, R² is $C_3$-$C_8$ alkylene.
In some embodiments, R⁶ and R⁷ are methylene.
Still in other embodiments, Ar¹ is phenylene.
Yet in other embodiments, R³ is H or methyl.
In yet other embodiments, R⁴ is alkyl or absent.
In some embodiments, the α-ketoglutarate mimic, K, is of the formula:

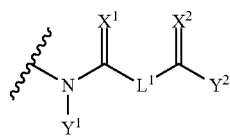

where
Y¹ is OR⁸, or —NHR⁸;
each of X¹ and X² is independently O, S, or NR⁹;
Y² is —OR⁸, —SR¹⁰, or —NR¹¹R¹²;
each of R⁸ is independently hydrogen, alkyl, or a hydroxyl protecting group;
each of R⁹ is independently hydrogen, alkyl, or a nitrogen protecting group;
R¹⁰ is hydrogen, alkyl, or a sulfur protecting group;
R¹¹ is hydrogen or alkyl;
R¹² is hydrogen, alkyl, or a nitrogen protecting group; and
L¹ is alkylene, alkenylene, arene, or alkynylene.

Within these embodiments, in some instances R⁸ is hydrogen or $C_1$-$C_4$ alkyl.

In other instances, X¹ and X² are O.
Still in other instances, Y² is —OR⁸.
Yet in other instances, L¹ is $C_2$-$C_6$ alkylene or $C_2$-$C_6$ alkenylene.

Other aspects of the invention provide a method for treating a clinic condition associated with activity of Jumonji C Domain-Containing Histone Demethylase comprising administering to the subject in need of such a treatment a therapeutically effective amount of a compound of the invention. Typical clinical conditions that can be treated by compounds of the invention include, but are not limited to, cancer or mental retardation. Exemplary cancers that can be treated with compounds of the invention include, but are not limited to, prostate cancer, testis cancer, esophageal squamous carcinoma, and breast cancer.

Another aspect of the invention provides a method for treating a clinic condition associated with overexpression of Jumonji C Domain-Containing Histone Demethylase comprising administering to the subject in need of such a treatment a therapeutically effective amount of a compound of the invention described herein.

In some embodiments of the invention, the compounds of the invention include all or some of the compounds shown in FIGS. 9, 11 and 12, as well as those compounds disclosed in Table 1 and in the Examples section.

In other embodiments, compounds of the invention include particular substituents (e.g., R¹, R², R³, R⁴, etc.) that correspond to corresponding substituents shown in compounds of FIGS. 9, 11, and 12 as well as those in Table 1 and those disclosed in the Examples section.

BRIEF DESCRIPTION OF THE DRAWINGS

FIG. 2A is a bar graph data showing methylstat, but not compound 1, inhibits KYSE150 cell growth after treatment for 48 hours. Data represent mean values of measurements±s.d. FIG. 2B is fluorescence images showing methylstat recovered H3K9me3 level in HeLa cells ectopically expressing GASC1(1-420)-GFP fusion protein. HeLa cells were transfected with GASC1(1-420)-GFP and then treated with DMSO or 10 µM methylstat. Immunostaining experiments using anti-H3K9me3 antibody were performed after 48 hours of incubation. Yellow arrowheads indicate transfected cells. FIG. 2C is electrophoretic slides showing methylstat induced hypermethylations of histone proteins in a concentration-dependent manner. KYSE150 cells were treated with DMSO, DFO at 150 µM, DMOG at 1 mM, and methylstat at 5, 10, and 15 µM for 48 hours, respectively. FIG. 2D is a bar graph showing $EC_{50}$ values of methylstat for H3K4me3 and H3K9me3 in KYSE150 cells as 10.3 µM and 8.6 µM, respectively. The $EC_{50}$ value were determined by quantifying images from immunostaining assays. Data represent mean values of measurements±s.d. FIG. 2E is electrophoretic data showing methylstat did not significantly inhibit prolyl hydroxylases. MCF7 cells were treated with DMSO, DFO at 150 µM, DMOG at 1 and 2 mM, methylstat at 5, 10, and 15 µM for 24 hours, respectively.

FIG. 3A is mass spectrum of H3K9me3 peptide. FIG. 3B is mass spectrum of H3K9me3 peptide treated with purified GST-fused GASC1(1-420) for 2 hours. FIG. 3C is mass spectrum of H3K9me3 peptide treated with purified GST-fused GASC1(1-420) in the presence of 1 µM of compound 1 for 2 hours. FIG. 3D is mass spectrum of H3K9me3 peptide treated with purified GST-fused GASC1(1-420) in the presence of 5 µM of compound 1 for 2 hours.

DETAILED DESCRIPTION OF THE INVENTION

Definitions

Figure 1A:
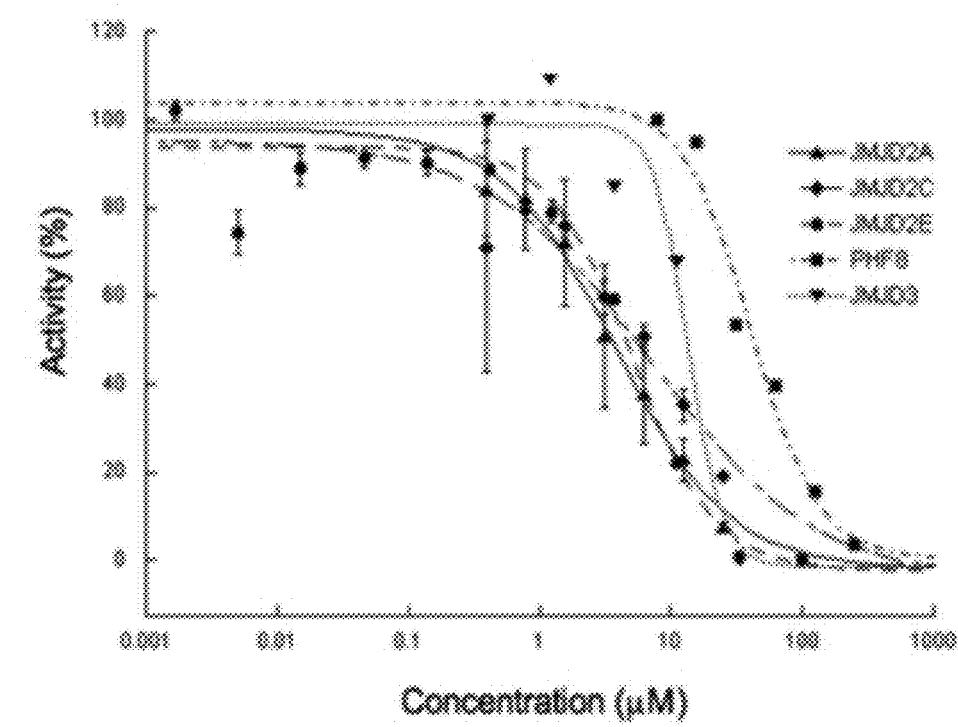
FIG. 1A show in vitro enzyme inhibition data of compound 1 against H3K9me3 demethylases JMJD2A, JMJD2C, and JMJD2E, H3K9me2 demethylase PHF8, and H3K27me3 demethylase JMJD3. Compound 1 showed JHDM-specific inhibitory activity in vitro. Its $IC_{50}$ values against GASC1 and JMJD2A were 4.3 µM and 3.4 µM, respectively. It did not significantly inhibit FAD-dependent histone demethylase LSD1 or HDACs in vitro. Data represent mean values of measurements±s.d.

"Alkyl" refers to a saturated linear monovalent hydrocarbon moiety of one to twenty, typically one to twelve, and often one to six, carbon atoms or a saturated branched monovalent hydrocarbon moiety of three to twenty, typically three to twelve, and often three to six, carbon atoms. Exemplary alkyl group include, but are not limited to, methyl, ethyl, n-propyl, 2-propyl, tert-butyl, pentyl, and the like.

"Alkylene" refers to a saturated linear or branched divalent alkyl group. Exemplary alkylene groups include, but are not limited to, methylene, ethylene, propylene, butylene, pentylene, and the like.

"Alkenyl" means a linear monovalent hydrocarbon moiety of two to twenty, typically two to twelve, often two to eight, and more often two to six carbon atoms or a branched monovalent hydrocarbon moiety of three to twenty, typically three to twelve, often three to eight and more often three to six carbon atoms, containing at least one carbon-carbon double bond, e.g., ethenyl, propenyl, and the like.

"Alkenylene" refers to a linear or branched divalent alkenyl group.

"Alkynyl" means a linear monovalent hydrocarbon moiety of two to twenty, typically two to twelve, often two to eight, and more often two to six carbon atoms or a branched monovalent hydrocarbon moiety of three to twenty, typically three to twelve, often three to eight and more often three to six carbon atoms, containing at least one carbon-carbon triple bond, e.g., ethynyl, propynyl, and the like.

"Alkynylene" refers to a linear or branched divalent alkynyl group.

"Arene" and "arylene" are used interchangeably herein and refer to divalent aryl group.

"Aryl" refers to a monovalent mono-, bi- or tricyclic aromatic hydrocarbon moiety of 6 to 15 ring atoms which is optionally substituted with one or more (e.g., one, two, or three) substituents within the ring structure. When two or more substituents are present in an aryl group, each substituent is independently selected. Exemplary aryl groups include, but are not limited to, phenyl, naphthyl, anthracyl, etc. Exemplary substituents for aryl group include, but are not limited to, halides (e.g., chloro, fluoro, iodo, and bromo), alkyl, haloalkyl, heteroalkyl, aryl, heteroaryl, heterocyclyl, cyano, —$NR^a R^b$ (where each of $R^a$ and $R^b$ is independently hydrogen or alkyl), —XR (where R is hydrogen, alkyl, or carboxylate and X is O or S), etc.

"Aralkyl" refers to a moiety of the formula —$R^b R^c$ where $R^b$ is an alkylene group and $R^c$ is an aryl group as defined herein. Exemplary aralkyl groups include, but are not limited to, benzyl, naphthylmethyl, and the like.

"Chiral center" (i.e., stereochemical center, stereocenter, or stereogenic center) refers to an asymmetrically substituted atom, e.g., a carbon atom to which four different groups are attached. The ultimate criterion of a chiral center, however, is nonsuperimposability of its mirror image.

The terms "halo," "halogen" and "halide" are used interchangeably herein and refer to fluoro, chloro, bromo, or iodo.

"Enantiomeric excess" refers to the difference between the amount of enantiomers. The percentage of enantiomeric excess (% ee) can be calculated by subtracting the percentage of one enantiomer from the percentage of the other enantiomer. For example, if the % ee of (R)-enantiomer is 99% and % ee of (S)-enantiomer is 1%, the % ee of (R)-isomer is 99%-1% or 98%.

The term "heteroaryl" means a monovalent monocyclic, bicyclic, tricyclic, or polycyclic aromatic moiety containing one or more ring heteroatoms each of which is independently selected from N, O, or S, the remaining ring atoms being C. The heteroaryl ring is optionally substituted with one or more substituents. When more than one substituents are present in heteroaryl group each substituent is independently selected. Exemplary substituents for heteroaryl groups include, but are not limited to, alkyl, cyclic alkyl (i.e., cyclyl), halides (e.g., chloro, fluoro, iodo, and bromo), haloalkyl, heteroalkyl, aryl, heteroaryl, heterocyclyl, cyano, —$NR^a R^b$ (where each of $R^a$ and $R^b$ is independently hydrogen or alkyl), —XR (where R is hydrogen, alkyl, or carboxylate and X is O or S), etc. Exemplary heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

"Heterocyclyl" means a non-aromatic monocyclic, bicyclic or polycyclic moiety in which one or more ring atoms are heteroatoms selected from N, O, or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, haloalkyl, heteroalkyl, halo, nitro, cyano, aryl, heteroaryl, etc. Exemplary heterocyclyl includes, but is not limited to, tetrahydropyranyl, piperidino, piperazino, morpholino and thiomorpholino, thiomorpholino-1-oxide, thiomorpholino-1,1-dioxide, and the derivatives thereof.

As used herein, the term "heteroalkyl" means a branched or unbranched, cyclic or acyclic saturated alkyl moiety containing carbon, hydrogen and one or more heteroatoms in place of a carbon atom, or optionally one or more heteroatom-containing substituents such as =O, —$OR^a$, —$C(O)R^a$, —$NR^b R^c$, —$C(O)NR^b R^c$ and —$S(O)_n R^d$ (where n is an integer from 0 to 2). $R^a$ is hydrogen, alkyl, haloalkyl, cycloalkyl, cycloalkylalkyl, heterocyclyl, heterocyclylalkyl, aryl, aralkyl, heteroaryl, heteroaralkyl, or acyl. $R^b$ is hydrogen, alkyl, haloalkyl, cycloalkyl, cycloalkylalkyl, heterocyclyl, heterocyclylalkyl, aryl, aralkyl, heteroaryl, heteroaralkyl, or acyl. $R^c$ is hydrogen, alkyl, haloalkyl, cycloalkyl, cycloalkylalkyl, heterocyclyl, heterocyclylalkyl, aryl, aralkyl, acyl, alkylsulfonyl, carboxamido, or mono- or di-alkylcarbomoyl. Optionally, $R^b$ and $R^c$ can be combined together with the nitrogen to which each is attached to form a four-, five-, six- or seven-membered heterocyclic ring (e.g., a pyrrolidinyl, piperidinyl or morpholinyl ring). $R^d$ is hydrogen (provided that n is 0), alkyl, haloalkyl, cycloalkyl, cycloalkylalkyl, heterocyclyl, heterocyclylalkyl, aryl, aralkyl, heteroaryl, heteroaralkyl, acyl, amino, monosubstituted amino, disubstituted amino, or hydroxyalkyl. Representative examples include, for example, 2-methoxyethyl, benzyloxymethyl, thiophen-2-ylthiomethyl, 2-hydroxyethyl, and 2,3-dihydroxypropyl.

"Heteroaralkyl" means a moiety —$R^a R^b$ where $R^a$ is an alkylene group and $R^b$ is a heteroaryl group as defined above, e.g., pyridin-3-ylmethyl, 3-(benzofuran-2-yl)propyl, and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to a pharmacologically substantially inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, *Design of Prodrugs*, pp. 7-9, 21-24, Elsevier, Amsterdam 1985 and Silverman, *The Organic Chemistry of Drug Design and Drug Action*, pp. 352-401, Academic Press, San Diego, Calif., 1992). Prodrugs commonly known in the art include acid derivatives that are well known to one skilled in the art, such as, but not limited to, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability. For example, a compound of the invention having free amino, amido, hydroxy or carboxylic groups can be converted into prodrugs.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, $3^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, or S) to which it is attached.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as any narrow and/or preferred, more preferred and most preferred definitions, if any.

Compounds of the Invention

Some aspects of the invention provide compounds of the formula: M-L-K, or a derivative or a prodrug thereof, wherein M is a methyllysine mimic, L is a linker, and K is an α-ketoglutarate mimic. The term "methyllysine mimic" refers to a moiety that has similar or better characteristics and/or properties of methylated lysine in binding with a complex of JHDM and α-ketoglutarate. Determination of whether a particular moiety is a methyllysine mimic can be readily determined by one skilled in the art, for example, by performing computer modeling and/or determining in vitro activity. Similarly, the term "α-ketoglutarate mimic" refers to a moiety that has similar and/or better characteristics and properties of α-ketoglutarate in binding with JHDM. Determination of whether a particular moiety is an α-ketoglutarate mimic can also be readily determined by one skilled in the art, for example, by performing computer modeling and/or determining in vitro activity.

In some embodiments, the linker comprises from 2 to 15 chain atoms each of which is independently selected from the group consisting of C, O, and S, provided that no two heteroatoms are linked to one another. Typically, the linker comprises $C_2$-$C_{12}$ carbon chain atoms. Often the linker is a $C_2$-$C_{12}$ alkylene, $C_2$-$C_{12}$ alkenylene, $C_2$-$C_{12}$ alkynylene, or —$R^a$—$R^b$—$R^c$— (where each of $R^a$ and $R^c$ is independently alkylene and $R^b$ is arylene or heteroarylene). In one particular embodiment, the linker is a $C_2$-$C_{12}$ alkylene or —$CH_2$—$R^b$—$CH_2$— (where $R^b$ is arylene or heteroarylene).

Still in other embodiments, the methyllysine mimic is of the formula:

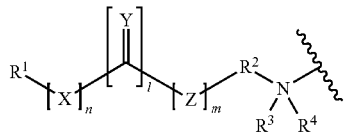

where
each of l, m and n is independently 0 or 1;
each of X and Z is independently O, S, or $NR^5$;
Y is O, S or $NR^5$;
$R^1$ is aryl, aralkyl, fluorescein, or heteroaryl each of which is optionally substituted;
$R^2$ is alkylene or a moiety of the formula —$R^6$—$Ar^1$—$R^7$—, wherein each of $R^6$ and $R^7$ is independently alkylene, and $Ar^1$ is arylene;
$R^3$ is hydrogen, alkyl, aralkyl, heteroalkyl, heteroaralkyl;
$R^4$ is hydrogen, alkyl, or absent; and
each $R^5$ is independently hydrogen or alkyl.

Within these embodiments, in some instances $R^1$ is phenyl, naphthyl, benzyl, naphthylalkyl (e.g., naphthylmethyl), fluoresceinyl, or quinolinyl, each of which is optionally substituted. When $R^1$ is phenyl, it is sometimes optionally substituted with one or two halide such as fluoride, chloride, or bromide, methyl, amino, or mono- or dialkyl amino. In some particular instances, X is NH. Still in other particular instances, Y is O. Yet in other instances, Z is O or NH. In other instances, $R^2$ is $C_3$-$C_8$ alkylene. Still yet in other particular instances, $R^6$ and $R^7$ are methylene. Yet still in other particular instances, $Ar^1$ is phenylene. Still in other particular instances, $R^4$ is alkyl or absent.

Yet in other embodiments, 1 is 1.

In other embodiments, $R^3$ is hydrogen, alkyl (e.g., methyl, ethyl, isopropyl, isobutyl, isopentyl, etc.), hydroxybenzyl, pyrazolylmethyl, —$CO_2R$ substituted benzyl (where R is hydrogen or alkyl), hydroxymethyl substituted benzyl, heteroalkyl (e.g., —$R^a$—$CO_2R^b$, where $R^a$ is alkylene and $R^b$ is hydrogen or alkyl or —$R^a$—$NR^cR^d$ where $R^a$ is alkylene and each of $R^c$ and $R^d$ is independently hydrogen, alkyl or carboxyl), —$NR^aR^b$ substituted benzyl (where each of $R^a$ and $R^b$ is independently hydrogen, alkyl, or carboxyl (i.e., —C(=O)$R^c$, where $R^c$ is alkyl).

In some embodiments, the α-ketoglutarate (i.e., "α-KG") mimic is of the formula:

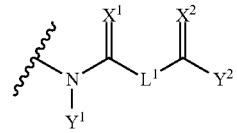

where
$Y^1$ is $OR^8$, or —$NHR^8$;
each of $X^1$ and $X^2$ is independently O, S, or $NR^9$;
$Y^2$ is —$OR^8$, —$SR^{10}$, or —$NR^{11}R^{12}$;
each $R^8$ is independently hydrogen, alkyl, or a hydroxyl protecting group;
each $R^9$ is independently hydrogen, alkyl, or a nitrogen protecting group;
$R^{10}$ is hydrogen, alkyl, or a sulfur protecting group;
$R^{11}$ is hydrogen or alkyl;
$R^{12}$ is hydrogen, alkyl, or a nitrogen protecting group; and
$L^1$ is alkylene, alkenylene, arene, or alkynylene.

Within these embodiments, in some instances $R^8$ is hydrogen or $C_1$-$C_4$ alkyl. In other instances, $X^1$ and $X^2$ are O, Still in other instances, $Y^2$ is —$OR^8$. Yet in other instances, $L^1$ is $C_2$-$C_6$ alkylene or $C_2$-$C_6$ alkenylene.

Still in other embodiments, some of the compounds of the invention are of the formula:

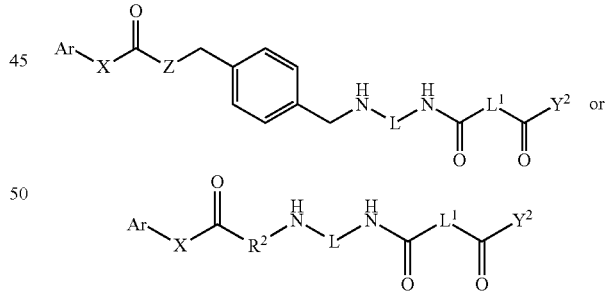

where Ar is phenyl, naphthyl, fluoresceinyl, or quinolinyl, each of which is optionally substituted, $R^2$, X, Z, L, $L^1$ and $Y^2$ are those defined herein.

It should be appreciated that combinations of the various embodiments and instances described herein form other embodiments. For example, in one particularly embodiment $R^1$ is naphthyl, each of l, m, and n is 1, X is NH, Y is O, Z is O, $R^2$ is —$CH_2$-Ph-$CH_2$—, $R^3$ is H, $R^4$ is absent, $Y^1$ is —OH, $X^1$ and $X^2$ are O, $L^1$ is pentylene, and $Y^2$ is —$OCH_3$. In this manner, a variety of compounds are embodied within the present invention.

Representative compounds of the invention include, but are not limited to those shown in Table 1 below.

TABLE 1
Representative Compounds of the Invention.
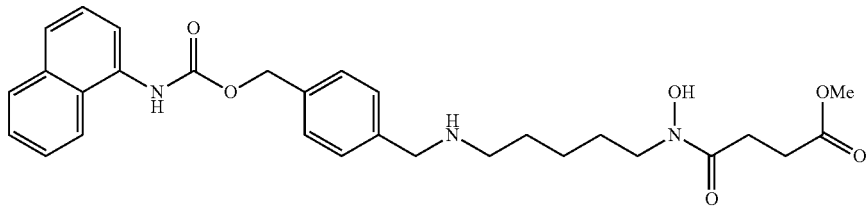
YXL-IV-15
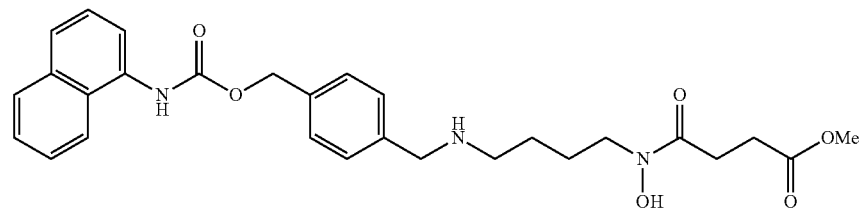
YXL-II-133
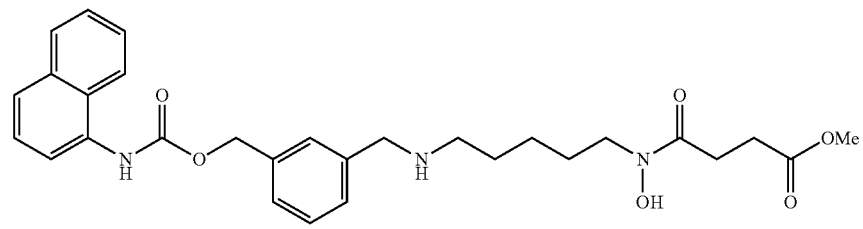
YXL-IV-17
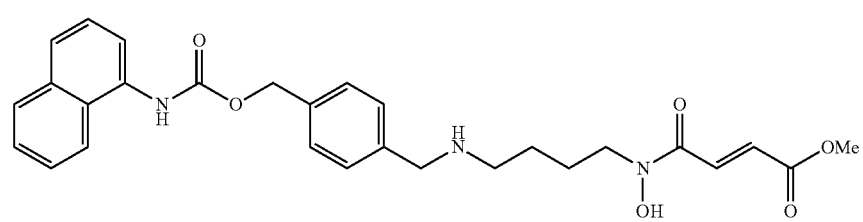
YXL-IV-22
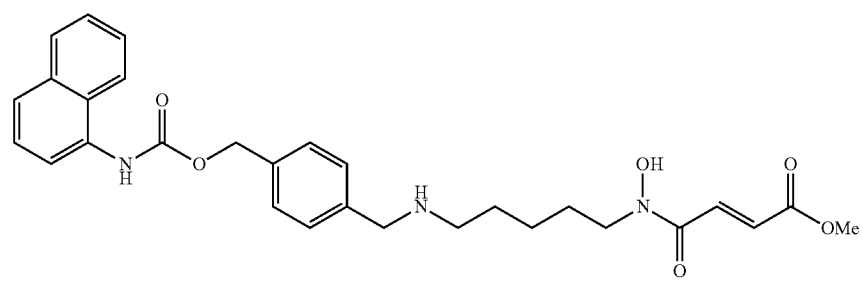
YXL-IV-23
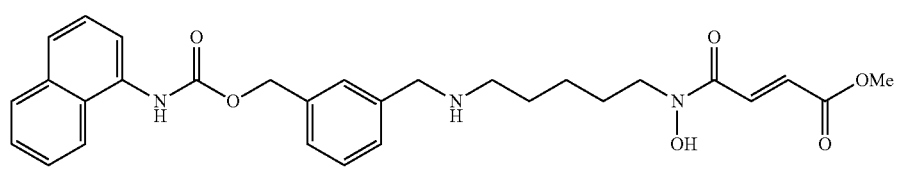
YXL-IV-24

TABLE 1-continued
Representative Compounds of the Invention.
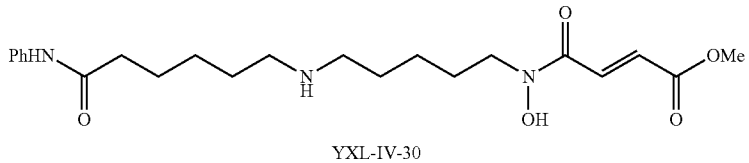
YXL-IV-30
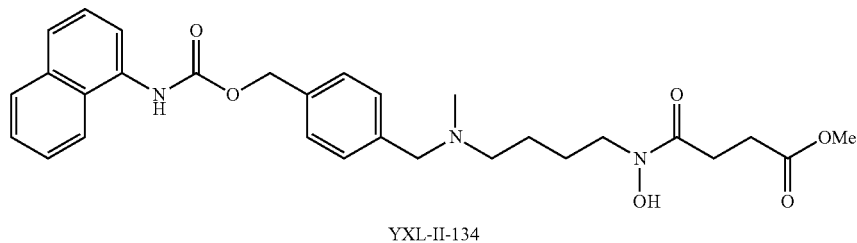 [SMILES: COC(=O)CCC(=O)N(O)CCCCN(C)Cc1ccc(COC(=O)Nc2cccc3ccccc23)cc1]
YXL-II-134
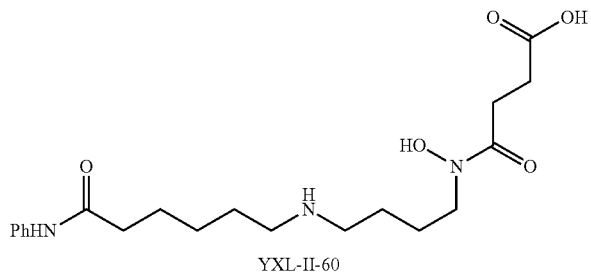
YXL-II-60
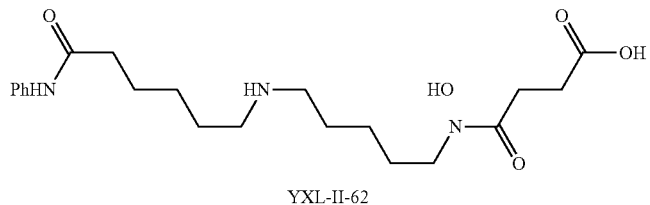
YXL-II-62
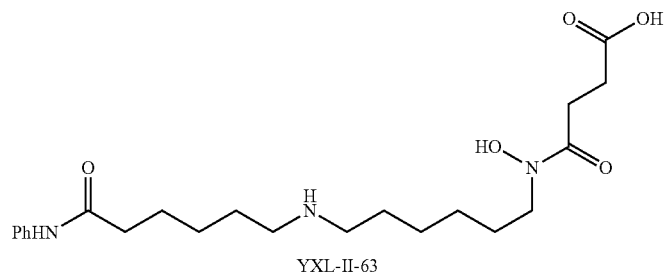
YXL-II-63
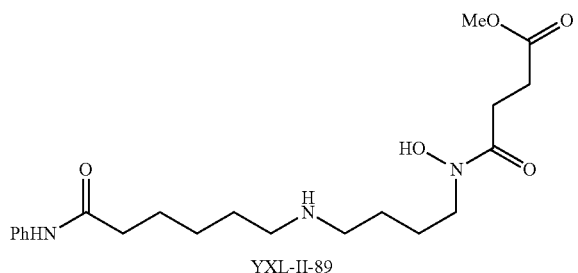
YXL-II-89

TABLE 1-continued
Representative Compounds of the Invention.
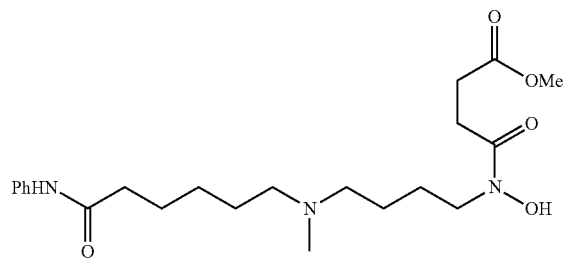
YXL-II-98
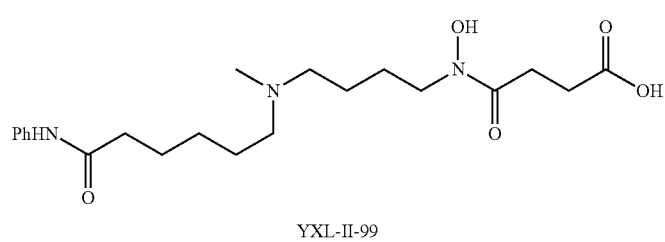
YXL-II-99
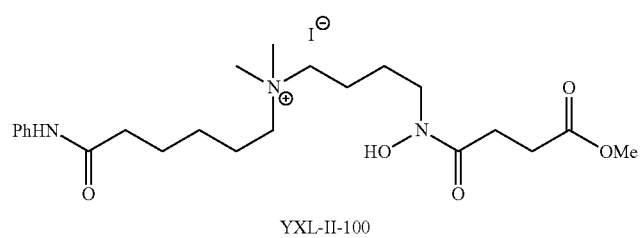
YXL-II-100
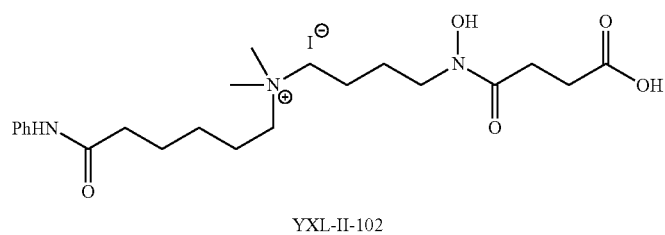
YXL-II-102
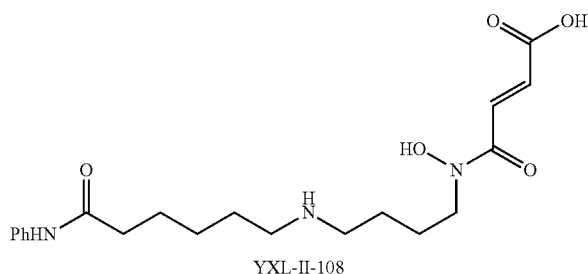
YXL-II-108
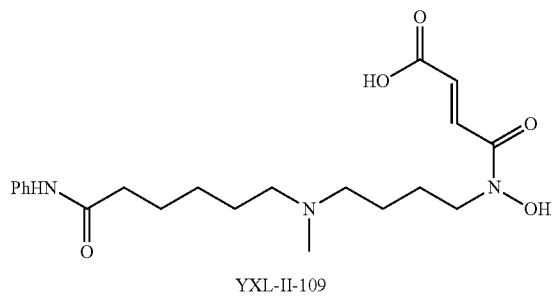
YXL-II-109

TABLE 1-continued
Representative Compounds of the Invention.
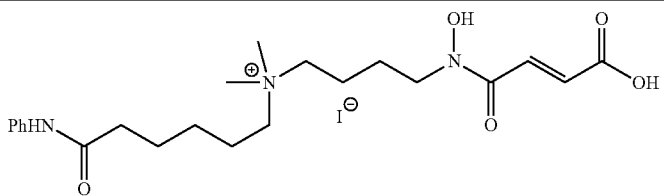
YXL-II-111
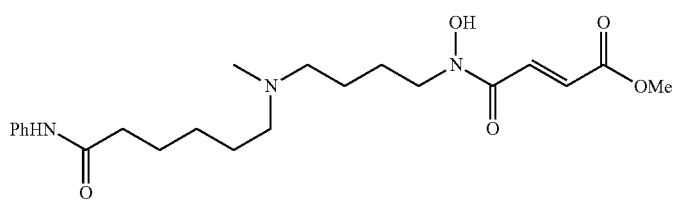
YXL-II-107
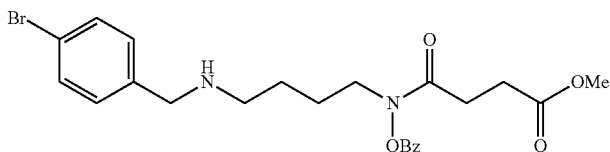
YXL-II-127
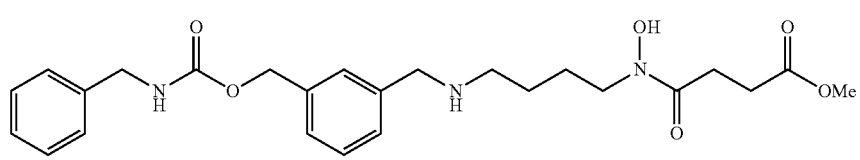
YXL-II-147
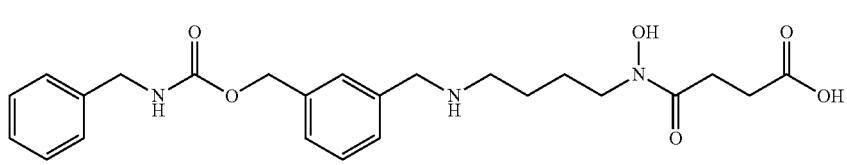
YXL-II-149
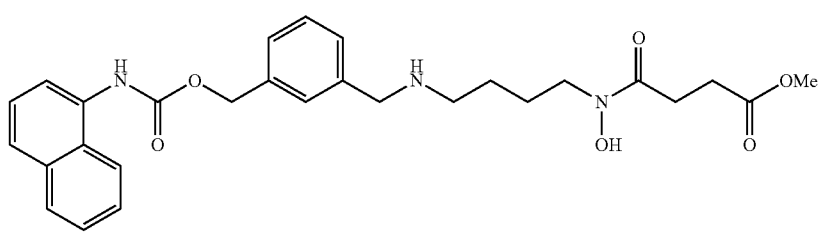
YXL-II-150
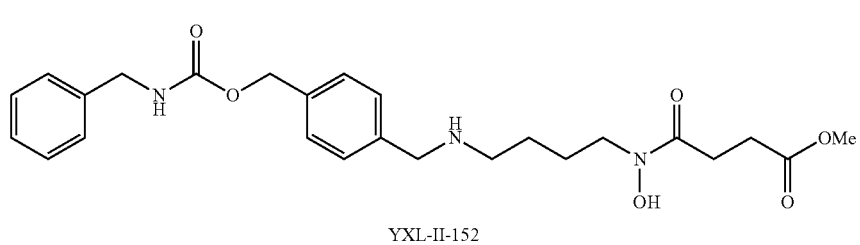 [SMILES: COC(=O)CCC(=O)N(O)CCCCNCc1ccc(COC(=O)NCc2ccccc2)cc1]
YXL-II-152

TABLE 1-continued

Representative Compounds of the Invention.

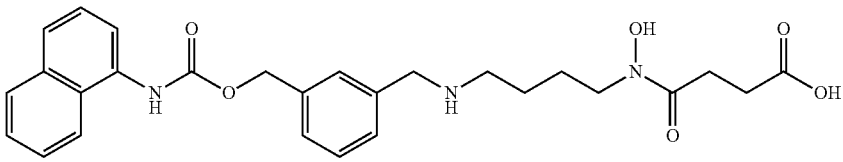

YXL-II-154

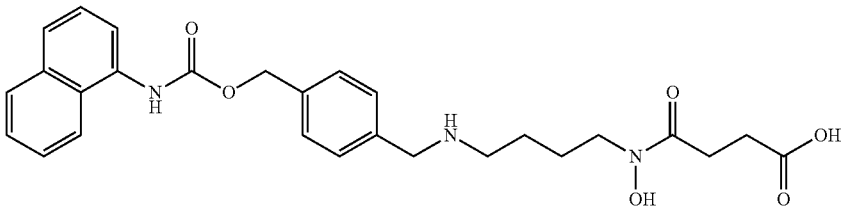

YXL-II-155

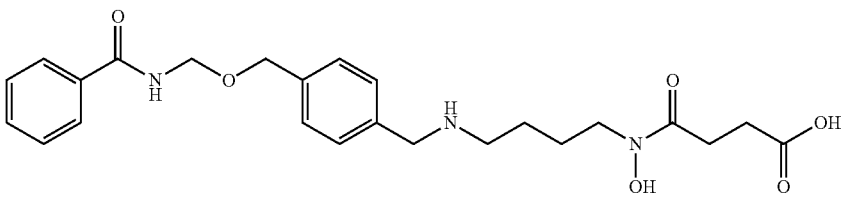

YXL-II-156

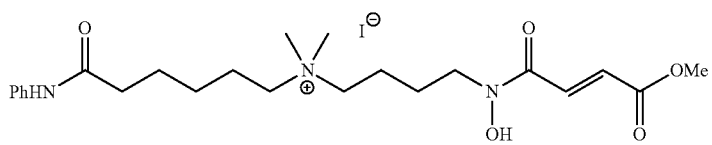

YXL-II-175

Other representative compounds of the invention are provided in Examples section below.

Synthesis

The compounds of the present invention can be synthesized from readily available starting materials. Various substituents on the compounds of the present invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in *Protective Groups in Organic Synthesis*, 2nd edition, T. H. Greene and P. G. M. Wuts, John Wiley & Sons, New York, 1991, which is incorporated herein in its entirety. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Since the compounds of the present invention can have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art. This would further be dependent on the ring involved.

If the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium *Optical Resolution Procedures for Chemical Compounds*: Optical Resolution Information Center, Manhattan College, Riverdale, N.Y., and in *Enantiomers, Racemates and Resolutions*, Jean Jacques, Andre Collet and Samuel H. Wilen; John Wiley & Sons, Inc., New York, 1981, which are incorporated herein in their entirety. Basically, the resolution of the compounds is based on the differences in the physical properties of diastereomers by attachment, either chemically or enzymatically, of an enantiomerically pure moiety results in forms that are separable by fractional crystallization, distillation or chromatography.

In some resolution methods, a racemic mixture is converted to a mixture of diasteromers by attachment, either chemically or enzymatically, of a relatively enantiomerically pure moiety. Unlike enantiomers, most diastereomers have different physical properties, e.g., solubility, boiling point, affinity (e.g., to chromatography columns and enzymes), and the like. These different physical properties can be used to separate one diastereoisomer from another, for example, by fractional crystallization, distillation, chromatography, kinetic resolution using an enzyme, and the like.

It is to be understood that the scope of this invention encompasses not only the various isomers which may exist but also the various mixture of isomers which may be formed.

When the compound of the present invention contains an olefin moiety and such olefin moiety can be either cis- or trans-configuration, the compound can be synthesized to produce cis- or trans-olefin, selectively, as the predominant product. Alternatively, the compound containing an olefin moiety can be produced as a mixture of cis- and trans-olefins and separated using known procedures, for example, by chromatography as described in W. K. Chan, et al., *J. Am. Chem. Soc.*, 1974, 96, 3642, which is incorporated herein in its entirety.

The compounds of the present invention form salts with acids when a basic amino function is present and salts with bases when an acid function, e.g., carboxylic acid or phosphonic acid, is present. All such salts are useful in the isolation and/or purification of the new products. Of particular value are the pharmaceutically acceptable salts with both acids and bases. Suitable acids include, for example, hydrochloric, oxalic, sulfuric, nitric, benzenesulfonic, toluenesulfonic, acetic, maleic, tartaric and the like which are pharmaceutically acceptable. Basic salts for pharmaceutical use include Na, K, Ca and Mg salts.

A more detailed example of synthesizing compounds of the invention is provided in the Examples section below.

Utility

Compounds of the invention are JHDMs inhibitors. In some aspects of the invention, compounds of the invention are cell-active specific inhibitors of JHDMs. Accordingly, compounds of the invention and compositions comprising a compound of the invention are useful in treating clinical conditions associated with the activity of Jumonji C Domain-Containing Histone Demethylase and/or a clinic condition associated with overexpression of Jumonji C Domain-Containing Histone Demethylase. Exemplary clinical conditions associated with the activity and/or overexpression of JHDMs include, but are not limited to, cancer (e.g., prostate cancer, testis cancer, esophageal squamous carcinoma, and breast cancer) and mental retardation. Other clinical conditions associated with activity and/or overexpression of JHDMs are well known to one skilled in the art. See, for example, *Chem Med Chem.*, 2009, 4, 1568-1582, which is incorporated herein by reference in its entirety.

The compounds of the present invention can be administered to a subject to achieve a desired physiological effect. Typically, the subject is an animal, often a mammal, and more often a human. The compound can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparation can contain at least 0.1% of active compound. The percentage of the compositions and preparation can, of course, be varied and can conveniently be between about 1 to about 10% of the weight of the unit. The amount of active compound in such therapeutically useful compositions is such that a suitable dosage will be obtained. Preferred compositions or preparations according to the present invention are prepared such that an oral dosage unit form contains from about 1 to about 1000 mg of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens, preservatives, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulation. In addition to the common dosage forms set out above, the compounds of the present invention may also be administered by controlled release means and/or delivery devices capable of releasing the active ingredient (prenylation inhibitor) at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. Examples of controlled release pharmaceutical compositions and delivery devices that may be adapted for the administration of the active ingredients of the present invention are described in U.S. Pat. Nos. 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are hereby incorporated by reference.

Pharmaceutical compositions for use in the methods of the present invention may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

The active compound can also be administered parenterally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of the present invention can be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Several JHDMs crystal structures have been solved, most of which are complexed with methyllysine-containing histone peptides and cofactor mimics. Based on these crystal structures and the enzymatic mechanism of JHDMs, the present inventor designed and synthesized a series of potential JHDM-selective small-molecule inhibitors, each of which contained a methyllysine mimic (substrate mimic), an α-ketoglutarate mimic (cofactor mimic), and a linker combining these two (FIG. 1a). It has been discovered by the present inventor that a compound of the invention [e.g., a compound 1 (FIG. 1a)] is a specific JHDM inhibitor in vitro, and its corresponding methyl ester prodrug 2 is a specific JHDM inhibitor in vivo.

Figure 1B:
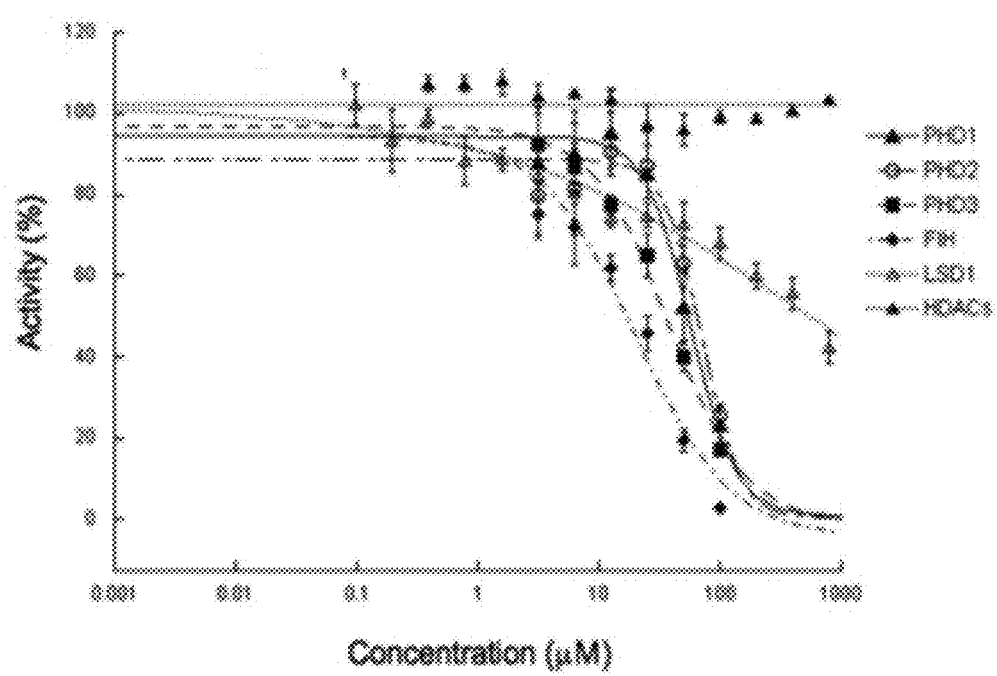
FIG. 1B shows enzyme inhibition data of compound 1 against prolyl hydroxylases PHD1-3, factor inhibiting hypoxia-inducible factor FIH, an asparaginyl hydroxylase, FAD-dependent histone demethylase LSD1, and histone deacetylases HDACs.
Figure 3:
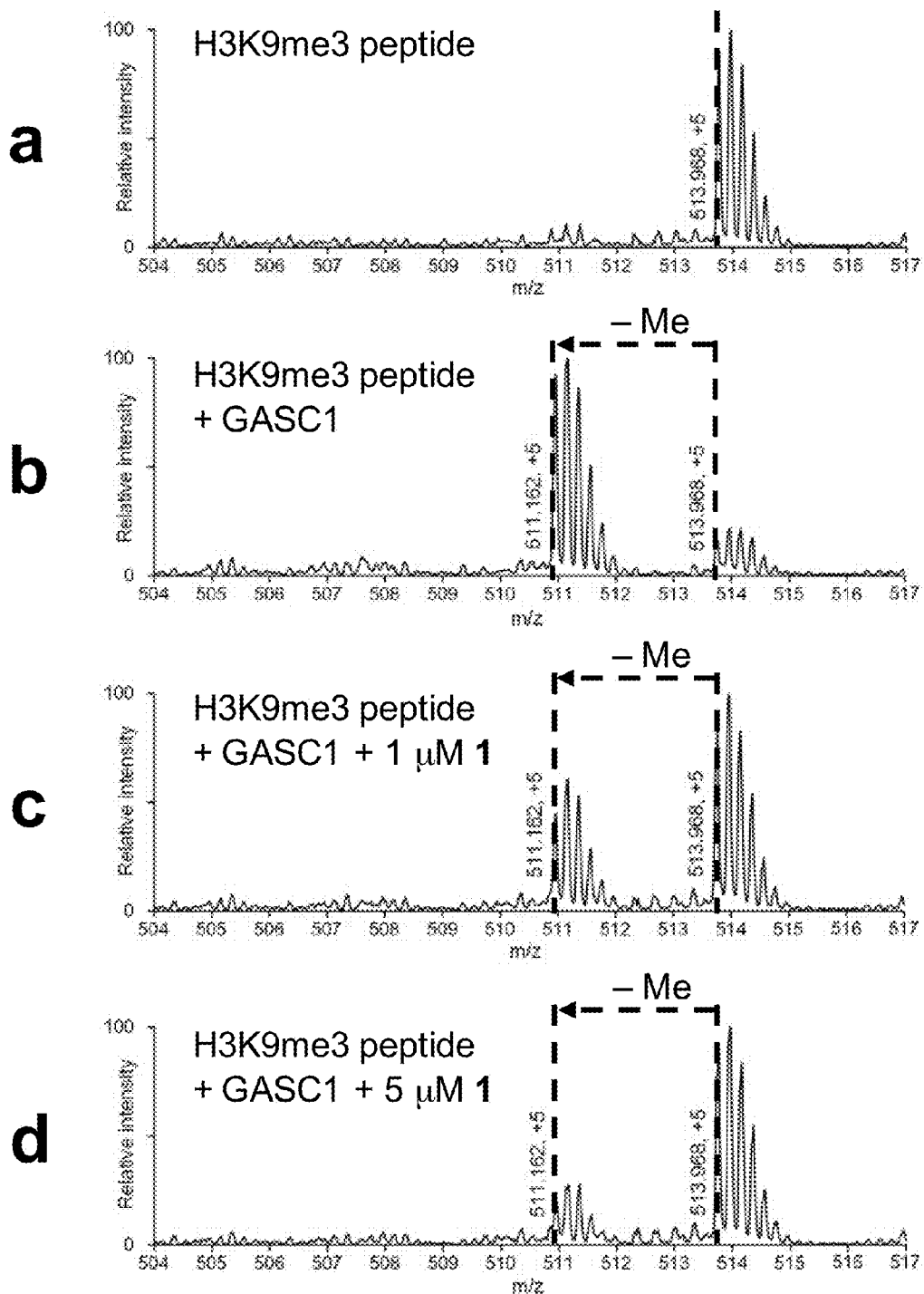
FIGS. 3A-3D are mass spectrum data showing Compound 1 inhibited GASC1-mediated demethylation of H3K9me3 peptides.

In order to evaluate the inhibitory activity of 1 in vitro, a GST-fusion protein of the catalytic N-terminus of human GASC1 (gene amplified in squamous cell carcinoma 1) corresponding to amino acid 1-420 was cloned and purified. The JHDM GASC1/JMJD2C predominantly uses H3K9me3 substrates, but has also been shown to demethylate H3K36me3. By using ESI-TOF spectrometry, it was found that this purified protein can remove the methyl group of a synthetic biotinylated 20-residue histone H3 fragment peptide substrate (H3K9me3, see FIG. 3). Compound 1 showed a half maximal inhibitory concentration ($IC_{50}$) for GASC1 of approximately 4.3 µM determined by a dissociation-enhanced lanthanide fluorescent immunoassay (DELFIA, FIG. 1b). To evaluate the enzyme specificity of 1, the activity of 1 was examined against several other related enzymes in vitro. Compound 1 inhibited another H3K9me3 JHDM, JMJD2A, with an $IC_{50}$ value of approximately 3.4 µM, but it did not significantly inhibit either the FAD-dependent HDM LSD1 or another class of histone lysine modifying enzymes, histone deacetylases (HDACs, FIG. 1b).

Figure 2A:
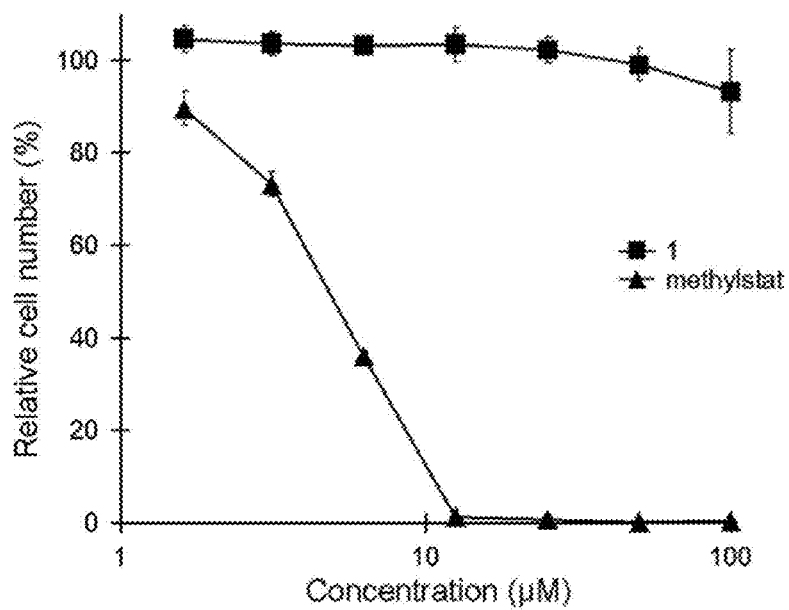
FIGS. 2A-2E are various data showing methylstat as a specific JHDM inhibitor in vivo.
Figure 2B:
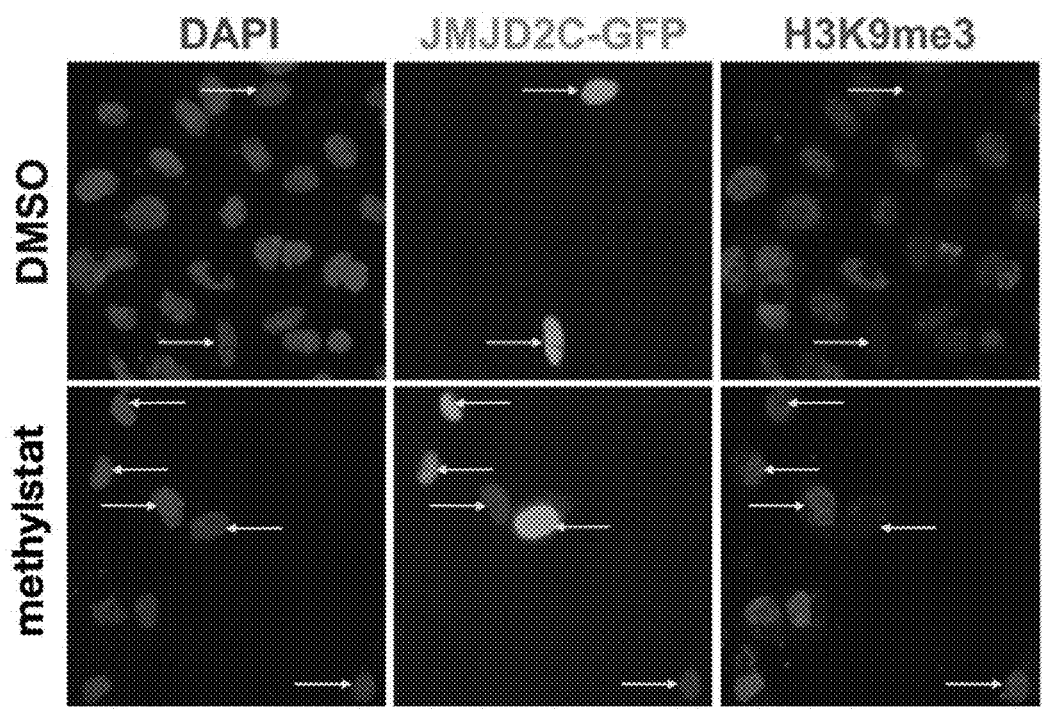
Figure 4:
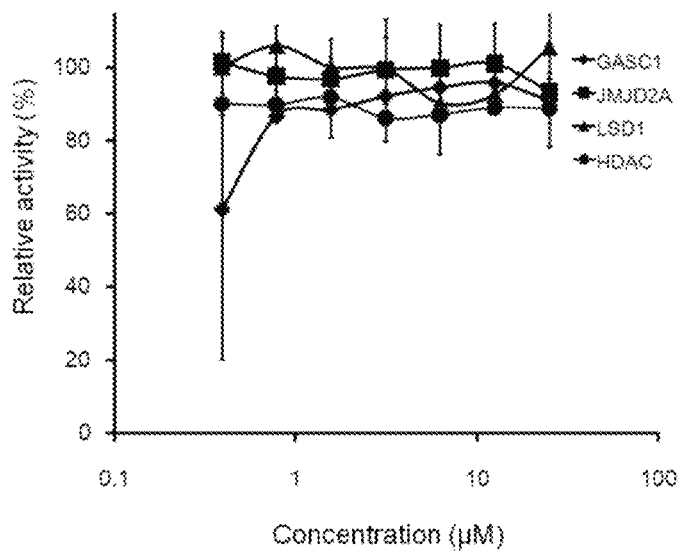
FIG. 4 is a graph showing that methylstat did not significantly inhibit either HDMs or HDACs in vitro. Data represent mean values of measurements±s.d.

To examine the cellular activity of the compounds of the invention, oesophageal carcinoma cell line KYSE150 was used in a growth inhibition assay because KYSE150 cells have been reported to contain several copies of the GASC1 gene, and it has been reported that inhibition of GASC1 expression using short hairpin RNA causes a significant reduction of proliferation in KYSE150 cells. Compound 1 did not show significant growth inhibition at up to 100 µM. Without being bound by any theory, it is believed that this low activity in cells was possibly due to the poor cellular uptake of the zwitterion form in which it typically exists under physiological conditions. Therefore, its methyl ester prodrug 2 (FIG. 1a), called methylstat was tested. Methylstat did not significantly inhibit the enzymatic activities of GASC1, JMJD2A, LSD1, or HDACs (see FIG. 4) in vitro, but inhibited KYSE150 cell growth with a half maximal growth inhibitory concentration ($GI_{50}$) at approximately 5.1 µM (FIG. 2a). To prove GASC1 is the cellular target of methylstat, a GFP-fusion protein of the catalytic N-terminus of GASC1(1-420) was ectopically expressed in human epithelial carcinoma HeLa cells. Successfully transfected cells (green cells in FIG. 2b) showed a significant reduction of H3K9me3 level as indicated by an immunostaining assay, and this effect was reversed by the treatment of the cells with methylstat at 10 µM.

Figure 2C:
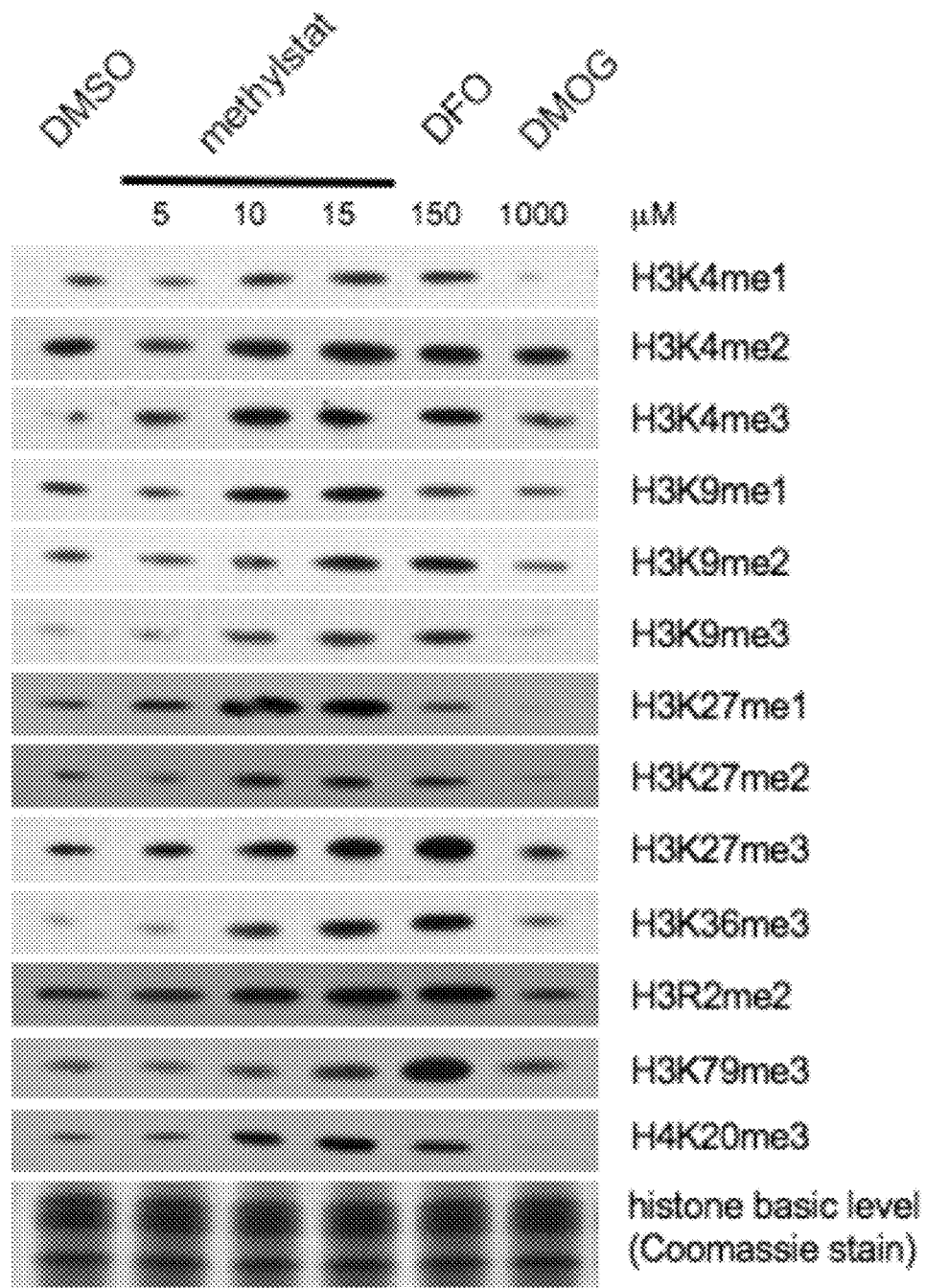
Figure 5:
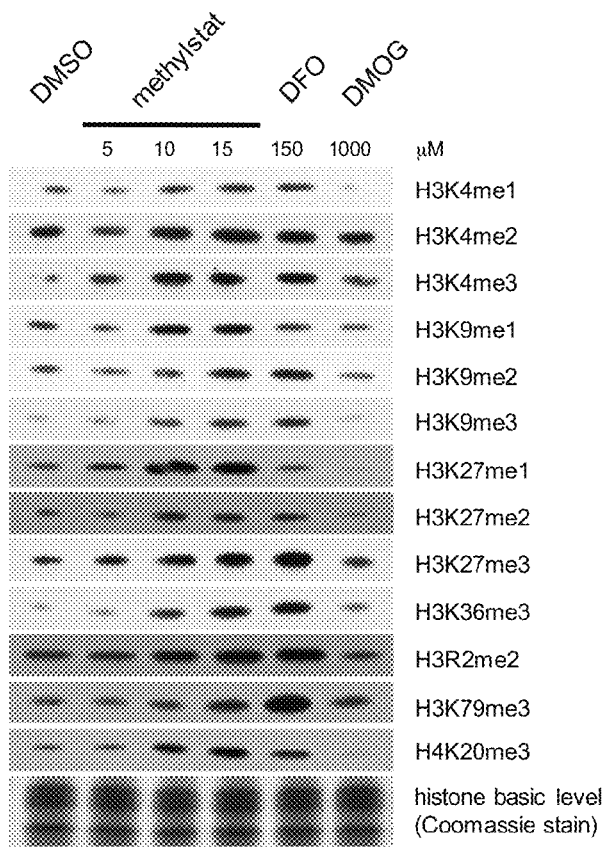
FIG. 5 is electrophoretic slides showing that methylstat induced hypermethylations of histone proteins in a concentration-dependent manner. MCF7 cells were treated with DMSO, DFO at 150 µM, DMOG at 1 mM, and methylstat at 5, 10, and 15 µM for 48 hours, respectively.

Next, the cellular effects of methylstat were evaluated on a variety of histone methylation marks in KYSE150 cells. DMOG and DFO were used as positive controls, since they are known cell-active inhibitors of iron (II)- and α-ketoglutarate-dependent dioxygenases. Western blotting experiments showed that methylstat induced hypermethylation of lysine residues including H3K4, H3K9, H3K27, and H3K36 at almost all methylation states in a concentration-dependent manner (FIG. 2c). In addition, methylstat also induced hypermethylation of the arginine residue H3R2, probably due to the similarity of lysine and arginine and their corresponding JHDMs. To further validate these results, the cellular effect of methylstat in human breast adenocarcinoma MCF7 cells were examined, and found that it also induced concentration-dependent hypermethylation of lysine and arginine residues on histone proteins (see FIG. 5). Of substantial interest was the observation that methylstat also induced increased cellular levels of H3K79me3 and H4K20me3. These results indicate that these histone methylation marks can also be removed by some as yet unknown Jumonji C domain-containing proteins.

Figure 2D:
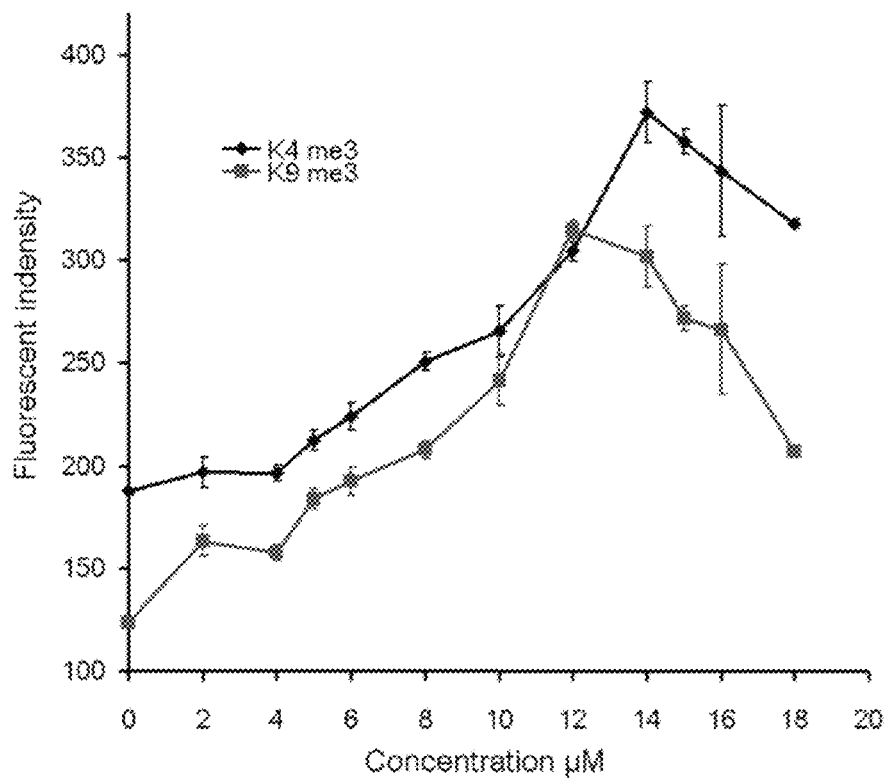
Figure 6:
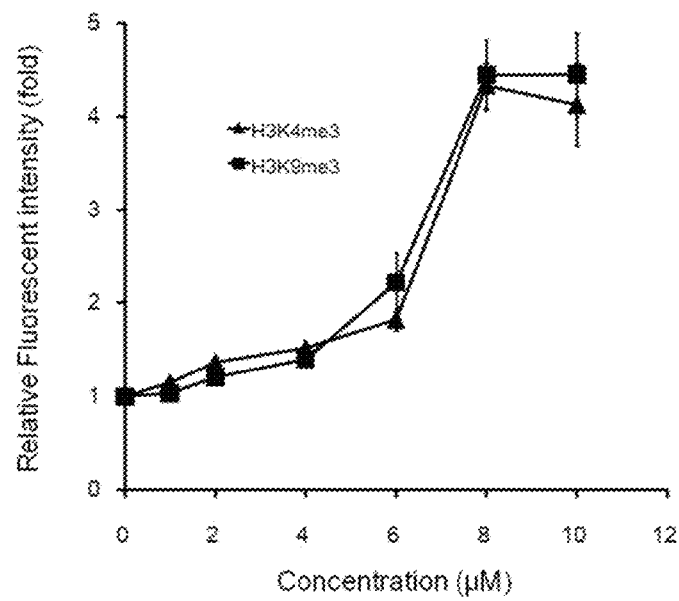
FIG. 6 is a graphic data showing $EC_{50}$ values of methylstat for H3K4me3 and H3K9me3 in MCF7 cells as determined by quantifying images from immunostaining assays as 6.7 µM and 6.3 µM, respectively. Data represent mean values of measurements±s.d.

To quantify the cellular activity of methylstat, a quantitative image-based assay was used. Immunostaining of KYSE150 cells treated with DMSO or methylstat showed that the cellular levels of both H3K4me3 and H3K9me3 increased in a concentration-dependent fashion (FIG. 2d). Quantification of the images derived from the immunostaining experiments provided the half maximal effective concentrations ($EC_{50}$) for H3K4me3 and H3K9me3 as 10.3 µM and 8.6 µM, respectively. The cellular effects of methylstat were also cell type-specific. In MCF7 cells, the $EC_{50}$ values of methylstat for H3K4me3 and H3K9me3 were 6.7 µM and 6.3 µM, respectively (see FIG. 6). It is noteworthy that methylstat induced much higher increase of the H3K9me3 mark in KYSE150 cells compared with that in MCF7 cells (10.8 fold vs. 4.5 fold), probably due to higher expression level of GASC1 in KYSE150 cells.

Figure 2E:
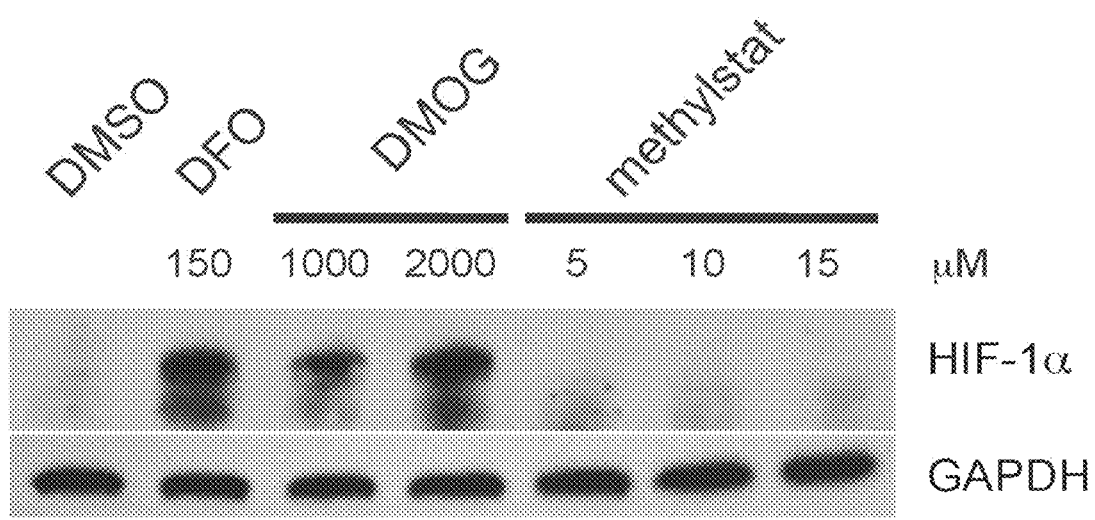
Figure 7:
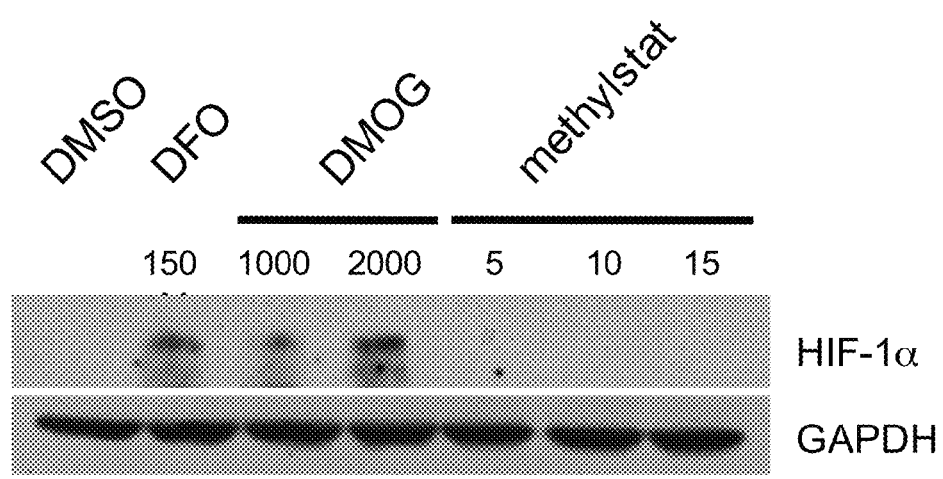
FIG. 7 is electrophoretic data showing methylstat did not significantly inhibit prolyl hydroxylases. HeLa cells were treated with DMSO, DFO at 150 µM, DMOG at 1 and 2 mM, methylstat at 5, 10, and 15 µM for 24 hours, respectively.

To assess the specificity of methylstat in vivo, another iron(II)- and α-ketoglutarate-dependent dioxygenases, prolyl hydroxylases (PHDs), was examined. PHDs have been reported to regulate normoxic inactivation of hypoxia-inducible factors (HIFs) by hydroxylating specific prolyl residues of HIFs. Inhibition of PHDs resulted in higher stability of HIFs and accumulation of HIFs in cells. DMOG and DFO have been used to mimic hypoxia conditions by inhibiting PHDs in vivo. MCF7 cells treated with DMOG or DFO showed significantly increased cellular levels of HIF-1α, whereas methylstat did not affect the cellular HIF-1α levels at up to 15 µM, the highest concentration tested (FIG. 2e). Similar results were also observed in HeLa cells (see FIG. 7).

As can be seen, many compounds of the invention are cell-active and specific inhibitor of Jumonji C domain-containing histone demethylases. For example, compound 1 showed specific inhibitory activity against JHDMs in vitro, and its prodrug methylstat showed specific cellular activity against all JHDMs. In addition, induction of hypermethylation of H3K79 and H4K20 in cells by methylstat also indicated the existence of novel JHDMs specifically targeting these important chromatin marks. This discovery provides a powerful small-molecule probe that specifically targets histone demethylases. Together with other small-molecule regulators of histone-modifying enzymes, compounds of the invention, e.g., methylstat, can be used in a wide variety of applications including, but not limited to, studying histone methylation dynamics in a wide range of biological processes, such as embryonic development and differentiation, germline maintenance and meiosis, and regulation of gene expression, and of disease processes, such as those leading to the development of cancer.

Materials and Methods.

Synthetic peptides 20 amino acids long mimicking the N-terminal tail (1-20) of histone H3 dimethylated or trimethylated at lysine K4 (biotin-ART[Kme2]QTARKS TGGKAPRKQL or biotin-ART[Kme3]QTARKSTG-GKAPRKQL) or trimethylated at lysine K9 (biotin-ART-KQTAR[Kme3]STGGKAPRKQL) were purchased from Sigma. Antibodies used in the study were as follows: anti-H3K4me3 (Upstate 07-473), anti-H3K4me2 (Upstate 07-030), anti-H3K4me (Upstate 07-436), anti-H3K9me3 (Upstate 07-523), anti-H3K9me2 (Upstate 07-521), anti-H3K9me (Abcam Ab9045-50), anti-H3K27me3 (Abcam ab-6002), anti-H3K27me2 (Upstate 07-452), anti-H3K27me (Upstate 07-448), anti-H3K36me3 (Abcam ab-9050), anti-H3K79me3 (Abcam ab2621), anti-H4K20me3 (Upstate 07-463), anti-HIF-1α (Abcam ab1-250), and anti-GAPDH (Abcam ab-9484).

Cell Lines and Reagents

Human oesophageal squamous cell carcinoma cell line KYSE150 was obtained from the German Collection of Microorganisms and Cell Cultures, Braunschweig, Germany. Human breast cancer cell line MCF7 and cervical cancer cell line HeLa were obtained from American Type Culture Collection (ATCC). KYSE150 cells were maintained in 49% RPMI 1640, 49% Ham's F12 supplemented 2% fetal calf serum (FCS), 1% penicillin/streptomycin, 5% $CO_2$. All other cells were maintained at 37° C. in Dulbecco's modified Eagle's medium (DMEM) supplemented with 10% fetal calf serum (FCS), 1% penicillin/streptomycin, 5% $CO_2$. The compounds were added, and 0.1% DMSO was added as the control. DFO (deferoxamine mesylate salt), DMOG (dimethyl oxalylglycine), alpha-ketoglutarate, and all other chemicals were obtained from Sigma unless otherwise stated.

DNA Constructs

The putative open reading frame of human GASC1, JMJD2A and LSD1 was amplified by PCR from HeLa cDNA and cDNA from a human fetal brain cDNA library (Invitrogen, Carlsbad, Calif.). Primer sequences are available upon request. PCR products were gel purified, cloned into pDO-NOR221 (Invitrogen), and verified by DNA sequencing. Entry clones were recombined into respective target vectors by GATEWAY LR reaction. For transient transfection, pEGFP-GW was used, which contained the GFP-fusion and GATEWAY cassette from pEGFP-GW.

Protein Purification

Recombinant protein preparation of GASC1(1-420), JMJD2A (1-420) and LSD1 (full-length) was expressed as glutathione S-transferase (GST) fusions using the GST-parallel expression vector (pDEST-15) or a previously described Gateway GST vector. The protein coding sequences were verified by sequencing. Following expression in BL-21 *Escherichia coli*, proteins were purified using glutathione agarose beads (Amersham Biosciences) according to the manufacturer's instructions.

Assay Protocols
GASC1 Enzyme Inhibition Assay with MS Detection

Synthetic histone peptides H3K9me3 were incubated with purified GST-tagged GASC1(1-420) in demethylation buffer (50 mM Tris pH 8.0, 2 mM $ZnCl_2$, 1 mM alpha-ketoglutarate, 50 µM $FeSO_4$, 1 mM ascorbic acid) at 37° C. In a typical reaction, 2 µg of modified histone peptides were incubated with 20 µg GST-GASC1(1-420) in a total volume of 40 µL, for 2 hours. Reaction mixtures were concentrated and re-dissolved in 50% methanol in water with 0.1% formic acid followed by ESI-TOF analysis using ABI Q-Star Pulsar.

Cell Viability Assay

To screen and validate the cellular toxicity of compounds, a cell viability assay was carried out using CellTiter-Glo luminescent cell viability assay kit (Promega, Madison USA). KYSE150 cells were seeded on blank-walled 384-well plates with KYSE medium at densities of 1,000 cells/well. The medium volume for each well was 40 µL. Cells were incubated at 37° C. in 5% $CO_2$/95% air for 24 hours. The medium was removed from each well and replaced with 38 µL, of warmed fresh medium and 2 µL, compound solution in 2% DMSO/98% $H_2O$. The compounds were added into medium at different concentrations with the final concentration of DMSO as 0.1%. After incubation at 37° C. with 5% $CO_2$/95% air for another 48 hours, the plates were equilibrated to room temperature for 30 minutes. 40 µL, of CellTiter-Glo reagent (Promega, Madison USA) was added to each well and mixed for 2 minutes on an orbital shaker. The plate was incubated at room temperature for another 10 minutes to stabilize luminescent signal. The luminescence of each sample was measured in a plate-reading illuminometer (Beckman Coulter DTX 880) with parameters of 1-minute lag time and 0.1 second/well read time. The experiments were performed in triplicate and repeated on two separately initiated cultures.

Biochemical Assays with Fluorescence Detection

The enzyme activity assays for GASC1 and JMJD2A were established on the DELFIA platform. DELFIA assays were performed in white, opaque 384-well plates coated with Streptavidin (Perkin Elmer). GST-GASC1(1-420) was diluted to 200 ng/well in 20 mM Tris HCl pH 8.5/2 mM glutathione and added in a volume of 20 µL. Blank wells received Tris/glutathione buffer only. Test compounds were diluted in DMSO and 100 mL was pinned into the wells. Blank and control wells received only compound buffer. The reactions were initiated by the addition of 500 nM biotin-H3 (1-20)K9me3 substrate, 10 µM $FeSO_4$, 100 µM alpha-ketoglutarate in a volume of 20 µL, and incubated at room temperature for 60 minutes. The plates were washed 3 times with 100 µL of Wash Buffer (50 mM Tris pH 7.4, 150 mM NaCl, 0.05% Tween 20, 0.2% BSA). Next, 50 µL of Fluoroimmunoassay (FI) Buffer (50 mM Tris HCl pH 7.8, 150 mM NaCl, 0.05% Tween 40, 25 µM DTPA, 0.2% BSA, 0.05% BGG) containing 1 ng anti-H3K9me2 and 5 ng goat-anti-rabbit Eu chelate (Perkin Elmer Life Sciences) was added to all wells of the plate, and the plate was incubated for an additional hour at room temperature. The plates were washed 3 times with 100 µL, of Wash Buffer, and 50 µL, of Enhancement Solution (Perkin Elmer Life Sciences) was added to each well. Time resolved fluorescence was measured after 45 minutes on an Envision Microplate Imager (Perkin Elmer Life Sciences) with 400 µs delay, excitation at 360 nm, and emission at 620 nm.

LSD1 activity was measured in a formaldehyde dehydrogenase coupled assay. 15 µL enzyme mix containing 2.4 µg GST-LSD1 in 20 mM TRIS pH 8.5, 1 mM NAD, 1.5 mU formaldehyde dehydrogenase, 0.5 mM glutathione was added, followed by pin transfer of 100 nL compound. Then reactions were started by addition of 15 µL 75 µM H3(1-20) K4me2 peptide, and NADH fluorescence was measured on a Envision Microplate Imager (Perkin Elmer Life Sciences) with excitation at 345 nm and emission at 460 nm, integration for 400 ms at 10 min and 80 min after peptide addition.

Histone Deacetylases (HDACs) Enzyme Inhibition Assay

The enzyme activity assay for HDAC was carried out using Fluor de Lys Fluorescent Assay System (BML-AK500, Enzo Life Sciences Inc, NY USA). The assay was performed as the manufactory guide in white 384-well plates. Time resolved fluorescence was measured on a Beckman Coulter DTX 880 plate reader with 250 ms delay, excitation at 360 nm, and emission at 530 nm.

Immunostaining Assay

HeLa cells were seeded in a 96-well plate at 10,000 cells per well and incubated at 37° C. for 24 hours in modified DMEM media. Cells were transfected with expression constructs comprised of the GASC1(1-420) coding regions with GFP-fusion following the manufacturer's protocol for the Lipofectamine 2000 transfection reagent (Invitrogen). DMSO or methylstat were added 6 hours later. After 48 hours' incubation, cells were washed with cold phosphate buffered saline (PBS) and fixed in 3.7% paraformaldehyde for 20 min. The cells were washed three times with cold PBS buffer and then permeabilized for 10 min with 0.5% Triton-X-100. The samples were blocked with 1% BSA for 30 min followed by incubation with the primary antibodies anti-H3K9me3 (0.2% in PBS) overnight. Following three washes with PBS, the samples were incubated with the secondary antibodies (0.1%, Alexa Fluor 694 anti Rabbit IgG (H+L), Invitrogen) and Hoechest33342 in PBS for 30 min. After washing with PBS, the plates were visualized using a fluorescence microscope (Nikon Eclipse 90i).

For quantified immunostaining experiments, KYSE150 or MCF7 cells were seeded in a 96-well plate at 10,000 cells per well and incubated at 37° C. for 24 hours. The medium was replaced and methylstat in DMSO was added at the concentration as indicated. After incubation for another 48 hours, immunostaining procedure was performed as described above using anti-H3K9me3 or anti-H3K4me3 primary antibody. Fluorescent images of cells were acquired by a Nikon Eclipse 90i fluorescence microscope and analyzed using the Cell Scoring analysis module of MetaMorph 7.0 software.

Preparation of Cell lysates and Histone Extraction

Total lysates of cells were generated from the cells lysed in CelLytic M Cell Lysis (Sigma) with protease inhibitor cocktail (Sigma), mixed with 2×LSB buffer (100 mM Tris-HCl pH 6.8, 200 mM DTT, 4% SDS, 20% glycerol and 0.2% bromophenol blue) and boiled for 5 min before SDS-PAGE. BCA assay (Thermo) was applied for protein qualification.

Histone extraction was generated from the cells lysed in Triton Extraction Buffer (TEB: PBS containing 0.5% Triton X 100 (v/v), 2 mM phenylmethylsulfonyl fluoride (PMSF), 0.02% (w/v) $NaN_3$) at the density of $10^7$ cells/mL. 0.2 N HCl was used to extract histone over night at 4° C.

Synthetic Procedures.

Unless otherwise noted, reagents were obtained commercially and used without further purification. $CH_2Cl_2$ was distilled from $CaH_2$ under a nitrogen atmosphere. TLC analysis of reaction mixtures was performed on Dynamic adsorbents silica gel F-254 TLC plates. Flash chromatography was carried out on Zeoprep 60 ECO silica gel. $^1H$ and $^{13}C$ NMR spectra were recorded with Varian INOVA 400, 500 spectrometers and referenced to $CDCl_3$ or $CD_3OD$. Mass spectral and analytical data were obtained via the PE SCIEX/ABI API QSTAR Pulsar i Hybrid LC/MS/MS, Applied Biosystems operated by the Central Analytical Laboratory, University of Colorado at Boulder. Infrared (IR) spectra were recorded on a Thermo Nicolet Avatar 370 FT-IR spectrometer. Melting point (m.p.) determinations were performed by using a Thomas Hoover capillary melting point apparatus.
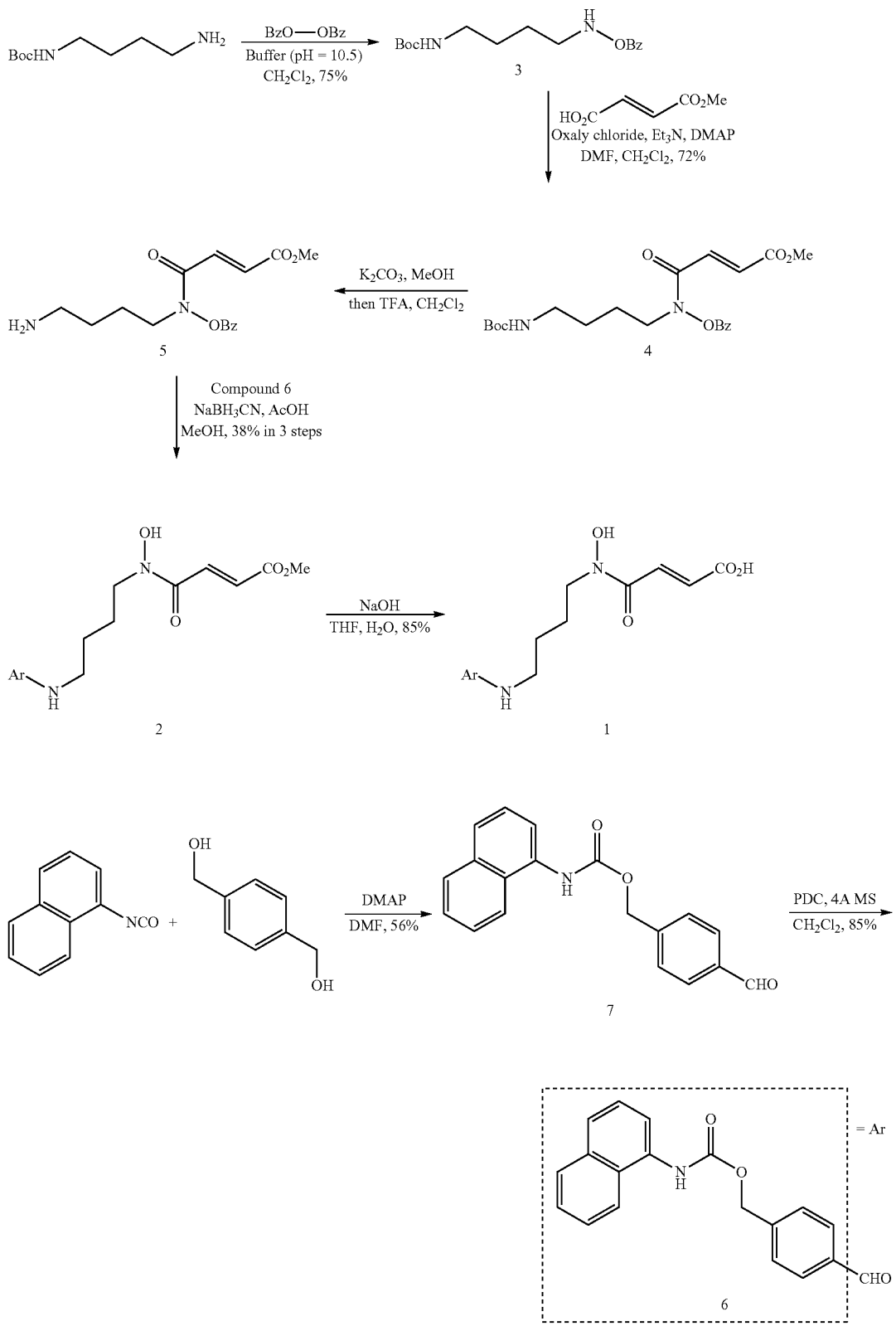

Tert-Butyl 4-(benzoyloxyamino)butylcarbamate (3)

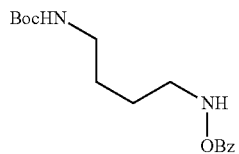

N-Boc-1,4-diaminobutane (0.94 g, 5.0 mmol) was dissolved in CH$_2$Cl$_2$ (20 mL) and diluted with pH 10.5 NaHCO$_3$/NaOH buffer (10 mL). Dibenzoyl peroxide (1.45 g, 6.0 mmol) was added to the biphasic solution, and the reaction mixture was stirred vigorously for 2.5 h. The layers were separated and the aqueous layer was extracted with CH$_2$Cl$_2$. The combined organic layers were washed with 10% aqueous solution of Na$_2$S$_2$O$_3$, dried over anhydrous Na$_2$SO$_4$, filtered, and concentrated in vacuo. The crude material was purified by flash chromatography on silica gel (hexanes/ethyl acetate=5:1) to afford 3 (1.16 g, 3.75 mmol) as a white solid in 75% yield: m.p.: 113-114° C.; IR (thin film): 3327, 2975, 2869, 1693, 1644, 1538, 1252, 1172 cm$^{-1}$; $^1$H NMR (500 MHz, CDCl$_3$): δ 7.79 (d, J=7.4 Hz, 2H), 7.47 (t, J=11.1 Hz, 1H), 7.43-7.38 (m, 2H), 4.81-4.62 (br, 1H), 3.52-3.45 (m, 2H), 3.21-3.15 (m, 2H), 1.78-1.49 (m, 4H), 1.41 (s, 9H) ppm; $^{13}$C NMR (101 MHz, CDCl$_3$): δ 167.80, 156.38, 134.74, 131.46, 128.59, 127.13, 79.34, 40.16, 39.78, 28.55, 27.82, 26.73 ppm. HRMS (m/z): [M+H]$^+$ calcd. for C$_{16}$H$_{25}$N$_2$O$_4$, 309.1809; found, 309.1812.

(E)-Methyl 4-(benzoyloxy(4-(tert-butoxycarbonylamino)butyl)amino)-4-oxobut-2-enoate (4)

Oxalyl chloride (0.39 mL, 4.5 mmol) was added dropwise to a solution of mono-methyl fumarate (0.64 g, 4.9 mmol) in distilled CH$_2$Cl$_2$ (7 mL) at 0° C., then a drop of anhydrous DMF was added. The resulting mixture was stirred at this temperature for 20 minutes before it was warmed to room temperature and stirred for another 30 minutes. A solution of 3 (1.16 g, 3.75 mmol) in distilled CH$_2$Cl$_2$ (3 mL) was added at 0° C., followed by the addition of freshly distilled triethylamine (1.05 mL, 7.5 mmol) and DMAP (0.049 g, 0.40 mmol). The reaction was stirred at room temperature for 2 h. A saturated aqueous solution of NH$_4$Cl was added and the aqueous layer was extracted with ethyl acetate, dried over anhydrous Na$_2$SO$_4$, filtered and concentrated in vacuo to give a crude oil, which was purified by column chromatography on silica gel (hexanes/ethyl acetate=10:1) to afford 4 (1.14 g, 2.7 mmol) as a colorless oil in 72% yield: IR (thin film): 3368, 2976, 1768, 1713, 1520, 1240, 1170, 1006 cm$^{-1}$; $^1$H NMR (400 MHz, CDCl$_3$): δ 8.15-8.03 (m, 2H), 7.68 (t, J=7.5 Hz, 1H), 7.52 (t, J=7.7 Hz, 2H), 7.13 (d, J=15.7 Hz, 1H), 6.92 (d, J=15.4 Hz, 1H), 4.65-4.56 (br, 1H), 3.89 (t, J=6.9 Hz, 2H), 3.73 (s, 3H), 3.18-3.13 (m, 2H), 1.75-1.70 (m, 2H), 1.61-1.52 (m, 2H), 1.39 (s, 9H) ppm; $^{13}$C NMR (101 MHz, CDCl$_3$): δ 165.80, 164.62, 156.15, 135.03, 133.03, 131.28, 130.37, 129.20, 126.24, 79.31, 52.43, 52.39, 48.38, 40.20, 28.54, 27.48, 24.50 ppm. HRMS (m/z): [M+Na]$^+$ calcd. for C$_{21}$H$_{28}$N$_2$NaO$_7$, 443.1788; found, 443.1792.

(E)-Methyl-4-(hydroxy(4-(4-(((naphthalen-1-yl-carbamoyloxy)methyl)benzyl amino)butyl amino)-4-oxobut-2-enoate (2, methylstat)

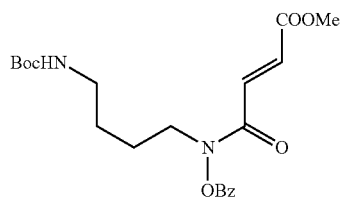

To a solution of 4 (1.14 g, 2.7 mmol) in anhydrous methanol (10 mL) was added potassium carbonate (0.45 g, 3.24 mmol). The resulting mixture was stirred at room temperature for 30 min. A saturated NH$_4$Cl aqueous solution was added and the aqueous layer was extracted with ethyl acetate, dried over Na$_2$SO$_4$, filtered and concentrated in vacuo to give a crude oil, which was dissolved in distilled CH$_2$Cl$_2$ (5 mL) and cooled to 0° C. Trifluoroacetic acid (4.2 mL, 54 mmol) was added to the above solution. The resulting mixture was warmed to room temperature and stirred for 2 h. The solvent was removed in vacuo to give an oil, which was dissolved in distilled CH$_2$Cl$_2$ (5 mL). Triethylamine (1 mL, 7.2 mmol) was added and the solution was stirred for 5 min before the solvents were removed in vacuo to give the crude amine 5. Aldehyde 6 (0.79 g, 2.6 mmol) was added to a solution of amine 5 and acetic acid (0.31 mL, 5.4 mmol) in dry methanol (10 mL). Sodium cyanoborohydride (0.85 g, 13.5 mmol) was added after 20 min and the resulting mixture was stirred at room temperature overnight. Water was added and the mixture extracted with ethyl acetate. The combined organic phase was dried over Na$_2$SO$_4$, filtered and concentrated in vacuo to produce a crude oil, which was purified by column chromatography on silica gel (CH$_2$Cl$_2$/MeOH=20:1) to afford 2 (0.52 g, 1.03 mmol) as a yellowish solid in 38% yield over 3 steps: m.p.: 120-122° C.; IR (thin film): 2952, 2336, 2175, 1721, 1599, 1437, 1260, 1223, 1010 cm$^{-1}$; $^1$H NMR (500 MHz, CDCl$_3$): δ 7.91-7.79 (m, 2H), 7.65 (d, J=8.0 Hz, 1H), 7.56 (d, J=15.7 Hz, 1H), 7.52-7.45 (m, 3H), 7.43-7.39 (m, 2H), 7.36 (s, 3H), 6.60 (d, J=15.7 Hz, 1H), 5.16 (s, 2H), 3.93 (s, 2H), 3.72 (s, 3H), 3.59-3.51 (m, 2H), 2.90-2.80 (m, 2H), 1.68-1.61 (br, 4H) ppm; $^{13}$C NMR (101 MHz, CDCl$_3$): δ 166.32, 164.98, 154.95, 137.87, 134.21, 132.98, 132.49, 131.03, 130.28, 128.77, 126.56, 126.36, 125.85, 121.20, 66.67, 52.47, 52.43, 51.87, 47.72, 29.91, 23.59 ppm. HRMS (m/z): [M+H]$^+$ calcd. for C$_{28}$H$_{32}$N$_3$O$_6$, 506.2286; found, 506.2286.

(E)-4-(Hydroxy(4-4-((naphthalen-1-ylcarbamoyloxy)methyl)benzylamino)butyl)amino)-4-oxobut-2-enoic acid (1)

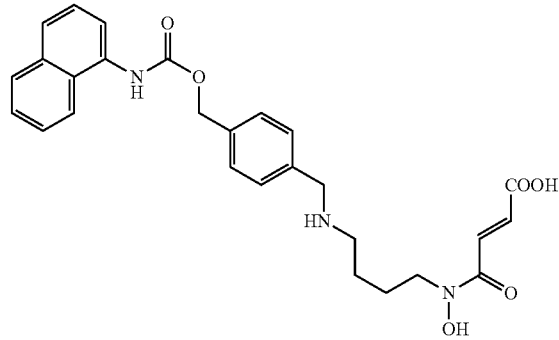

To a solution of 2 (152 mg, 0.3 mmol) in THF was added an aqueous solution of NaOH (1.0 M, 0.6 mL). The resulting mixture was stirred at room temperature for 3 hours before a solution of HCl (4.0 M in 1,4-dioxane, 0.15 mL) was added. The solvents were removed in vacuo to give a crude solid, which was purified by column chromatography on silica gel ($CH_2Cl_2$/MeOH=10:1) to give 1 (124 mg, 0.254 mmol) as a yellowish solid in 85% yield: m.p.: 178-180° C. (dec.); IR (thin film): 3399, 2927, 1705, 1565, 1390, 1222, 1103 cm$^{-1}$; $^1$H NMR (400 MHz, $CD_3OD$): δ 8.05-7.94 (m, 1H), 7.91-7.82 (m, 1H), 7.71 (d, J=8.3 Hz, 1H), 7.61 (br, 1H), 7.57-7.32 (m, 8H), 6.80 (d, J=15.7 Hz, 1H), 5.21 (s, 2H), 3.74 (s, 2H), 3.70 (t, J=7.0 Hz, 2H), 2.60 (t, J=7.3 Hz, 2H), 1.75-1.65 (m, 2H), 1.60-1.50 (m, 2H) ppm; $^{13}$C NMR (101 MHz, $CD_3OD$): δ 174.40, 166.24, 157.54, 140.50, 139.46, 137.14, 135.78, 134.70, 129.91, 129.38, 129.10, 127.24, 127.21, 126.83, 126.66, 123.37, 122.64, 67.80, 54.09, 30.88, 27.54, 25.58 ppm. HRMS (m/z): [M+Na]$^+$ calcd. for $C_{27}H_{29}N_3NaO_6$, 514.1948; found, 514.1952.

4-(Hydroxymethyl)benzyl naphthalen-1-ylcarbamate (7)

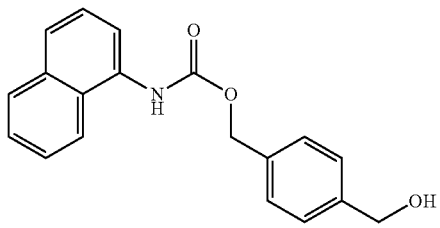

To a solution of 1-isocyanatonaphthalene (1.69 g, 10 mmol) and 1,4-phenylene-dimethanol (4.14 g, 30 mmol) in anhydrous DMF was added DMAP (0.06 g, 0.5 mmol). The resulting mixture was stirred at room temperature for 12 h. The solvent was removed in vacuo to give a solid, which was recrystallized using ethyl acetate to produce 7 (1.72 g, 5.6 mmol) as a white solid in 56% yield: m.p.: 158-159° C.; IR (thin film): 3325, 1691, 1542, 1420, 1245, 1237 cm$^{-1}$; $^1$H NMR (500 MHz, $CDCl_3$): δ $^1$H NMR (500 MHz, $CDCl_3$) δ 7.95-7.83 (m, 3H), 7.68 (d, J=8.2 Hz, 1H), 7.58-7.47 (m, 4H), 7.44-7.35 (m, 3H), 5.27 (s, 2H), 4.73 (d, J=5.8 Hz, 2H), 1.70 (t, J=6.0 Hz, 1H) ppm; $^{13}$C NMR (75 MHz, $CDCl_3$): δ 154.43, 141.33, 140.53, 136.51, 135.70, 134.28, 132.55, 128.98, 128.90, 127.44, 127.41, 126.49, 126.24, 126.02, 125.35, 120.61, 67.25, 65.24 ppm. HRMS (m/z): [M+Na]$^+$ calcd. for $C_{19}H_{17}NNaO_3$, 330.1100; found, 330.1095.

4-Formylbenzyl naphthalen-1-ylcarbamate (6)

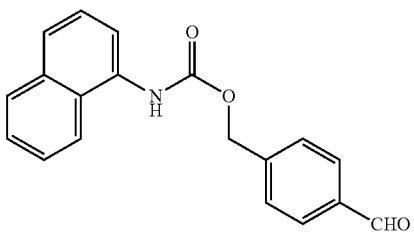

PDC (2.1 g, 5.6 mmol) was added to a stirred mixture of alcohol 7 (1.72 g, 5.6 mmol) and activated 4 Å molecular sieves (1.0 g) in anhydrous dichloromethane (20 mL). The resulting mixture was stirred for 5 h; then it was diluted with diethyl ether (20 mL). The resulting suspension was filtrated through a pad of silica gel. The solvent was removed in vacuo and the residue was purified by column chromatography on silica gel (hexanes/ethyl acetate=5:1) to provide aldehyde 6 (1.46 g, 4.8 mmol) as a white solid in 85% yield: m.p.: 153-154° C.; IR (thin film): 3272, 1691, 1609, 1544, 1504, 1257, 1206 cm$^{-1}$; $^1$H NMR (500 MHz, $CDCl_3$): δ 10.01 (s, 1H), 7.93-7.81 (m, 5H), 7.68 (d, J=8.2 Hz, 1H), 7.57 (s, 1H), 7.55-7.40 (m, 4H), 5.32 (s, 2H) ppm; $^{13}$C NMR (101 MHz, $CDCl_3$): δ 192.07, 192.03, 154.26, 143.05, 136.09, 134.16, 132.34, 130.94, 130.08, 128.82, 128.28, 126.74, 126.41, 126.20, 125.83, 125.47, 120.68, 119.36, 66.35 ppm. HRMS (m/z): [M+Na]$^+$ calcd. for $C_{19}H_{15}NNaO_3$, 328.0944; found, 328.0938.

General procedures I-V

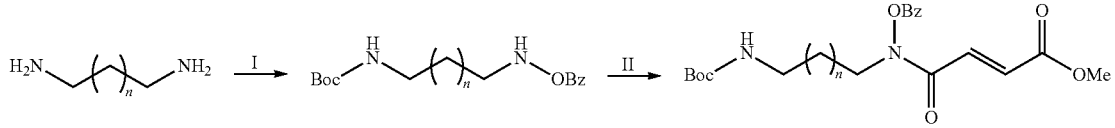

n = 1, 3, 4, 5, 6

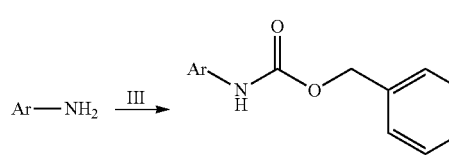
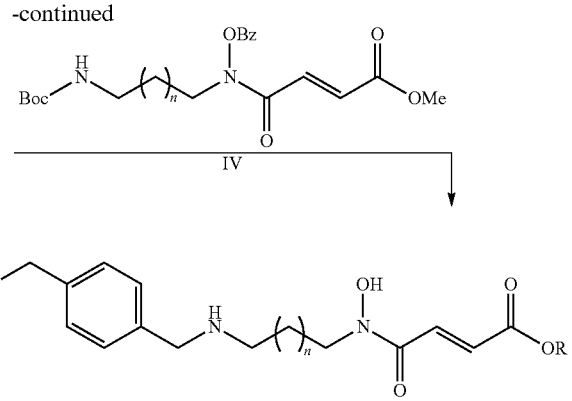

General Procedure I:

To diamine (20 mmol) in 30 ml CH$_2$Cl$_2$ at 0° C. was added di-tert-butyl dicarbonate (4 mmol) in 20 ml CH$_2$Cl$_2$ dropwise via a pressure equalizing addition funnel in 2 h. The reaction mixture was stirred at 25° C. for 12 h before concentration. The solid was dissolved in ethyl acetate, washed with half-saturated brine 3 times, dried over sodium sulfate, filtered and concentrated to give 4 mmol mono-protected amine. Benzoyl peroxide (10 mmol) was added portionwise to a vigorously stirred mixture of mono-protected amine in 10 ml carbonate buffer solution (pH 10.5) and 10 ml CH$_2$Cl$_2$ at 25° C. After 4 h, aqueous layer was extracted with CH$_2$Cl$_2$ 3 times. The combined organic phases were dried over sodium sulfate and concentrated in vacuum. The residue was purified by flash chromatography over silica gel.

General Procedure II:

To methyl hydrogen fumarate (0.398 g, 3.06 mmol) in 4 ml CH$_2$Cl$_2$ at 0° C. was added oxalyl chloride (0.262 ml, 3.06 mmol) and one drop of DMF. The solution was stirred at 25° C. for 1.5 h before concentration in vacuum. To oxidized amine (1.53 mmol) and 4-(dimethylamino)pyridine (0.093 g, 0.764 mmol) in 4 ml CH$_2$Cl$_2$ at 0° C. were added fresh prepared acyl chloride in 3 ml CH$_2$Cl$_2$ followed by triethylamine (1.06 ml, 7.64 mmol). The reaction mixture was stirred at 25° C. for 2 h before addition of saturated NH$_4$Cl. Aqueous layer was extracted with ethyl acetate 3 times, then the combined organic phases were washed with brine, dried over sodium sulfate, filtered and concentrated. The residue was purified by silica gel chromatography.

General Procedure III:

To amine (0.69 mmol) in 3.5 ml anhydrous dioxane was added triphosgene (0.068 g, 0.23 mmol) and the resulting mixture was stirred at 70° C. for 5 h before concentration. The solid residue was dissolved in 3.5 ml dimethylformamide, to which 4-(hydroxylmethyl)benzaldhyde (0.066 g, 0.49 mmol), triethylamine (0.19 ml, 1.39 mmol) and 4-(dimethylamino)pyridine were added. The reaction mixture was stirred at 25° C. for 12 h before concentration. The solid was dissolved in ethyl acetate and the organic phase was washed with water (5 times), brine, dried over sodium sulfate, filtered and concentrated. The residue was purified by silica gel chromatography.

General Procedure IV:

To benzoyl-protected hydroxylamine (0.765 mmol) in 4 ml methanol 25° C. was added potassium carbonate (0.212 g, 1.53 mmol). The mixture was stirred for 2 h before addition of saturated NH$_4$Cl. The aqueous phase was extracted with ethyl acetate 3 times, and then the combined organic phases were washed with brine, dried over sodium sulfate, filtered and concentrated. To the residue in 2 ml CH$_2$Cl$_2$ was added trifluoroacetic acid (1.17 ml, 15.28 mmol) dropwise at 0° C. The resulting solution was stirred at 0° C. for 10 min before concentrated to afford a reddish oil. The oil was dissolved in 4 ml methanol, to which were added triethylamine (0.21 ml, 1.53 mmol), aldehyde (0.918 mmol) and acetic acid (0.13 ml, 2.30 mmol). After stirring for 30 min, sodium cyanoborohydride (0.24 g, 3.83 mmol) was added in one portion. The mixture was stirred for 12 h before concentration. Water was added and aqueous phase was extracted with ethyl acetate 3 times. The combined organic phases were washed with saturated NaHCO$_3$ and brine, dried over sodium sulfate, filtered and concentrated. The residue was purified by silica gel chromatography.

General Procedure V:

To ester (0.17 mmol) in 1 ml tetrahydrofuran was added LiOH monohydrate (71 mg, 1.69 mmol) in 1 ml water. After 2 h, 4 M HCl in dioxane (0.42 ml, 1.69 mmol) was added. After 5 min, the solution was concentrated and the residue was purified by reverse phase chromatography.

Compound Characterization:

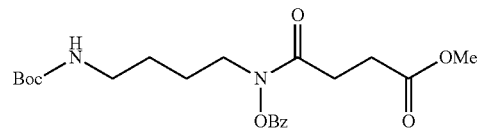

101

A mixture of benzoyl-protected hydroxylamine (0.462 g, 1.5 mmol), succinic anhydride (0.3 g, 3 mmol) and sodium carbonate (0.318 g, 3 mmol) in 3 ml tetrahydrofuran was stirred at 50° C. for 1 h. Then the mixture was acidified with 2 M HCl and extracted with ethyl acetate, the combined organic layer was dried over anhydrous Na$_2$SO$_4$. The solvent was removed and the crude material was dissolved in 1.5 ml tetrahydrofuran and 1.5 ml methanol. 2.0 M (trimethylsilyl)diazomethane solution in diethyl ether (1.12 ml, 2.24 mmol) was added dropwise and the mixture was stirred at 25° C. for 1 h. The solvent was removed under reduce pressure and the residue was purified by flash chromatography over silica gel (hexanes/ethyl acetate, 2:1) to afford product (0.86 g, 68%). $^1$H NMR (500 MHz, CDCl$_3$) δ 8.10 (dd, J=8.4 Hz, 1.2 Hz, 2H), 7.68 (t, J=7.5 Hz, 1H), 7.53 (t, J=7.8 Hz, 2H), 4.61 (s, 1H), 3.84 (t, J=6.9 Hz, 2H), 3.68 (s, 3H), 3.14 (dd, J=12.7 Hz, 6.2 Hz, 2H), 2.64 (s, 4H), 1.71-1.63 (m, 2H), 1.61-1.52 (m, 2H), 1.41 (s, 9H). $^{13}$C NMR (100 MHz, CDCl$_3$) δ 172.37, 171.48, 171.42, 163.81, 155.53, 134.04, 129.41, 128.38, 125.98, 78.01, 76.65, 51.10, 47.24, 39.36, 27.78, 27.66, 26.53, 23.69. HRESIMS m/z calcd for C$_{21}$H$_{30}$N$_2$O$_{27}$ [M+Na]$^+$ 445.1946, found 445.1946.

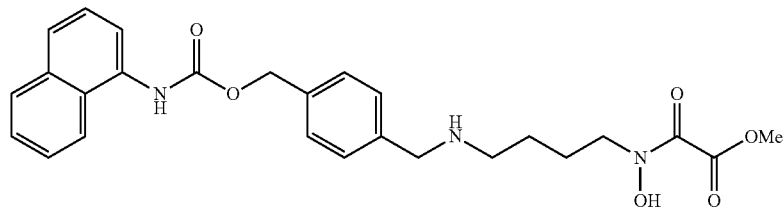

102

Following general procedure IV gave 45% yield of product. ¹H NMR (400 MHz, CD₃OD) δ 8.04-7.97 (m, 1H), 7.91-7.83 (m, 1H), 7.72 (d, J=8.2 Hz, 1H), 7.61 (d, J=7.3 Hz, 1H), 7.56-7.41 (m, 8H), 5.25 (s, 2H), 4.15 (s, 2H), 3.71-3.54 (m, 5H), 3.03 (t, J=7.3 Hz, 2H), 2.78 (t, 6.5 Hz, 2H), 2.58 (t, 6.5 Hz, 2H), 1.68 (bs, 4H). ¹³C NMR (101 MHz, CD₃OD) δ 175.14, 173.99, 157.24, 139.94, 137.17, 135.60, 134.55, 134.45, 129.79, 129.29, 129.24, 127.05, 126.63, 126.52, 123.17, 123.10, 122.48, 67.59, 53.86, 52.14, 48.65, 29.34, 28.23, 27.00, 25.27. HRESIMS m/z calcd for $C_{28}H_{33}N_3O_6$ [M+H]⁺ 508.2448, found 508.2448.

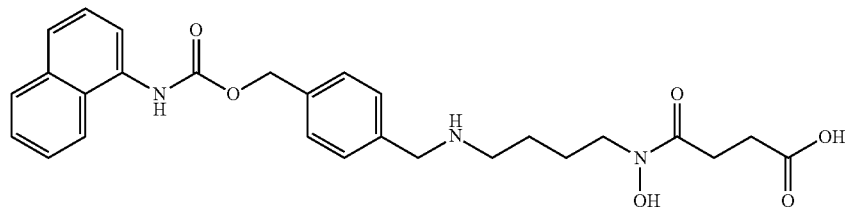

103

Following general procedure V gave 86% yield of product. ¹H NMR (400 MHz, CD₃OD) δ 8.05-7.98 (m, 1H), 7.89-7.83 (m, 1H), 7.71 (d, J=8.2 Hz, 1H), 7.65-7.39 (m, 8H), 5.24 (s, 2H), 4.18 (s, 2H), 3.64 (br s, 2H), 3.02 (br s, 2H), 2.73 (br s, 2H), 2.51 (br s, 3H), 1.70 (br s, 4H). ¹³C NMR (101 MHz, CD₃OD) δ 157.21, 139.53, 135.58, 134.41, 132.48, 131.33, 129.40, 129.28, 127.15, 127.10, 126.80, 126.76, 126.50, 123.19, 122.51, 67.19, 51.85, 48.15, 47.66, 33.16, 29.46, 24.62, 24.01. HRESIMS m/z calcd for $C_{27}H_{31}N_3O_6$ [M+H]⁺ 495.2318, found 495.2320.

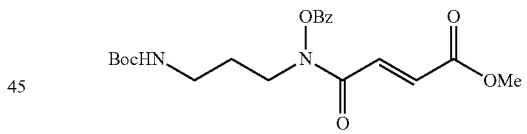

104

Following general procedure II gave 92% yield of product. ¹H NMR (500 MHz, CDCl₃) δ 8.12-8.06 (m, 2H), 7.76-7.65 (m, 1H), 7.58-7.50 (m, 2H), 7.14 (d, J=15.4 Hz, 1H), 6.94 (d, J=15.4 Hz, 1H), 5.03 (s, 1H), 3.96 (t, J=6.6 Hz, 2H), 3.75 (s, 3H), 3.30-3.13 (m, 1H), 1.85 (p, J=6.5 Hz, 2H), 1.43 (s, 9H). ¹³C NMR (101 MHz, CDCl₃) δ 165.07, 164.12, 155.66, 134.56, 132.53, 130.51, 129.80, 128.68, 125.55, 78.60, 51.81, 45.74, 37.07, 27.99, 26.97. HRESIMS m/z calcd for $C_{20}H_{26}N_2O_7$ [M+Na]⁺ 429.1633, found 429.1635

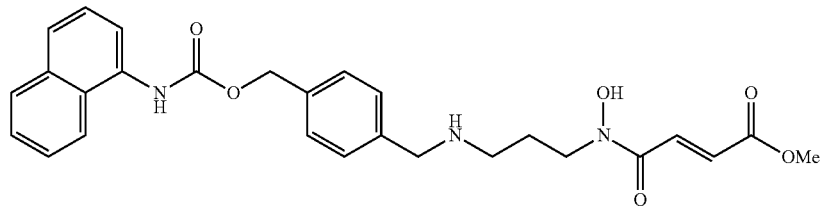

105

Following general procedure IV gave 27% yield of product. ¹H NMR (400 MHz, CD₃OD) δ 8.06-7.95 (m, 1H), 7.89-7.79 (m, 1H), 7.76-7.65 (m, 2H), 7.66-7.59 (m, 1H), 7.51-7.36 (m, 5H), 7.33-7.28 (m, 2H), 6.69 (d, J=15.7 Hz, 1H), 5.20 (s, 2H), 3.77 (t, J=5.6 Hz, 2H), 3.74 (s, 2H), 3.73 (s, 3H), 2.68 (t, J=6.0 Hz, 2H), 1.87-1.73 (m, 2H). ¹³C NMR (101 MHz, CD₃OD) δ 167.53, 164.52, 157.18, 138.11, 137.73, 135.59, 134.53, 134.45, 130.93, 129.97, 129.33, 129.30, 127.09, 127.06, 126.62, 126.53, 123.17, 122.37, 67.47, 53.02, 52.61, 49.85, 47.38, 27.60. HRESIMS m/z calcd for $C_{27}H_{29}N_3O_6$ [M+H]⁺ 492.2130, found 492.2133.

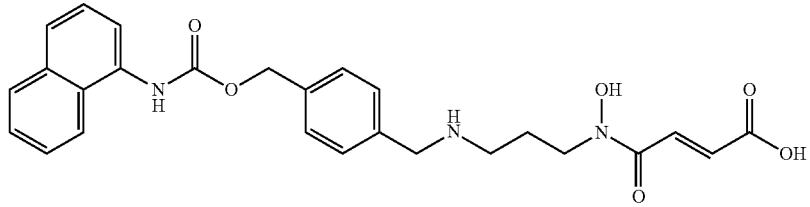

106

Following general procedure V gave 77% yield of product. ¹H NMR (400 MHz, CD₃OD) δ 8.05-7.96 (m, 1H), 7.90-7.82 (m, 1H), 7.75-7.67 (m, 2H), 7.64-7.40 (m, 7H), 7.36 (d, J=15.6 Hz, 1H), 6.85 (d, J=15.3 Hz, 1H), 5.24 (s, 2H), 4.17 (s, 2H), 3.81 (t, J=6.3 Hz, 2H), 3.05 (t, J=7.9 Hz, 2H), 2.11 (p, J=5.8 Hz, 3H). ¹³C NMR (75 MHz, CD₃OD) δ 173.87, 167.24, 157.39, 140.41, 138.81, 137.55, 135.67, 134.60, 130.01, 129.81, 129.37, 129.28, 128.24, 127.11, 127.07, 126.72, 126.52, 123.26, 122.57, 67.58, 54.81, 53.46, 47.33, 27.66. HRESIMS m/z calcd for $C_{26}H_{27}N_3O_6$ [M+H]⁺ 478.1973, found 478.1970

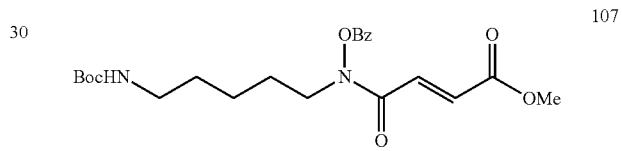

107

Following general procedure II gave 57% yield of product. ¹H NMR (400 MHz, CDCl₃) δ 8.10-8.00 (m, 2H), 7.64 (t, J=7.6 Hz, 1H), 7.48 (t, J=7.6 Hz, 2H), 7.10 (d, J=15.3 Hz, 1H), 6.87 (d, J=15.3 Hz, 1H), 4.72 (s, 1H), 3.83 (t, J=7.0 Hz, 2H), 3.67 (s, 3H), 3.04 (q, J=6.7 Hz, 2H), 1.65 (p, J=7.4 Hz, 2H), 1.45 (p, J=7.4 Hz, 2H), 1.41-1.27 (m, 11H). ¹³C NMR (101 MHz, CDCl₃) δ 165.36, 164.22, 164.15, 155.80, 134.61, 132.53, 130.93, 129.93, 128.81, 125.86, 78.70, 51.97, 47.98, 40.00, 29.32, 28.16, 26.38, 23.53. HRESIMS m/z calcd for $C_{22}H_{30}N_2O_7$ [M+Na]⁺ 457.1946, found 457.1947.

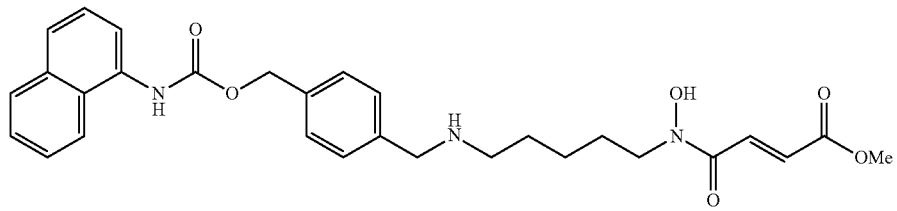

108

Following general procedure IV gave 36% yield of product. ¹H NMR (400 MHz, CD₃OD) δ 8.05-7.95 (m, 1H), 7.90-7.82 (m, 1H), 7.75-7.65 (m, 2H), 7.62 (d, J=7.4 Hz, 1H), 7.53-7.32 (m, 7H), 6.71 (d, J=15.7 Hz, 1H), 5.22 (s, 2H), 3.81 (s, 2H), 3.76 (s, 3H), 3.68 (t, J=6.8 Hz, 2H), 2.63 (d, J=7.6 Hz, 2H), 1.67 (p, J=7.3 Hz, 2H), 1.58 (p, J=7.7 Hz, 2H), 1.41-1.22 (m, 2H). ¹³C NMR (101 MHz, CD₃OD) δ 167.49, 165.03, 157.28, 138.62, 137.68, 135.65, 134.55, 134.32, 131.17, 130.04, 129.45, 129.31, 129.19, 127.09, 127.07, 126.69, 126.53, 123.19, 122.40, 67.54, 53.53, 52.60, 49.84, 49.32, 29.08, 27.25, 25.12. HRESIMS m/z calcd for $C_{29}H_{33}N_3O_6$ [M+H]⁺ 520.2443, found 520.2447.

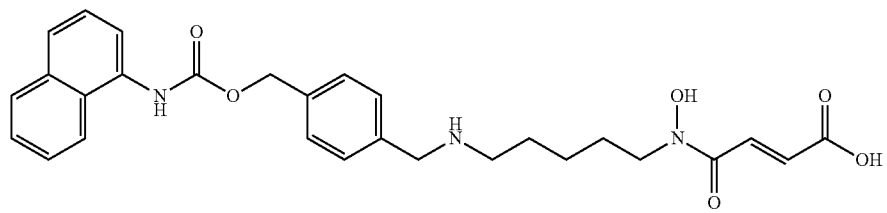

109

Following general procedure V gave 96% yield of product. ¹H NMR (400 MHz, CD₃OD) δ 8.07-7.97 (m, 1H), 7.92-7.82 (m, 1H), 7.72 (d, J=8.2 Hz, 1H), 7.66-7.42 (m, 8H), 7.38 (d, J=15.6 Hz, 1H), 6.84 (d, J=12.8 Hz, 1H), 5.26 (s, 2H), 4.20 (s, 2H), 3.71 (t, J=6.2 Hz, 2H), 3.02 (t, J=8.0 Hz, 2H), 1.89-1.61 (m, 4H), 1.52-1.34 (m, 2H). ¹³C NMR (101 MHz, CD₃OD) δ 157.24, 153.24, 151.29, 139.79, 135.66, 134.50, 134.14, 132.45, 131.27, 129.77, 129.53, 129.32, 128.58, 127.13, 126.75, 126.52, 124.08, 123.20, 122.07, 67.19, 54.82, 51.89, 48.47, 27.06, 26.63, 24.56. HRESIMS m/z calcd for $C_{28}H_{31}N_3O_6$ [M+H]⁺ 506.2286, found 506.2288.

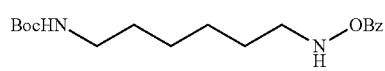

110

Following general procedure I gave 47% yield of product. ¹H NMR (500 MHz, CDCl₃) δ 8.02 (dd, J=8.2, 1.4 Hz, 2H), 7.60 (td, J=7.7, 1.9 Hz, 1H), 7.47 (t, J=7.8 Hz, 2H), 4.51 (br s, 1H), 3.18 (t, J=7.2 Hz, 2H), 3.14-3.02 m, 2H), 1.67 (p, J=7.2 Hz, 2H), 1.55-1.30 (m, 17H). HRESIMS m/z calcd for $C_{18}H_{28}N_2O_4$ [M+Na]⁺ 359.1942, found 359.1944.

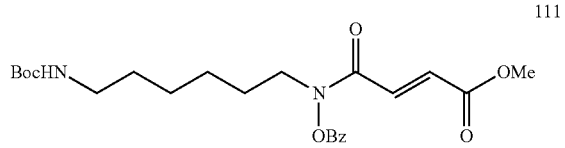

111

Following general procedure II gave 47% yield of product ¹H NMR (500 MHz, CDCl₃) δ 8.13-8.07 (m, 2H), 7.70 (t, J=7.5 Hz, 1H), 7.54 (t, J=7.5 Hz, 2H), 7.15 (d, J=15.5 Hz, 1H), 6.94 (d, J=15.5 Hz, 1H), 4.52 (s, 1H), 3.88 (t, J=7.1 Hz, 2H), 3.75 (s, 3H), 3.09 (q, J=6.2 Hz, 2H), 1.69 (p, J=7.4 Hz, 2H), 1.53-1.45 (m, 2H), 1.43 (s, 9H), 1.43-1.28 (m, 4H). HRESIMS m/z calcd for $C_{23}H_{32}N_2O_7$ [M+Na]⁺ 471.2102, found 471.2105.

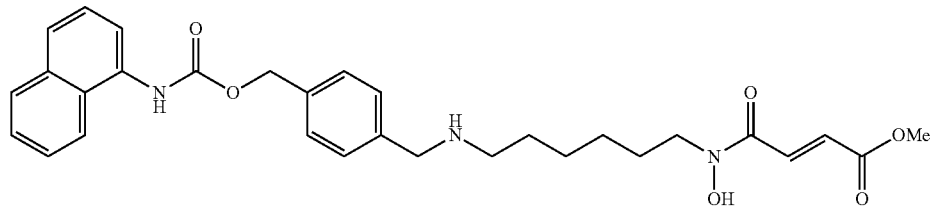

112

Following general procedure IV gave 73% yield of product ¹H NMR (300 MHz, CD₃OD) δ 8.07-7.95 (m, 1H), 7.92-7.83 (m, 1H), 7.72 (d, J=8.2 Hz, 1H), 7.65 (d, J=15.7 Hz, 1H), 7.61-7.41 (m, 7H), 6.73 (dd, J=15.6, 0.9 Hz, 1H), 5.27 (s, 2H), 4.19 (d, J=2.1 Hz, 2H), 3.79 (d, J=1.2 Hz, 3H), 3.70 (t, J=6.8 Hz, 2H), 3.02 (t, J=7.7 Hz, 2H), 1.78-1.60 (m, 4H), 1.50-1.30 (m, 4H). ¹³C NMR (75 MHz, CD₃OD) δ 167.30, 165.60, 157.13, 139.77, 135.57, 134.39, 133.93, 132.21, 132.17, 131.65, 131.10, 129.50, 129.31, 127.16, 127.12, 126.80, 126.50, 123.11, 122.50, 67.15, 52.68, 51.93, 48.49, 47.88, 27.16, 26.92, 26.89. HRESIMS m/z calcd for $C_{30}H_{35}N_3O_6$ [M+H]⁺ 534.2599, found 534.2607.

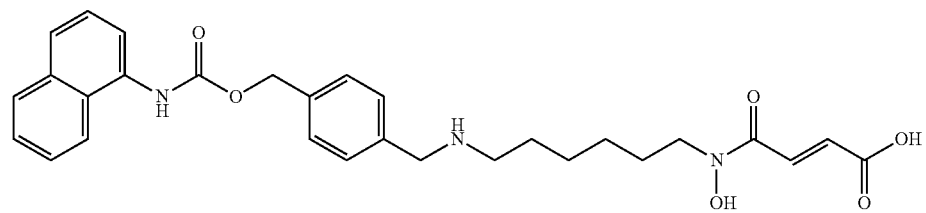

113

Following general procedure V gave 70% yield of product. $^1$H NMR (300 MHz, CD$_3$OD) δ 8.07-7.97 (m, 1H), 7.94-7.84 (m, 1H), 7.73 (d, J=8.1 Hz, 1H), 7.66-7.40 (m, 9H), 6.78 (d, J=15.8 Hz, 1H), 5.27 (s, 2H), 4.21 (s, 2H), 3.70 (t, J=6.6 Hz, 2H), 3.03 (t, J=7.9 Hz, 2H), 1.82-1.59 (m, 4H), 1.50-1.25 (m, 4H). $^{13}$C NMR (75 MHz, CD$_3$OD) δ 172.97, 166.84, 157.21, 139.86, 135.67, 134.50, 132.37, 132.33, 131.22, 131.11, 129.61, 129.55, 129.33, 127.15, 127.11, 126.81, 126.52, 123.18, 122.57, 67.18, 61.53, 51.92, 48.48, 27.23, 27.00, 26.96, 26.91. HRESIMS m/z calcd for C$_{29}$H$_{33}$N$_3$O$_6$ [M+H]$^+$ 520.2443, found 520.2451.

114

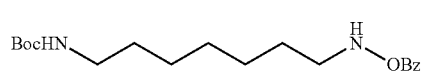

Following general procedure I gave 67% yield of product. $^1$H NMR (500 MHz, CDCl$_3$) δ 8.02 (dd, J=8.4, 1.4 Hz, 2H), 7.59 (td, J=7.3, 1.4 Hz, 1H), 7.50-7.43 (m, 2H), 4.49 (s, 1H), 3.15 (t, J=7.2 Hz, 2H), 3.13-3.05 (m, 2H), 1.63 (p, J=7.2 Hz, 2H), 1.51-1.27 (m, 17H). $^{13}$C NMR (75 MHz, CDCl$_3$) δ 165.65, 155.23, 132.35, 128.31, 127.66, 127.61, 77.40, 51.43, 39.58, 29.11, 28.22, 27.55, 26.20, 26.08, 25.80.

115

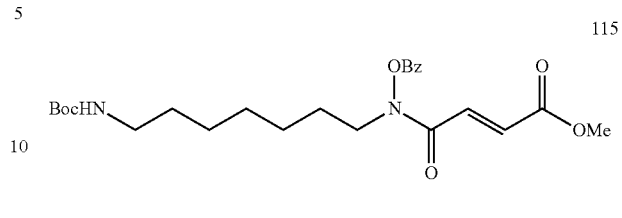

Following general procedure II gave 54% yield of product. $^1$H NMR (500 MHz, CDCl$_3$) δ 8.10 (dd, J=8.4, 1.4 Hz, 2H), 7.70 (t, J=7.5 Hz, 1H), 7.54 (t, J=7.7 Hz, 2H), 7.16 (d, J=15.4 Hz, 1H), 6.94 (d, J=15.4 Hz, 1H), 4.50 (s, 1H), 3.88 (t, J=7.0 Hz, 2H), 3.75 (s, 3H), 3.09 (q, J=6.9 Hz, 2H), 1.73-1.62 (m, 2H), 1.49-1.23 (m, 17H). $^{13}$C NMR (101 MHz, CDCl$_3$) δ 165.11, 163.94, 155.74, 155.72, 134.47, 132.23, 130.91, 129.73, 128.68, 125.80, 78.17, 51.76, 47.96, 40.05, 29.54, 28.44, 28.04, 26.52, 26.23, 26.16. HRESIMS m/z calcd for C$_{24}$H$_{34}$N$_2$O$_7$ [M+Na]$^+$ 485.2259, found 485.2260.

116

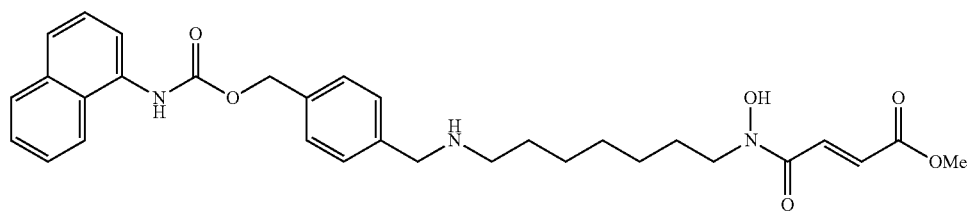

Following general procedure IV gave 42% yield of product. $^1$H NMR (300 MHz, CD$_3$OD) δ 8.06-7.96 (m, 1H), 7.93-7.84 (m, 1H), 7.73 (d, J=8.2 Hz, 1H), 7.65 (d, J=15.7 Hz, 1H), 7.61-7.40 (m, 7H), 6.72 (d, J=15.7 Hz, 1H), 5.28 (s, 2H), 4.19 (s, 2H), 3.79 (s, 3H), 3.70 (t, J=6.9 Hz, 2H), 3.09-2.92 (m, 2H), 1.80-1.57 (m, 4H), 1.50-1.21 (m, 6H). $^{13}$C NMR (75 MHz, CD$_3$OD) δ 167.32, 165.54, 157.13, 139.73, 135.58, 134.40, 133.99, 132.38, 132.02, 131.60, 131.07, 129.50, 129.31, 127.15, 127.11, 126.79, 126.50, 123.11, 122.46, 67.16, 52.67, 51.98, 49.20, 48.61, 29.51, 27.33, 27.29, 27.20, 26.97. HRESIMS m/z calcd for C$_{31}$H$_{37}$N$_3$O$_6$ [M+H]$^+$ 548.2756, found 548.2762.

117

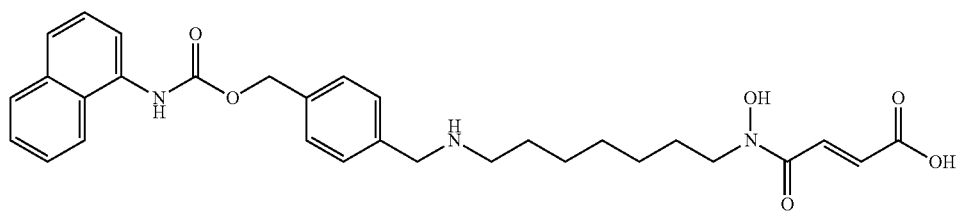

Following general procedure V gave 92% yield of product. ¹H NMR (300 MHz, CD₃OD) δ 8.06-7.96 (m, 1H), 7.92-7.83 (m, 1H), 7.72 (d, J=8.1 Hz, 1H), 7.65-7.40 (m, 9H), 6.74 (d, J=15.4 Hz, 1H), 5.27 (s, 2H), 4.20 (s, 2H), 3.69 (t, J=6.8 Hz, 2H), 3.02 (dd, J=9.3, 6.6 Hz, 2H), 1.78-1.59 (m, 4H), 1.45-1.26 (m, 6H). ¹³C NMR (75 MHz, CD₃OD) δ 166.45, 157.30, 157.22, 139.90, 135.67, 134.50, 132.35, 132.32, 131.21, 129.80, 129.62, 129.57, 129.34, 127.14, 127.11, 126.82, 126.52, 123.18, 122.56, 67.18, 51.94, 49.13, 48.59, 29.54, 27.40, 27.35, 27.22, 26.94. HRESIMS m/z calcd for $C_{30}H_{35}N_3O_6$ [M+H]⁺ 534.2599, found 534.2609

1H), 6.94 (d, J=15.4 Hz, 1H), 4.49 (s, 1H), 3.87 (t, J=7.2 Hz, 2H), 3.75 (s, 3H), 3.09 (q, J=6.8 Hz, 2H), 1.68 (p, J=7.3 Hz, 2H), 1.50-1.19 (m, 19H). ¹³C NMR (75 MHz, CDCl₃) δ 165.35, 164.15, 155.85, 134.59, 132.41, 131.12, 129.92, 128.83, 126.03, 78.49, 51.95, 48.29, 40.33, 29.79, 28.89, 28.86, 28.23, 26.77, 26.46, 26.33.

120

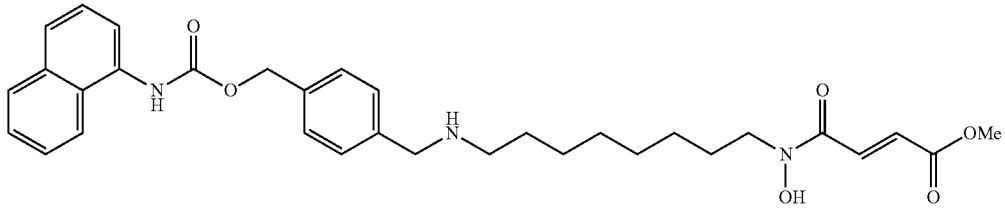

Following general procedure IV gave 45% yield of product. ¹H NMR (300 MHz, CD₃OD) δ 8.08-7.95 (m, 1H), 7.93-7.82 (m, 1H), 7.72 (dd, J=8.9, 3.4 Hz, 1H), 7.65 (d, J=15.7 Hz, 1H), 7.61-7.39 (m, 7H), 6.73 (d, J=15.7 Hz, 1H), 5.28 (s, 2H), 4.19 (s, 2H), 3.79 (s, 3H), 3.69 (t, J=6.9 Hz, 2H), 3.06-2.94 (m, 2H), 1.68 (p, J=6.5 Hz, 4H), 1.48-1.23 (m, 8H). ¹³C NMR (75 MHz, CD₃OD) δ 167.33, 165.53, 157.13, 139.75, 135.59, 134.41, 134.01, 132.39, 131.59, 131.07, 129.51, 129.48, 129.31, 127.14, 127.11, 126.79, 126.50, 123.11, 122.45, 67.16, 52.67, 51.98, 48.65, 29.89, 29.83, 27.38, 27.35, 27.34, 27.05. HRESIMS m/z calcd for $C_{32}H_{39}N_3O_6$ [M+H]⁺ 562.2912, found 562.2918.

118

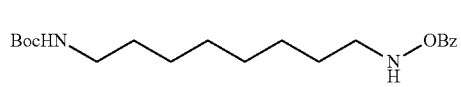

121

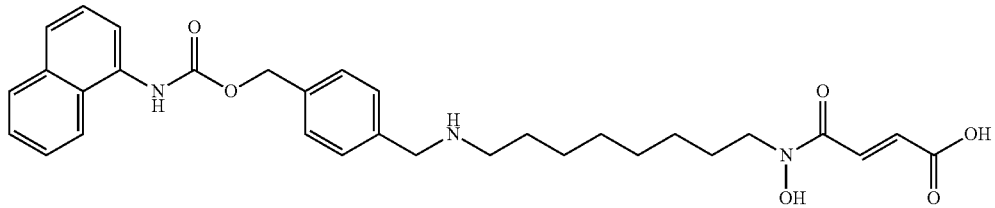

Following general procedure I gave 58% yield of product. ¹H NMR (500 MHz, CDCl₃) δ 8.02 (dd, J=8.3, 1.4 Hz, 2H), 7.62-7.57 (m, 1H), 7.46 (t, J=7.8 Hz, 2H), 4.49 (s, 1H), 3.16 (t, J=7.2 Hz, 2H), 3.10 (q, J=7.0, 6.5 Hz, 2H), 1.63 (p, J=7.2 Hz, 2H), 1.50-1.22 (m, 19H). ¹³C NMR (101 MHz, CDCl₃) δ 168.44, 157.69, 134.93, 130.92, 130.14, 130.08, 80.38, 54.10, 42.18, 31.66, 30.96, 30.79, 30.08, 28.75, 28.57, 28.35. HRESIMS m/z calcd for $C_{20}H_{32}N_2O_4$ [M+Na]⁺ 387.2255, found 387.2253.

Following general procedure V gave 88% yield of product. ¹H NMR (300 MHz, CD₃OD) δ 8.07-7.96 (m, 1H), 7.91-7.83 (m, 1H), 7.73 (d, J=8.1 Hz, 1H), 7.67-7.40 (m, 9H), 6.73 (d, J=15.7 Hz, 1H), 5.27 (s, 2H), 4.20 (s, 2H), 3.68 (t, J=6.9 Hz, 2H), 3.01 (t, J=7.8 Hz, 2H), 1.79-1.57 (m, 4H), 1.45-1.24 (m, 8H). ¹³C NMR (75 MHz, CD₃OD) δ 169.91, 166.40, 157.21, 139.95, 135.69, 134.77, 134.50, 132.36, 132.29, 131.18, 129.65, 129.60, 129.35, 127.14, 127.11, 126.83, 126.52, 123.17, 122.58, 67.17, 51.96, 49.18, 48.64, 29.92, 29.80, 27.41, 27.38, 27.36, 27.02. HRESIMS m/z calcd for $C_{31}H_{37}N_3O_6$ [M+H]⁺ 548.2756, found 548.2768.

119

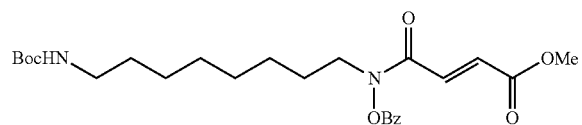

Following general procedure II gave 45% yield of product. ¹H NMR (500 MHz, CDCl₃) δ 8.15-8.08 (m, 2H), 7.70 (t, J=7.5 Hz, 1H), 7.54 (t, J=7.7 Hz, 2H), 7.16 (d, J=15.4 Hz,

122

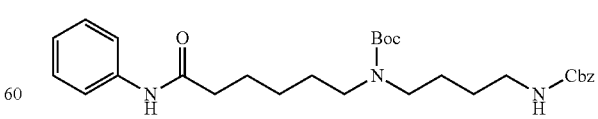

To a stirred solution of benzyl 4-aminobutylcarbamate hydrochloride (1.863 g, 7.2 mmol) in water was added 6-bromohexanoic acid (1.17 g, 6 mmol) and NaOH (1.44 g, 36 mmol) in water at 25° C. The reaction was stirred overnight to yield secondary amine, after which di-tert-butyl dicarbonate (2.62 g, 12 mmol) was added. The reaction mixture was then stirred at 25° C. for 2 h, then the reaction was acidified to pH=1 using 2 M HCl, and extracted with ethyl acetate. The organic extracts were combined, washed with brine and dried over anhydrous $Na_2SO_4$. The mixture was then concentrated in vacuum to give crude carboxylic acid. To a stirred solution of the crude carboxylic acid in 12 ml $CH_2Cl_2$ were added dicyclohexylcarbodiimide (1.486 g, 7.2 mmol) and 1-hydroxybenzotriazole hydrate (0.973 g, 7.2 mmol) at 0° C. The reaction mixture was stirred for 30 min, after which triethylamine (2.53 ml, 18 mmol) and aniline (0.6 ml, 6.6 mmol) were added. The reaction was stirred for 12 h at room temperature. The mixture was quenched with sat $NH_4Cl$ solution and extracted with $CH_2Cl_2$. The organic extracts were combined, then washed with brine and dried over $Na_2SO_4$. The mixture was then concentrated in vacuum, and purified by flash chromatography over silica gel (hexanes/ethyl acetate=7:3) to give the 1.2 g desired product as a colorless oil. Yield: 48%. $^1$H NMR (500 MHz, $CDCl_3$) δ 8.30 (br s, 1H), 7.54 (d, J=7.9 Hz, 2H), 7.31 (d, J=4.2 Hz, 5H), 7.28-7.19 (m, 2H), 7.04 (t, J=7.4 Hz, 1H), 5.28-5.10 (m, 1H), 5.07 (s, 2H), 3.23-3.01 (m, 6H), 2.30 (d, J=8.7 Hz, 2H), 1.75-1.63 (m, 2H), 1.56-1.44 (m, 6H), 1.41 (s, 9H), 1.33-1.21 (m, 2H). $^{13}$C NMR (101 MHz, $CDCl_3$) δ 171.83, 156.58, 155.63, 138.41, 136.58, 128.80, 128.46, 128.03, 127.91, 123.87, 119.81, 79.27, 66.51, 47.02, 46.75, 40.71, 37.23, 28.45, 27.73, 27.29, 26.22, 25.59, 25.18. HRESIMS m/z calcd for $C_{29}H_{41}N_3O_5$ [M+Na]$^+$ 534.2939, found 534.2939

123

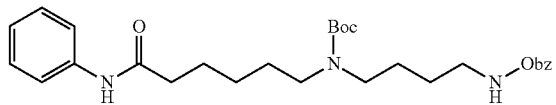

The mixture of substrate 122 (0.192 g, 0.375 mmol) and 10% Pd/C (0.040 g, 0.038 mmol) in tetrahydrofuran was stirred under the atmosphere of hydrogen (balloon) for 1 h. The reaction mixture was filtered through C18, washed with methanol, concentrated to afford a colorless oil. Benzoyl peroxide (0.364 g, 1.128 mmol) was added portionwise to a vigorously stirred mixture of the crude oil in 1.8 ml carbonate buffer solution (pH 10.5) and 2 ml $CH_2Cl_2$ at 25° C. After 4 h, aqueous layer was extracted with $CH_2Cl_2$. The combined organic phases were dried over sodium sulfate and concentrated in vacuum. The residue was purified by flash chromatography over silica gel (hexanes/ethyl acetate=2:1) to afford 90 mg product as a colorless oil. Yield: 48%. $^1$H NMR (500 MHz, $CDCl_3$) δ 8.01 (d, J=7.9 Hz, 2H), 7.58 (t, J=7.4, 1H), 7.53 (d, J=6.6, 2H), 7.45 (t, J=7.7, 2H), 7.29 (t, J=7.6, 2H), 7.08 (t, J=7.2, 1H), 3.25-3.1 (m, 6H), 2.34 (t, J=7.1, 2H), 1.80-1.67 (m, 2H), 1.65-1.48 (m, 6H), 1.43 (s, 9H), 1.39-1.29 (m, 2H). $^{13}$C NMR (101 MHz, $CDCl_3$) δ 171.78, 156.58, 155.63, 138.40, 136.58, 128.80, 128.46, 128.03, 127.91, 123.87, 119.81, 79.28, 66.51, 46.76, 40.71, 37.23, 28.45, 27.73, 27.26, 26.22, 25.90, 25.59, 25.18. HRESIMS m/z calcd for $C_{28}H_{39}N_3O_5$ [M+H]$^+$ 498.2963, found 498.2962.

Following general procedure II gave 48% yield of product. $^1$H NMR (500 MHz, $CD_3OD$) δ 7.66 (d, J=15.7 Hz, 1H), 7.57-7.51 (m, 2H), 7.29 (t, J=7.9 Hz, 2H), 7.08 (t, J=7.4 Hz, 1H), 6.74 (d, J=15.7 Hz, 1H), 3.78 (s, 3H), 3.72 (t, J=6.7 Hz, 2H), 3.21 (q, J=7.2 Hz, 4H), 2.38 (t, J=7.3 Hz, 2H), 1.72 (p, J=7.5 Hz, 2H), 1.68-1.60 (m, 2H), 1.61-1.49 (m, 4H), 1.43 (s, 9H), 1.41-1.31 (m, 2H). $^{13}$C NMR (75 MHz, $CD_3OD$) δ 174.45, 167.38, 165.80, 157.45, 139.89, 134.00, 131.77, 129.75, 125.09, 121.22, 80.87, 61.54, 52.66, 37.84, 32.75, 28.74, 27.49, 26.63, 24.86, 23.70, 14.46, 14.43.

125

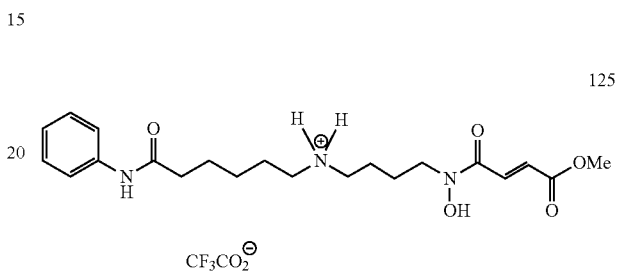

To boc-protected amine 124 (5 mg, 0.01 mmol) in 0.2 ml $CH_2Cl_2$ at 0° C. was added 0.2 ml trifluoroacetic acid and the reaction solution was stirred at 0° C. for 30 min before concentration. The residue was passed through a short plug of reverse phase silca gel to give 5 mg product as a reddish oil. Yield: 97%. $^1$H NMR (500 MHz, $CD_3OD$) δ 7.65 (d, J=15.7 Hz, 1H), 7.54 (d, J=7.9 Hz, 2H), 7.30 (t, J=7.9 Hz, 2H), 7.09 (t, J=7.4 Hz, 1H), 6.75 (d, J=15.7 Hz, 1H), 3.80 (s, 3H), 3.76 (t, J=6.5 Hz, 2H), 3.09-2.96 (m, 4H), 2.42 (t, J=7.2 Hz, 2H), 1.83-1.63 (m, 8H), 1.52-1.42 (m, 2H). $^{13}$C NMR (101 MHz, $CD_3OD$) δ 174.12, 167.30, 165.98, 139.74, 133.72, 132.00, 129.78, 125.18, 121.17, 61.56, 52.73, 37.35, 30.78, 27.04, 26.09, 24.64, 24.26, 20.88, 14.47. HRESIMS m/z calcd for $C_{21}H_{31}N_3O_5$ [M+H]$^+$ 406.2337, found 406.2331.

126

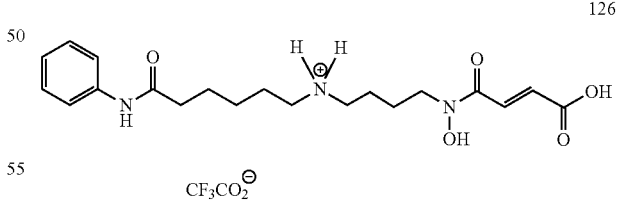

124

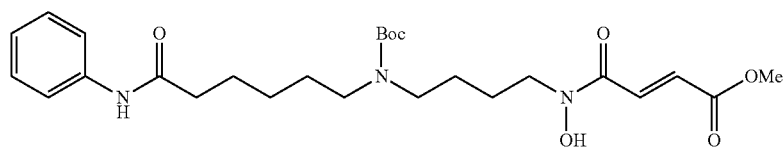

To substrate 124 (9 mg, 0.018 mmol) in 0.2 ml tetrahydrofuran was added LiOH monohydrate (7.5 mg, 0.18 mmol) in 0.2 ml water. After 1 h, 4 M HCl in dioxane (0.045 ml, 0.18 mmol) was added and the solution was concentrated. The residue dissolved in CHCl$_3$/$^i$PrOH=2:1, and the solution was washed with water, dried over sodium sulfate, filtered and concentrated. The residue was dissolved in 0.2 ml CH$_2$Cl$_2$ and cooled to 0° C. 0.1 ml trifluoroacetic acid was added and the solution was stirred at 0° C. for 20 min before concentration. The residue was passed through a short plug of reverse phase silca gel to give 8 mg product as a reddish oil. Yield: 89%. $^1$H NMR (300 MHz, CD$_3$OD) δ 7.63 (d, J=15.7 Hz, 1H), 7.54 (d, J=7.9 Hz, 2H), 7.30 (t, J=7.7 Hz, 2H), 7.08 (t, J=7.3 Hz, 1H), 6.71 (d, J=15.7 Hz, 1H), 3.76 (t, J=6.2 Hz, 2H), 3.02 (q, J=7.7 Hz, 4H), 2.42 (t, J=7.1 Hz, 2H), 1.84-1.62 (m, 8H), 1.56-1.39 (m, 2H). $^{13}$C NMR (75 MHz, CD$_3$OD) δ 174.13, 172.97, 166.30, 139.81, 133.54, 133.06, 129.78, 125.18, 121.19, 61.53, 37.34, 35.67, 32.74, 30.15, 27.00, 26.02, 23.69, 14.43.

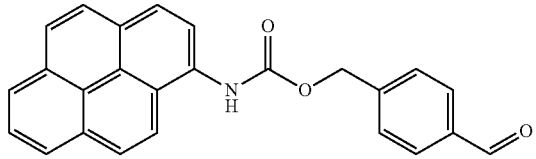

127

Following general procedure III gave 48% yield of product. $^1$H NMR (500 MHz, (CD$_3$)$_2$CO) δ 10.05 (s, 1H), 9.24 (s, 1H), 8.50-8.31 (m, 2H), 8.24 (dd, J=13.7, 7.3 Hz, 2H), 8.18-8.00 (m, 5H), 8.00-7.89 (m, 2H), 7.79-7.65 (m, 2H), 5.40 (s, 2H). $^{13}$C NMR (75 MHz, (CD$_3$)$_2$CO) δ 192.58, 155.54, 144.70, 137.21, 136.83, 133.04, 132.70, 132.33, 131.94, 130.47, 129.78, 129.42, 128.88, 128.16, 127.42, 127.17, 126.08, 125.98, 125.87, 125.73, 122.88, 122.42, 66.50. HRESIMS m/z calcd for C$_{25}$H$_{17}$NO$_3$ [M+Na]$^+$ 402.1101, found 402.1106

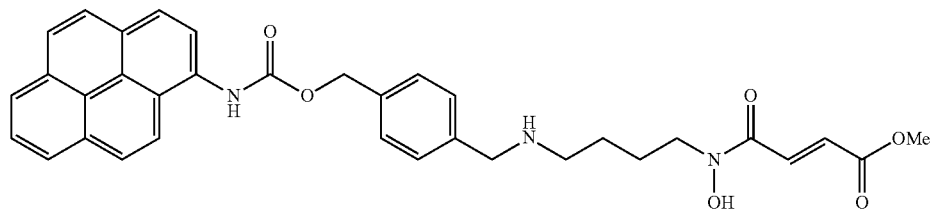

128

Following general procedure IV gave 25% yield of product. $^1$H NMR (300 MHz, CD$_3$OD) δ 8.27-8.09 (m, 6H), 8.09-7.98 (m, 2H), 7.65 (d, J=15.7 Hz, 1H), 7.60-7.44 (m, 5H), 6.74 (d, J=15.7 Hz, 1H), 5.33 (s, 2H), 4.16 (s, 2H), 3.79 (s, 3H), 3.74 (t, J=6.2 Hz, 2H), 3.09-2.99 (m, 2H), 1.84-1.60 (m, 4H). $^{13}$C NMR (75 MHz, CD$_3$OD) δ 167.33, 157.42, 139.89, 133.76, 132.75, 132.39, 132.34, 131.98, 131.06, 130.49, 129.74, 129.67, 128.65, 128.31, 128.25, 127.96, 127.37, 126.44, 126.37, 126.31, 126.05, 126.03, 125.78, 122.62, 67.34, 54.80, 52.71, 52.15, 48.24, 24.70, 24.38.

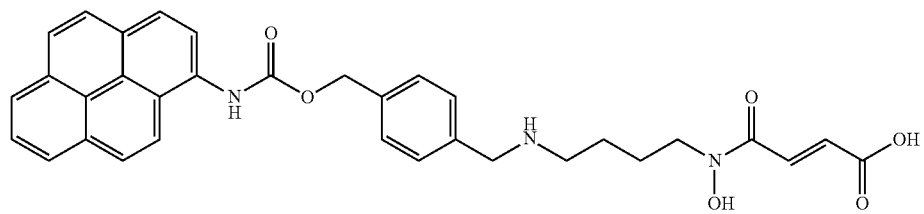

129

Following general procedure V gave 72% yield of product. ¹H NMR (500 MHz, CD₃OD) δ 8.28-8.16 (m, 4H), 8.13 (d, J=9.2 Hz, 1H), 8.07 (s, 4H), 8.03 (t, J=7.6 Hz, 1H), 7.63 (d, J=15.7 Hz, 1H), 7.53 (s, 3H), 6.72 (d, J=15.7 Hz, 1H), 5.34 (s, 2H), 4.21 (s, 2H), 3.76 (t, J=6.2 Hz, 2H), 3.09 (t, J=7.6 Hz, 2H), 1.84-1.65 (m, 4H). ¹³C NMR (75 MHz, CD₃OD) δ 168.39, 166.27, 157.37, 139.93, 133.58, 132.98, 132.69, 132.36, 132.28, 132.24, 131.16, 130.41, 129.66, 129.61, 128.62, 128.21, 127.91, 127.32, 126.33, 126.25, 126.03, 126.00, 125.72, 123.99, 122.58, 67.30, 51.98, 48.24, 47.85, 24.67, 24.19.

Following general procedure V gave 72% yield of product. ¹H NMR (300 MHz, CD₃OD) δ 7.69-7.37 (m, 5H), 7.37-7.12 (m, 5H), 6.75 (d, J=15.3 Hz, 1H), 5.12 (s, 2H), 4.29 (s, 2H), 4.22 (s, 2H), 3.75 (t, J=5.3 Hz, 2H), 3.10 (t, J=6.1 Hz, 2H), 1.92-1.64 (m, 4H). ¹³C NMR (75 MHz, CD₃OD) δ 166.98, 158.90, 158.85, 140.42, 139.81, 136.51, 132.17, 131.35, 131.15, 129.44, 129.14, 128.19, 128.10, 66.86, 51.88, 48.59, 48.19, 45.39, 24.75, 24.27. HRESIMS m/z calcd for $C_{24}H_{29}N_3O_6$ [M+H]⁺ 456.2130, found 456.2123

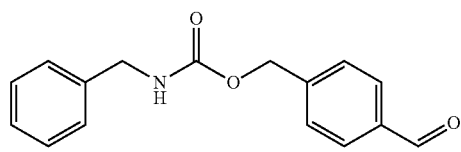

130

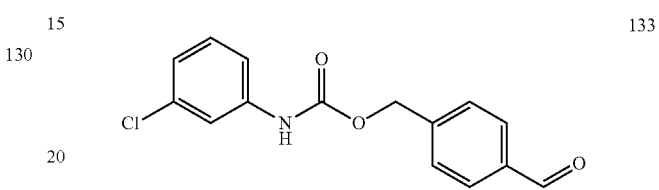

133

Following general procedure III gave 50% yield of product. ¹H NMR (500 MHz, CDCl₃) δ 10.02 (s, 1H), 7.88 (d, J=7.9 Hz, 2H), 7.52 (d, J=7.8 Hz, 2H), 7.37-7.32 (m, 2H), 7.30 (d, J=7.1 Hz, 3H), 5.22 (s, 2H), 5.12 (s, 1H), 4.41 (d, J=6.0 Hz, 2H). ¹³C NMR (75 MHz, CDCl₃) δ 191.87, 156.17, 143.47, 138.33, 135.75, 129.79, 128.54, 127.80, 127.41, 127.38, 65.67, 45.00. HRESIMS m/z calcd for $C_{16}H_{15}NO_3$ [M+Na]⁺ 292.0945, found 292.0943

Following general procedure III gave 63% yield of product. ¹H NMR (500 MHz, CDCl₃) δ 10.03 (s, 1H), 7.91 (d, J=8.1 Hz, 2H), 7.56 (d, J=8.1 Hz, 2H), 7.53 (s, 1H), 7.25-7.19 (m, 2H), 7.06 (dt, J=7.1, 2.1 Hz, 1H), 6.73 (s, 1H), 5.28 (s, 2H). ¹³C NMR (75 MHz, CDCl₃) δ 191.91, 152.80, 142.62, 138.75, 135.95, 134.65, 129.95, 129.93, 128.08, 123.59, 118.69, 116.62, 66.08. HRESIMS m/z calcd for $C_{15}H_{12}ClNO_3$ [M+Na]⁺ 312.0398, found 312.0399

131

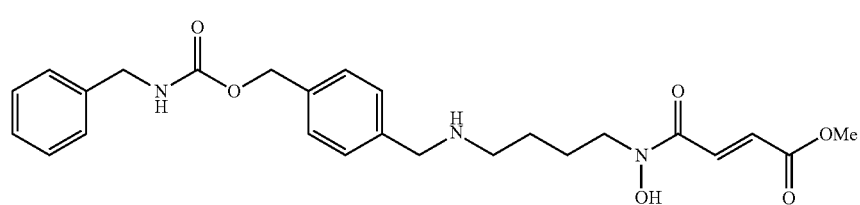

Following general procedure IV gave 54% yield of product. ¹H NMR (300 MHz, CD₃OD) δ 7.67 (d, J=15.7 Hz, 1H), 7.40 (s, 4H), 7.35-7.19 (m, 5H), 6.72 (d, J=15.7 Hz, 1H), 5.11 (s, 2H), 4.29 (s, 2H), 3.97 (s, 2H), 3.79 (s, 3H), 3.73 (t, J=6.4 Hz, 2H), 2.86 (t, J=7.3 Hz, 2H), 1.84-1.51 (m, 4H). ¹³C NMR (75 MHz, CD₃OD) δ 167.41, 165.59, 158.89, 140.52, 138.93, 135.78, 134.05, 131.58, 130.40, 129.46, 129.19, 128.21, 128.13, 67.00, 52.92, 52.90, 52.67, 48.88, 45.48, 25.59, 24.93. HRESIMS m/z calcd for $C_{25}H_{31}N_3O_6$ [M+H]⁺ 470.2286, found 470.2279

132

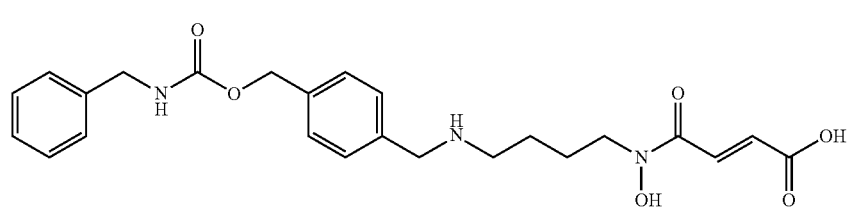

134

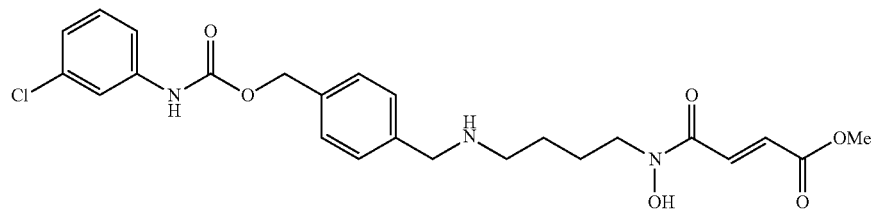

Following general procedure IV gave 43% yield of product. $^1$H NMR (300 MHz, CD$_3$OD) δ 7.67 (d, J=15.7 Hz, 1H), 7.58 (t, J=2.0 Hz, 1H), 7.50-7.37 (m, 4H), 7.34-7.17 (m, 2H), 7.01 (ddd, J=7.7, 2.1, 1.3 Hz, 1H), 6.72 (d, J=15.7 Hz, 1H), 5.20 (s, 2H), 3.93 (s, 2H), 3.79 (s, 3H), 3.73 (t, J=6.5 Hz, 2H), 2.81 (t, J=7.4 Hz, 2H), 1.82-1.56 (m, 4H). $^{13}$C NMR (75 MHz, CD$_3$OD) δ 167.46, 165.46, 155.38, 141.73, 138.14, 136.88, 135.50, 134.18, 131.47, 131.12, 130.34, 129.45, 123.76, 119.42, 117.79, 67.25, 53.17, 52.70, 52.69, 48.95, 25.98, 25.03. HRESIMS m/z calcd for C$_{24}$H$_{28}$ClN$_3$O$_6$ [M+H]$^+$ 490.1740, found 490.1736

135

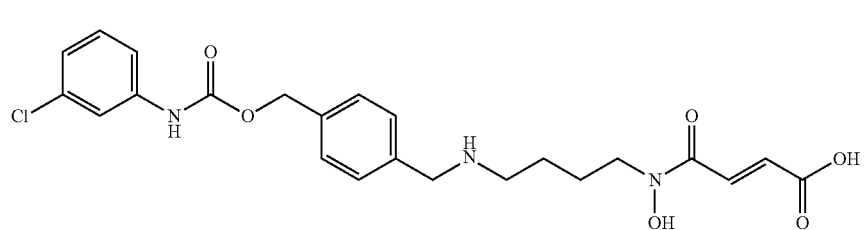

Following general procedure V gave 72% yield of product. $^1$H NMR (300 MHz, CD$_3$OD) δ 7.59 (s, 1H), 7.59-7.46 (m, 4H), 7.38 (d, J=15.4 Hz, 1H), 7.30 (d, J=8.3 Hz, 1H), 7.23 (t, J=8.0 Hz, 1H), 7.00 (dd, J=8.1, 1.8 Hz, 1H), 6.83 (d, J=13.9 Hz, 1H), 5.22 (s, 2H), 4.21 (s, 2H), 3.74 (t, J=5.9 Hz, 2H), 3.08 (t, J=7.7 Hz, 2H), 1.90-1.60 (m, 5H). $^{13}$C NMR (75 MHz, CD$_3$OD) δ 155.30, 141.65, 140.12, 139.46, 139.43, 135.38, 132.40, 131.38, 131.36, 131.11, 129.46, 128.92, 123.72, 119.35, 117.83, 66.96, 51.91, 48.15, 35.39, 24.78, 24.27. HRESIMS m/z calcd for C$_{23}$H$_{26}$ClN$_3$O$_6$ [M+H]$^+$ 476.1583, found 476.1579.

136

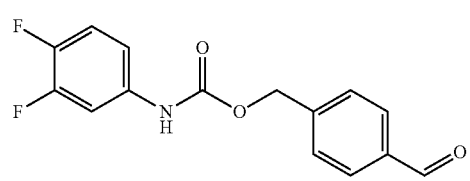

Following general procedure III gave 80% yield of product. $^1$H NMR (300 MHz, (CD$_3$)$_2$CO) δ 10.05 (d, J=0.5 Hz, 1H), 8.00-7.90 (m, 2H), 7.72-7.61 (m, 3H), 7.35-7.15 (m, 2H), 5.31 (s, 2H). $^{13}$C NMR (75 MHz, (CD$_3$)$_2$CO) δ 192.56, 154.12, 150.71, 146.58, 144.26, 137.28, 137.07, 130.46, 128.98, 118.14, 115.21, 108.30, 66.42. HRESIMS m/z calcd for C$_{23}$H$_{25}$F$_2$N$_3$O$_6$ [M+H]$^+$ 478.1785, found 478.1778

137

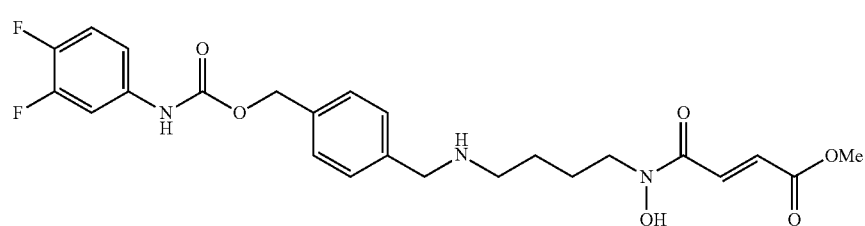

Following general procedure IV gave 40% yield of product. $^1$H NMR (300 MHz, CD$_3$OD) δ 7.67 (d, J=15.7 Hz, 1H), 7.59-7.45 (m, 1H), 7.45-7.32 (m, 4H), 7.21-7.03 (m, 2H), 6.71 (d, J=15.7 Hz, 1H), 5.17 (s, 2H), 3.85 (s, 2H), 3.78 (s, 3H), 3.72 (t, J=6.5 Hz, 2H), 2.73 (t, J=7.2 Hz, 2H), 1.73 (p, J=6.5 Hz, 2H), 1.60 (p, J=7.4 Hz, 2H). $^{13}$C NMR (75 MHz, CD$_3$OD) δ 167.47, 165.37, 155.47, 151.28, 147.21, 138.35, 137.64, 137.40, 134.24, 131.35, 130.08, 129.37, 118.17, 115.48, 108.80, 67.33, 53.50, 52.63, 49.15, 49.13, 26.50, 25.11. HRESIMS m/z calcd for C$_{24}$H$_{27}$F$_2$N$_3$O$_6$ [M+H]$^+$ 492.1941, found 492.1940

138

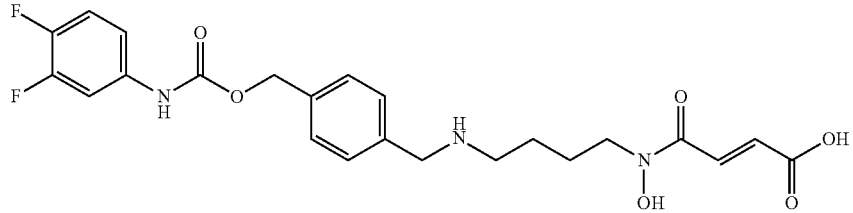

Following general procedure V gave 96% yield of product. $^1$H NMR (300 MHz, CD$_3$OD) δ 7.64-7.42 (m, 6H), 7.24-7.05 (m, 2H), 6.75 (d, J=14.5 Hz, 1H), 5.21 (s, 2H), 4.22 (s, 2H), 3.74 (t, J=5.8 Hz, 2H), 3.14-2.99 (m, 2H), 1.90-1.66 (m, 4H). $^{13}$C NMR (75 MHz, CD$_3$OD) δ 166.96, 159.90, 155.37, 151.22, 147.19, 139.53, 137.30, 137.21, 136.12, 132.40, 131.35, 129.51, 118.15, 115.59, 108.79, 66.98, 51.93, 48.51, 48.19, 24.75, 24.26. HRESIMS m/z calcd for C$_{23}$H$_{25}$F$_2$N$_3$O$_6$ [M+H]$^+$ 478.1785, found 478.1778

139

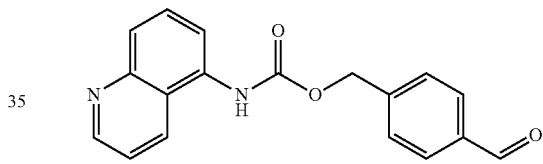

Following general procedure III gave 63% yield of product. $^1$H NMR (300 MHz, CD$_3$OD) δ 10.01 (s, 1H), 8.90-8.81 (m, 1H), 8.61-8.50 (m, 1H), 8.00-7.92 (m, 2H), 7.92-7.85 (m, 1H), 7.84-7.72 (m, 2H), 7.72-7.61 (m, 1H), 7.60-7.53 (m, 2H), 5.35 (s, 2H).

140

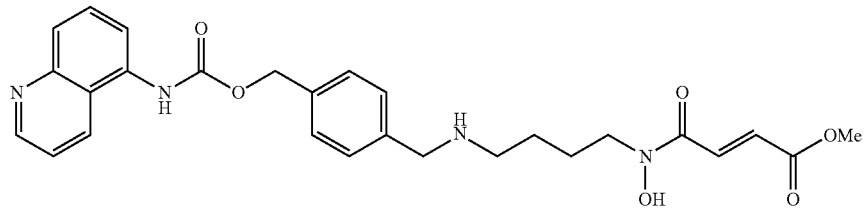

Following general procedure IV gave 89% yield of product. $^1$H NMR (400 MHz, CD$_3$OD) δ 8.86 (dd, J=4.3, 1.7 Hz, 1H), 8.58-8.48 (m, 1H), 7.91-7.83 (m, 1H), 7.76 (d, J=7.5 Hz, 2H), 7.65 (d, J=15.7 Hz, 1H), 7.61-7.46 (m, 5H), 6.75 (d, J=15.8 Hz, 1H), 5.29 (s, 2H), 4.20 (s, 2H), 3.79 (s, 3H), 3.76 (t, J=6.3 Hz, 2H), 3.13-3.02 (m, 2H), 1.86-1.66 (m, 4H). $^{13}$C NMR (101 MHz, CD$_3$OD) δ 167.26, 165.82, 156.77, 151.21, 148.95, 139.54, 135.12, 133.71, 133.23, 132.48, 132.04, 131.88, 131.11, 130.76, 129.62, 126.22, 124.69, 122.23, 67.35, 52.70, 52.02, 48.50, 48.19, 24.63, 24.27.

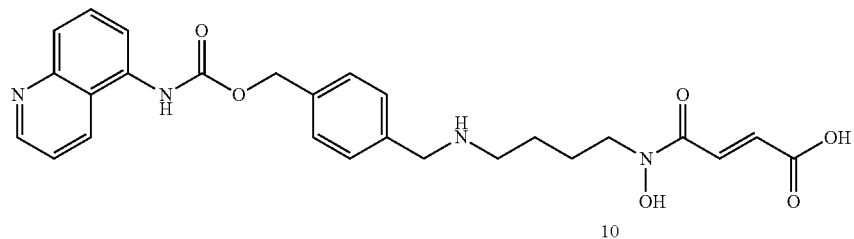

141

Following general procedure V gave 41% yield of product.

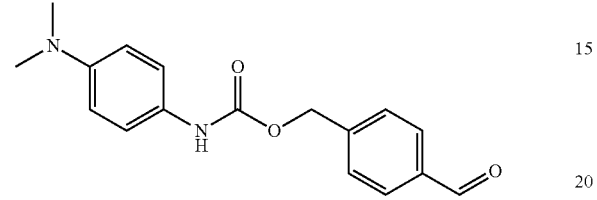

142

Following general procedure III gave 57% yield of product. ¹H NMR (500 MHz, CD₃OD) δ 9.99 (s, 1H), 7.96-7.91 (m, 2H), 7.62 (d, J=7.9 Hz, 2H), 7.27 (d, J=8.3 Hz, 2H), 6.77 (d, J=9.1 Hz, 2H), 5.26 (s, 2H).

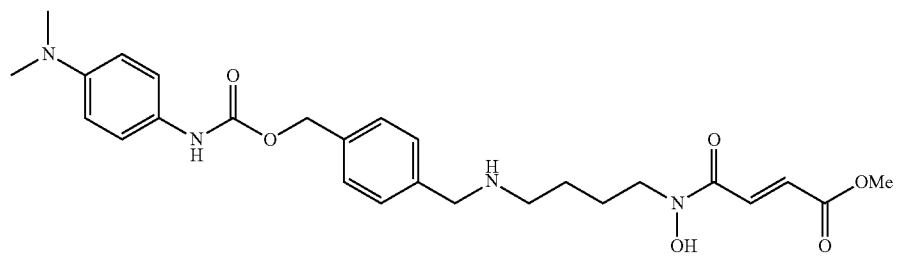

143

Following general procedure IV gave 40% yield of product. ¹H NMR (300 MHz, CD₃OD) δ 7.67 (d, J=15.7 Hz, 1H), 7.56-7.36 (m, 4H), 7.24 (d, J=8.5 Hz, 2H), 6.84-6.61 (m, 3H), 5.16 (s, 2H), 3.94 (s, 2H), 3.79 (s, 3H), 3.73 (t, J=6.4 Hz, 2H), 2.87 (s, 6H), 2.82 (t, J=7.3 Hz, 2H), 1.75 (p, J=7.4, 6.7 Hz, 2H), 1.71-1.53 (m, 2H).

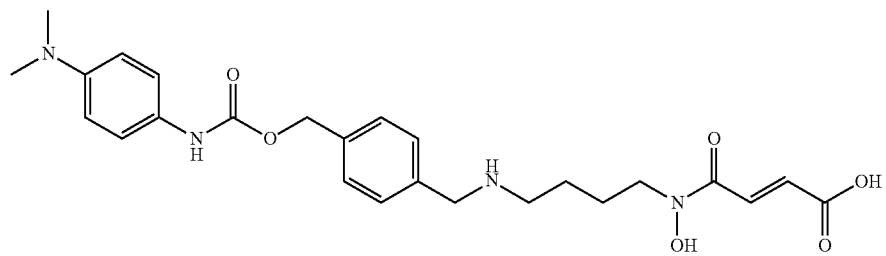

144

Following general procedure V gave 95% yield of product. ¹H NMR (300 MHz, CD₃OD) δ 7.51 (s, 5H), 7.25 (d, J=8.3 Hz, 2H), 6.92-6.68 (m, 3H), 5.19 (s, 2H), 4.20 (s, 2H), 3.74 (t, J=4.9 Hz, 2H), 3.08 (t, J=6.6 Hz, 2H), 1.89-1.61 (m, 4H).

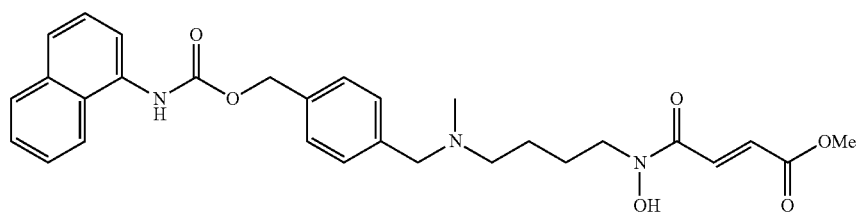

145

General Procedure VI:

To methylstat (0.025 g, 0.049 mmol) in 0.5 ml methanol were added 37% formaldehyde in water (0.040 ml, 0.49 mmol) and acetic acid (0.006 ml, 0.1 mmol). After 20 min, sodium cyanoborohydride (0.031 g, 0.49 mmol) was added at 0° C. and the reaction mixture was stirred at 25° C. for 12 h before concentration. The residue was dissolved in ethyl acetate and the solution was washed with water, brine, then dried over sodium sulfate, filtered and concentrated. The residue was purified by silica gel chromatography using $CH_2Cl_2$/MeOH=20:1 to give 22 mg product as a yellowish oil. Yield: 86%. $^1$H NMR (400 MHz, $CD_3OD$) δ 8.05-7.95 (m, 1H), 7.85-7.85 (m, 1H), 7.73 (d, J=8.4 Hz, 1H), 7.65 (d, J=15.6 Hz, 1H), 7.61-7.42 (m, 9H), 6.75 (d, J=15.6 Hz, 1H), 5.27 (s, 2H), 4.10 (s, 2H), 3.79 (s, 3H), 3.75 (t, J=5.6 Hz, 2H), 2.97 (t, J=7.3 Hz, 2H), 2.60 (s, 3H), 1.81-1.64 (m, 4H). $^{13}$C NMR (75 MHz, $CD_3OD$) δ 167.33, 165.98, 157.22, 139.68, 135.66, 134.49, 133.83, 132.80, 131.90, 129.72, 129.44, 129.33, 127.15, 127.11, 126.81, 126.70, 126.53, 123.16, 122.54, 67.23, 61.20, 56.95, 52.69, 48.64, 40.69, 24.84, 23.04. HRESIMS m/z calcd for $C_{29}H_{33}N_3O_6$ $[M+H]^+$ 520.2443, found 520.2443.

146

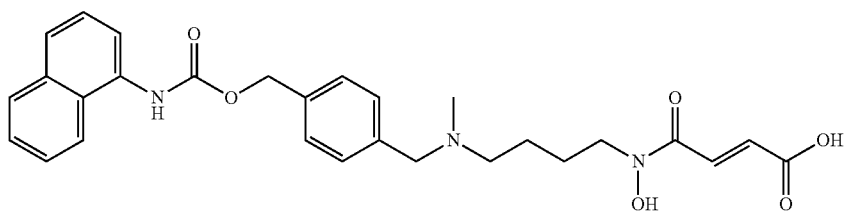

Following general procedure V gave 93% yield of product. $^1$H NMR (300 MHz, $CD_3OD$) δ 8.08-7.96 (m, 1H), 7.93-7.83 (m, 1H), 7.72 (d, J=8.2 Hz, 1H), 7.62 (d, J=7.4 Hz, 1H), 7.59-7.33 (m, 8H), 6.84 (d, J=15.4 Hz, 1H), 5.28 (s, 2H), 4.26 (s, 2H), 3.74 (t, J=5.6 Hz, 3H), 3.12 (t, J=7.3 Hz, 2H), 2.71 (s, 3H), 1.87-1.60 (m, 4H). $^{13}$C NMR (75 MHz, $CD_3OD$) δ 167.81, 157.23, 157.18, 140.28, 139.53, 135.63, 134.48, 132.32, 130.88, 129.76, 129.49, 129.32, 128.97, 127.17, 127.13, 126.81, 126.54, 123.19, 122.58, 67.11, 60.56, 56.58, 54.80, 40.06, 24.75, 22.42. HRESIMS m/z calcd for $C_{28}H_{31}N_3O_6$ $[M+H]^+$ 506.2286, found 506.2287.

147

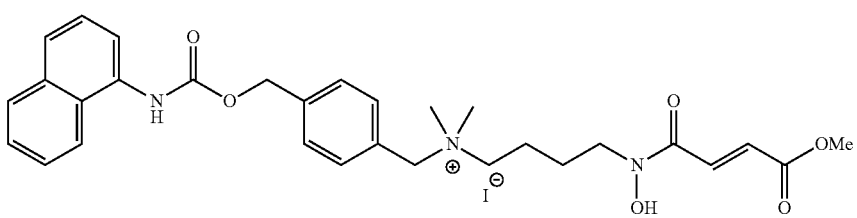

General Procedure VII:

To compound 145 (0.03 g, 0.058 mmol) in 0.2 ml methanol was added iodomethane (0.018 ml, 0.29 mmol) and the reaction solution was stirred at 25° C. for 12 h before concentration. The residue was passed through a short plug of reverse phase silica gel to afford 0.037 g product as a colorless oil. Yield: 97%. $^1$H NMR (300 MHz, $CD_3OD$) δ 8.09-7.97 (m, 1H), 7.93-7.84 (m, 1H), 7.79-7.71 (m, 1H), 7.66 (d, J=15.7 Hz, 1H), 7.63-7.55 (m, 5H), 7.55-7.43 (m, 3H), 6.76 (d, J=15.7 Hz, 1H), 5.32 (s, 2H), 4.54 (s, 2H), 3.86-3.73 (m, 5H), 3.44-3.33 (m, 2H), 3.02 (s, 6H), 2.01-1.84 (m, 2H), 1.77 (p, J=6.7 Hz, 2H). $^{13}$C NMR (101 MHz, $CD_3OD$) δ 167.29, 166.00, 157.08, 141.25, 135.59, 134.44, 134.32, 133.80, 131.94, 129.72, 129.35, 129.28, 128.30, 127.22, 127.17, 126.83, 126.57, 123.18, 122.54, 68.41, 66.97, 65.11, 52.76, 50.37, 48.51, 24.40, 20.83. HRESIMS m/z calcd for $C_{30}H_{35}N_3O_6$ $[M+H]^+$ 534.2599, found 534.2602.

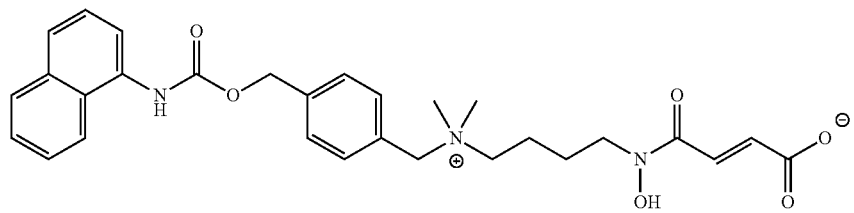

148

Following general procedure V gave 89% yield of product. ¹H NMR (300 MHz, CD₃OD) δ 8.09-7.99 (m, 1H), 7.93-7.84 (m, 1H), 7.73 (d, J=8.2 Hz, 1H), 7.68-7.40 (m, 9H), 6.78 (d, J=14.9 Hz, 1H), 5.31 (s, 2H), 4.53 (s, 2H), 3.79 (t, J=6.3 Hz, 2H), 3.43-3.33 (m, 2H), 3.01 (s, 6H), 2.04-1.81 (m, 2H), 1.83-1.67 (m, 2H).

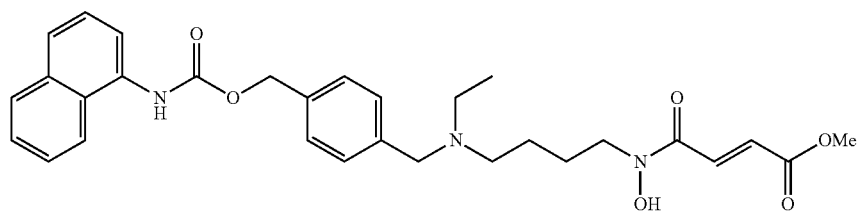

149

Following general procedure VI gave 85% yield of product. ¹H NMR (300 MHz, CD₃OD) δ 8.06-7.96 (m, 1H), 7.91-7.83 (m, 1H), 7.76-7.69 (m, 1H), 7.66 (d, J=15.7 Hz, 1H), 7.62-7.58 (m, 1H), 7.54-7.29 (m, 7H), 6.73 (d, J=15.7 Hz, 1H), 5.23 (s, 2H), 3.78 (s, 3H), 3.74-3.60 (m, 4H), 2.72-2.50 (m, 4H), 1.79-1.43 (m, 4H), 1.10 (t, J=6.9 Hz, 3H). ¹³C NMR (101 MHz, CD₃OD) δ 167.36, 165.55, 157.26, 138.26, 137.51, 135.62, 134.54, 134.03, 131.63, 130.87, 129.64, 129.30, 129.13, 127.08, 127.06, 126.66, 126.53, 123.17, 122.34, 67.58, 58.27, 53.40, 52.65, 49.09, 48.22, 25.34, 24.08, 11.12.

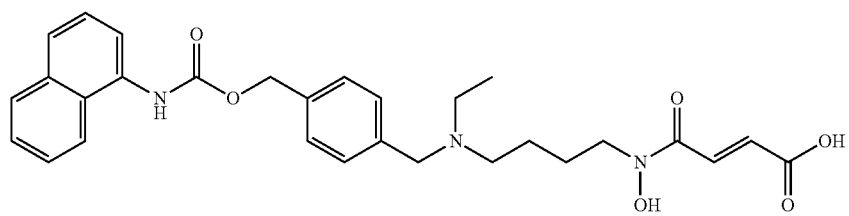

150

Following general procedure V gave 98% yield of product. ¹H NMR (500 MHz, CD₃OD) δ 8.07-7.99 (m, 1H), 7.92-7.85 (m, 1H), 7.72 (d, J=8.2 Hz, 1H), 7.68-7.36 (m, 9H), 6.83 (d, J=15.2 Hz, 1H), 5.29 (s, 2H), 4.32 (s, 2H), 3.73 (t, 5.1 Hz, 2H), 3.20-3.04 (m, 4H), 1.85-1.61 (m, 4H), 1.33 (t, J=6.9 Hz, 3H). ¹³C NMR (75 MHz, CD₃OD) δ 167.56, 157.24, 157.17, 140.40, 138.61, 135.66, 134.53, 132.28, 130.67, 129.76, 129.56, 129.43, 129.34, 127.16, 127.13, 126.81, 126.55, 123.21, 122.56, 67.08, 57.32, 52.61, 48.72, 42.74, 24.79, 21.89, 8.97.

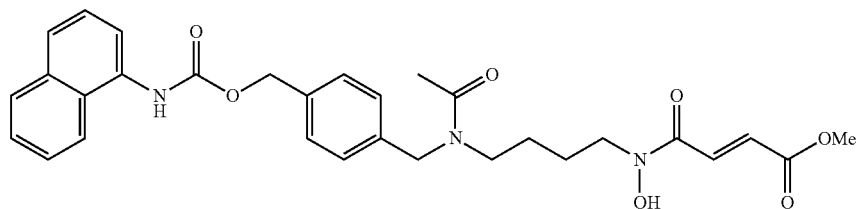

151

To methylstat (0.02 mmol, 0.04 mmol) in 0.2 ml tetrahydrofuran were added acetic anhydride (0.008 ml, 0.08 mmol) and 0.2 ml saturated NaHCO₃. The mixture was stirred for 12 h before concentration. The residue was dissolved in 0.35 ml methanol, to which was added K₂CO₃ (0.019 mg, 0.14 mmol). After 1 h, 2 N HCl was added until pH<2. The mixture was concentrated and water was added. The aqueous layer was extracted with ethyl acetate 3 times. The combined organic phases were dried over sodium sulfate, filtered and concentrated. The residue was purified by silica gel chromatography using CH₂Cl₂/MeOH=20:1 to give 8 mg product as a colorless oil. Yield: 75%. ¹H NMR (300 MHz, CD₃OD) δ 8.07-7.97 (m, 1H), 7.92-7.84 (m, 1H), 7.76-7.69 (m, 1H), 7.68-7.58 (m, 2H), 7.54-7.37 (m, 5H), 7.27 (t, J=7.9 Hz, 2H), 6.72 (dd, J=15.7, 6.0 Hz, 1H), 5.22 (d, J=6.0 Hz, 2H), 4.68-4.57 (m, 2H), 3.79 (s, 3H), 3.72-3.65 (m, 2H), 3.47-3.36 (m, 2H), 2.15 (d, J=23.0 Hz, 3H), 1.76-1.47 (m, 4H).

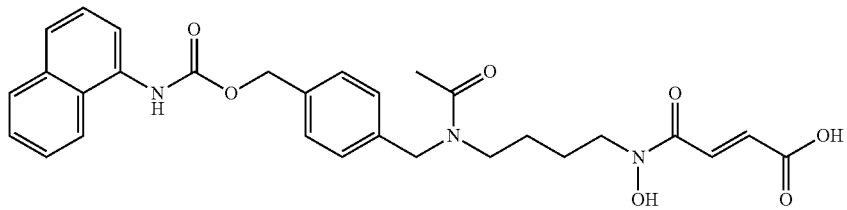

152

20

Following general procedure V gave 95% yield of product. ¹H NMR (300 MHz, CD₃OD) δ 8.09-7.97 (m, 1H), 7.92-7.83 (m, 1H), 7.72 (d, J=8.2 Hz, 1H), 7.62 (d, J=7.4 Hz, 1H), 7.58-7.34 (m, 6H), 7.27 (t, J=8.1 Hz, 2H), 6.79 (d, J=12.4 Hz, 1H), 5.23 (d, J=5.7 Hz, 2H), 4.63 (d, J=9.1 Hz, 2H), 3.69 (t, J=6.3 Hz, 2H), 3.47-3.34 (m, 2H), 2.16 (d, J=24.2 Hz, 3H), 1.77-1.48 (m, 4H).

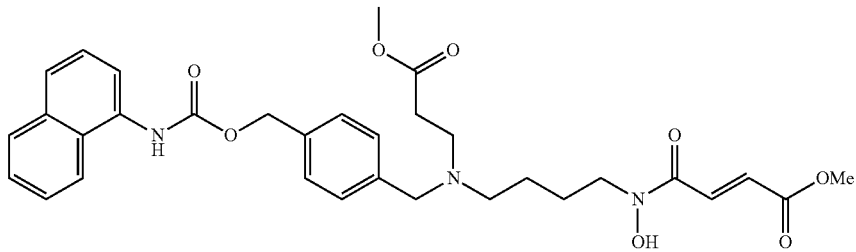

153

To methylstat (0.04 g, 0.079 mmol) in 0.2 ml tetrahydrofuran was added 0.2 ml methyl acrylate and the reaction solution was stirred at 50° C. for 48 h before concentration. The residue was purified by silica gel chromatography using CH₂Cl₂/MeOH=30:1 to give 0.037 g product as a yellowish oil. Yield: 79%. ¹H NMR (300 MHz, CD₃OD) δ 8.06-7.97 (m, 1H), 7.92-7.84 (m, 1H), 7.72 (d, J=8.5 Hz, 1H), 7.64 (d, J=15.7 Hz, 1H), 7.56-7.29 (m, 8H), 6.72 (d, J=15.7 Hz, 1H), 5.22 (s, 2H), 3.78 (s, 3H), 3.70-3.61 (m, 5H), 3.59 (s, 2H), 2.78 (t, J=7.0 Hz, 2H), 2.49 (dt, J=11.3, 7.0 Hz, 4H), 1.76-1.55 (m, 2H), 1.58-1.38 (m, 2H). ¹³C NMR (101 MHz, CD₃OD) δ 174.78, 167.35, 165.63, 157.27, 140.32, 136.85, 135.61, 134.55, 134.06, 131.67, 130.28, 129.58, 129.30, 129.07, 127.07, 127.05, 126.75, 126.59, 123.20, 122.32, 67.74, 59.04, 53.98, 52.65, 52.12, 50.31, 33.09, 25.26, 24.87.

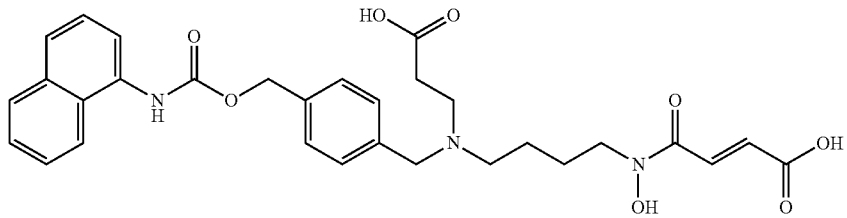

154

Following general procedure V gave 72% yield of product. $^1$H NMR (300 MHz, CD$_3$OD) δ 8.08-7.98 (m, 1H), 7.93-7.83 (m, 1H), 7.73 (d, J=8.2 Hz, 1H), 7.68-7.40 (m, 9H), 6.73 (d, J=15.6 Hz, 1H), 5.29 (s, 2H), 4.36 (s, 2H), 3.70 (t, J=6.1 Hz, 2H), 3.42-3.30 (m, 2H), 3.21-3.05 (m, 2H), 2.71 (t, J=5.9 Hz, 2H), 1.93-1.56 (m, 4H).

Following general procedure II gave 50% yield of product. $^1$H NMR (500 MHz, CD$_3$OD) δ 8.13-8.06 (m, 2H), 7.70 (t, J=7.5 Hz, 1H), 7.57-7.50 (m, 2H), 7.14 (d, J=15.4 Hz, 1H), 6.93 (d, J=15.4 Hz, 1H), 4.57 (s, 1H), 4.19 (q, J=7.1 Hz, 2H), 3.91 (t, J=7.0 Hz, 2H), 3.15 (q, J=6.8 Hz, 2H), 1.72 (p, J=7.2 Hz, 2H), 1.62-1.52 (m, 2H), 1.41 (s, 9H), 1.26 (t, J=7.1 Hz, 2H). $^{13}$C NMR (101 MHz, CDCl$_3$) δ 164.45, 163.87, 163.79, 155.58, 134.29, 132.60, 130.43, 129.55, 128.48, 125.55, 78.11, 60.61, 47.61, 39.36, 27.82, 26.69, 23.78, 13.46.

155

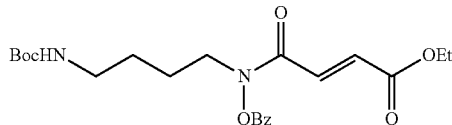

156

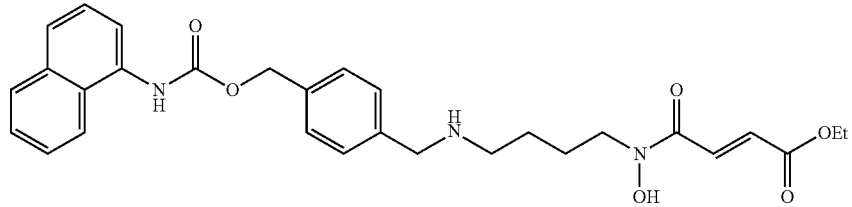

Following general procedure IV gave 70% yield of product. $^1$H NMR (500 MHz, CD$_3$OD) δ 8.04-7.96 (m, 1H), 7.93-7.84 (m, 1H), 7.73 (d, J=8.3 Hz, 1H), 7.66 (d, J=15.7 Hz, 1H), 7.64-7.58 (m, 1H), 7.57-7.36 (m, 7H), 6.72 (d, J=15.7 Hz, 1H), 5.26 (s, 2H), 4.25 (q, J=7.1 Hz, 2H), 4.05 (s, 2H), 3.74 (t, J=6.6 Hz, 2H), 2.99-2.85 (m, 2H), 1.85-1.71 (m, 2H), 1.72-1.62 (m, 2H), 1.30 (t, J=7.1 Hz, 3H). $^{13}$C NMR (101 MHz, CD$_3$OD) δ 166.87, 165.47, 157.11, 138.88, 135.51, 134.47, 134.38, 133.80, 133.77, 131.94, 130.63, 129.35, 129.29, 127.12, 127.09, 126.72, 126.49, 123.09, 122.48, 67.25, 62.25, 52.47, 48.73, 48.45, 25.01, 24.72, 14.43. HRESIMS m/z calcd for C$_{29}$H$_{33}$N$_3$O$_6$ [M+H]$^+$ 520.2443, found 520.2449.

157

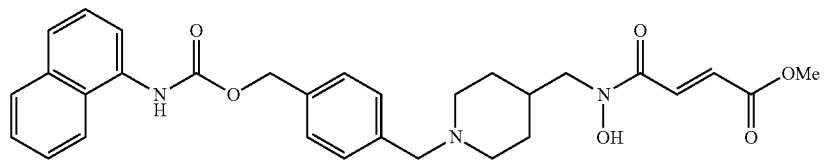

Following general procedures I, II and IV gave 30% yield of product which started from tert-Butyl 4-aminomethylpiperidine-1-carboxylate. $^1$H NMR (500 MHz, CD$_3$OD) δ 8.04-7.97 (m, 1H), 7.90-7.84 (m, 1H), 7.72 (d, J=8.2 Hz, 1H), 7.65 (d, J=15.6 Hz, 1H), 7.62 (br s, 1H), 7.56-7.38 (m, 7H), 6.74 (d, J=15.6 Hz, 1H), 5.26 (s, 2H), 3.96 (s, 2H), 3.79 (s, 3H), 3.63 (d, J=7.1 Hz, 2H), 3.28-3.08 (m, 2H), 2.57 (t, J=11.4 Hz, 2H), 2.07-1.93 (m, 1H), 1.82 (d, J=13.7 Hz, 2H), 1.51-1.36 (m, 2H).

158

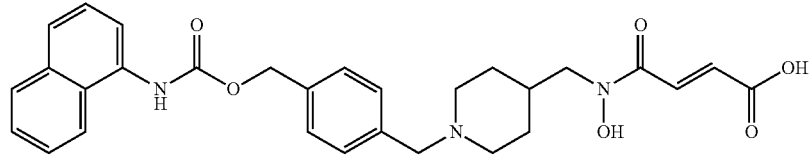

Following general procedure V gave 80% yield of product. ¹H NMR (500 MHz, CD₃OD) δ 8.05-7.96 (m, 1H), 7.91-7.85 (m, 1H), 7.73 (d, J=8.3 Hz, 1H), 7.66-7.35 (m, 9H), 6.81 (d, J=17.7 Hz, 1H), 5.29 (s, 2H), 4.28 (s, 2H), 3.65 (d, J=6.1 Hz, 2H), 3.51-3.42 (m, 2H), 3.08-2.91 (m, 2H), 2.22-2.05 (m, 1H), 1.94 (d, J=14.4 Hz, 2H), 1.62-1.44 (m, 2H).

159

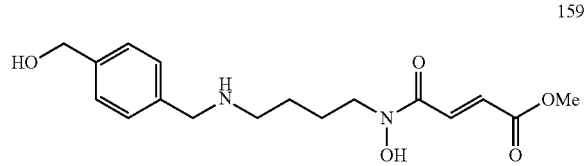 [SMILES: COC(=O)/C=C/C(=O)N(O)CCCCNCc1ccc(CO)cc1]

Following general procedure IV gave 50% yield of product which started from 4-(hydroxylmethyl)benzaldehyde. ¹H NMR (500 MHz, CD₃OD) δ 7.70 (d, J=15.5 Hz, 1H), 7.35 (s, 4H), 6.71 (d, J=15.5 Hz, 1H), 4.60 (s, 2H), 3.81 (s, 2H), 3.79 (s, 3H), 3.72 (t, J=6.5 Hz, 2H), 2.69 (t, J=6.5 Hz, 2H), 1.86-1.69 (m, 2H), 1.65-1.53 (m, 2H). ¹³C NMR (75 MHz, CD₃OD) δ 167.54, 165.05, 142.30, 137.70, 134.43, 131.07, 129.85, 128.25, 64.88, 54.80, 53.65, 52.60, 49.17, 26.65, 25.16.

160

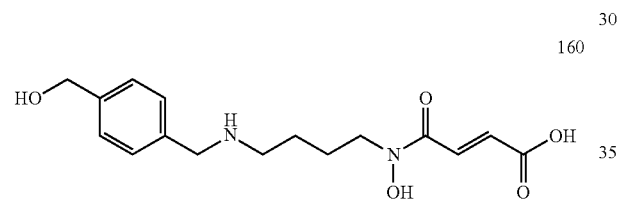

Following general procedure V gave 80% yield of product. ¹H NMR (300 MHz, CD₃OD) δ 7.57 (d, J=15.6 Hz, 1H), 7.54-7.40 (m, 4H), 6.73 (d, J=15.6 Hz, 1H), 4.64 (s, 2H), 4.20 (s, 2H), 3.76 (t, J=5.9 Hz, 2H), 3.14-3.00 (m, 2H), 1.86-1.65 (m, 4H). ¹³C NMR (75 MHz, CD₃OD) δ 167.31, 166.54, 144.28, 134.33, 132.76, 131.33, 131.19, 128.46, 64.54, 54.93, 52.00, 48.58, 24.74, 24.27.

161

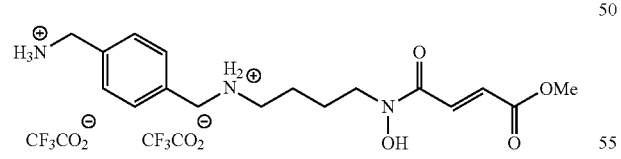

To compound 191 (0.014 g, 0.032 mmol) in 0.3 ml CH₂Cl₂ at 0° C. was added 0.1 ml trifluoroacetic acid. The reaction solution was stirred at 0° C. for 15 min before concentration. The residue was passed through a short plug of reverse phase silica gel to give 0.017 g product as a reddish oil. Yield: 94%. ¹H NMR (300 MHz, CD₃OD) δ 7.65 (d, J=15.8 Hz, 1H), 7.61-7.51 (m, 4H), 6.74 (d, J=15.8 Hz, 1H), 4.24 (s, 2H), 4.16 (s, 2H), 3.80 (s, 3H), 3.75 (t, J=6.1 Hz, 2H), 3.09 (t, J=7.5 Hz, 2H), 1.85-1.65 (m, 4H).

162

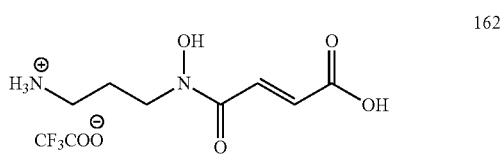

To compound 104 (0.07 g, 0.17 mmol) in 1 ml tetrahydrofuran was added 2 N NaOH (0.86 ml, 1.72 mmol). After 2 h, 2 N HCl was added until pH<2. The aqueous layer was extracted with CHCl₃/ⁱPrOH=2:1 three times. The combined organic phases were dried over sodium sulfate, filtered and concentrated. The residue was dissolved in 0.6 ml CH₂Cl₂, to which was added 0.3 ml trifluoroacetic acid. After stirring at 0° C. for 15 min, the solution was concentrated and the residue was passed through a short plug of reverse phase silica gel to give 47 mg product as a red oil. Yield: 90%. ¹H NMR (500 MHz, CD₃OD) δ 7.61 (d, J=15.6 Hz, 1H), 6.74 (d, J=15.7 Hz, 1H), 3.83 (t, J=6.4 Hz, 2H), 2.97 (t, J=7.4 Hz, 2H), 2.03 (p, J=6.9 Hz, 2H). ¹³C NMR (101 MHz, CD₃OD) δ 168.40, 166.63, 133.27, 133.14, 46.57, 38.24, 25.94. HRESIMS m/z calcd for C₇H₁₂N₂O₄ [M+H]⁺ 189.0875, found 189.0867.

163

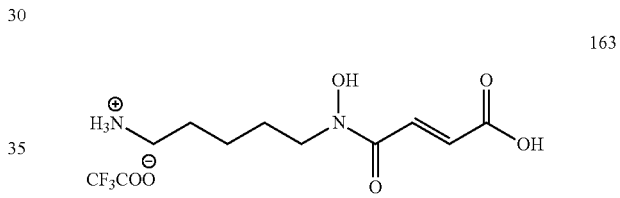

Following the same procedure to prepare 162 gave 84% yield of product. ¹H NMR (500 MHz, CD₃OD) δ 7.63 (d, J=15.7 Hz, 1H), 6.70 (d, J=15.7 Hz, 1H), 3.73 (t, J=6.8 Hz, 2H), 2.92 (t, J=7.7 Hz, 2H), 1.84-1.61 (m, 4H), 1.50-1.31 (m, 2H). ¹³C NMR (101 MHz, CD₃OD) δ 168.51, 166.06, 133.76, 132.77, 48.90, 40.54, 28.05, 26.99, 24.38. HRESIMS m/z calcd for C₉H₁₇N₂O₄ [M+H]⁺ 217.1188, found 217.1187.

164

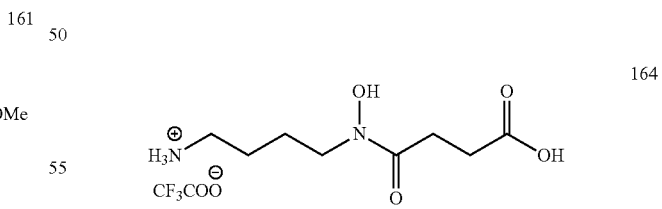

Following the same procedure to prepare 162 gave 91% yield of product. ¹H NMR (500 MHz, CD₃OD) δ 3.66 (t, J=6.4 Hz, 2H), 2.94 (t, J=7.5 Hz, 2H), 2.77 (t, J=6.6 Hz, 2H), 2.61-2.53 (m, 2H), 1.79-1.67 (m, 2H), 1.69-1.59 (m, 2H). ¹³C NMR (101 MHz, CD₃OD) δ 176.82, 174.70, 47.99, 40.25, 29.41, 28.19, 25.41, 24.48. HRESIMS m/z calcd for C₈H₁₆N₂O₄ [M+H]⁺ 205.1188, found 205.1182.

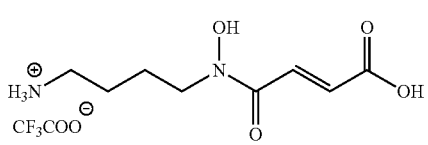

165

Following the same procedure to prepare 162 gave 89% yield of product. $^1$H NMR (300 MHz, CD$_3$OD) δ 7.63 (d, J=15.7 Hz, 1H), 6.72 (d, J=15.7 Hz, 1H), 3.76 (t, J=6.4 Hz, 2H), 2.96 (t, J=7.5 Hz, 2H), 1.87-1.71 (m, 2H), 1.73-1.59 (m, 2H). $^{13}$C NMR (75 MHz, CD$_3$OD) δ 168.60, 166.27, 133.69, 132.89, 48.49, 40.25, 25.55, 24.50. HRESIMS m/z calcd for C$_8$H$_{14}$N$_2$O$_4$ [M+H]$^+$ 203.1032, found 203.1028.

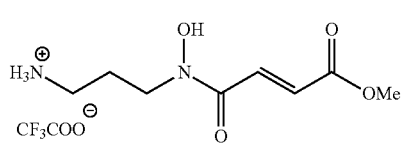

166

To compound 104 (0.1 g, 0.25 mmol) in 1.3 ml methanol was added potassium carbonate (0.068 g, 0.49 mmol). After 2 h, water was added and 2 N HCl was added until pH<2. The aqueous layer was extracted with ethyl acetate 3 times. The combined organic phases were dried over sodium sulfate, filtered and concentrated. The residue was dissolved in 0.6 ml CH$_2$Cl$_2$, to which was added 0.3 ml trifluoroacetic acid. After stirring at 0° C. for 15 min, the solution was concentrated and the residue was passed through a short plug of reverse phase silica gel to give 45 mg product as a red oil. Yield: 60%. $^1$H NMR (500 MHz, CD$_3$OD) δ 7.64 (d, J=15.7 Hz, 1H), 6.73 (d, J=15.7 Hz, 1H), 3.73 (t, J=6.9 Hz, 2H), 3.07 (t, J=6.8 Hz, 2H), 1.89-1.72 (m, 2H). $^{13}$C NMR (75 MHz, CD$_3$OD) δ 167.29, 166.43, 133.43, 132.22, 52.72, 46.63, 38.20, 25.95. HRESIMS m/z calcd for C$_8$H$_{14}$N$_2$O$_4$ [M+H]$^+$ 203.1027, found 203.1026.

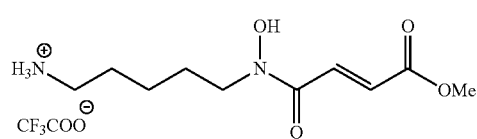

167

Following the same procedure to prepare 166 gave 99% yield of product. $^1$H NMR (300 MHz, CD$_3$OD) δ 7.65 (d, J=15.7 Hz, 1H), 6.74 (d, J=15.7 Hz, 1H), 3.80 (s, 3H), 3.73 (t, J=6.8 Hz, 2H), 2.92 (t, J=7.6 Hz, 2H), 1.82-1.59 (m, 4H), 1.54-1.34 (m, 2H). $^{13}$C NMR (75 MHz, CD$_3$OD) δ 167.38, 165.80, 133.97, 131.71, 52.67, 48.94, 40.53, 28.03, 26.97, 24.38. HRESIMS m/z calcd for C$_{10}$H$_{18}$N$_2$O$_4$ [M+H]$^+$ 231.1340, found 231.1345.

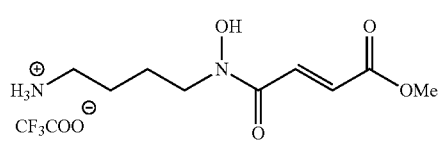

168

Following the same procedure to prepare 166 gave 98% yield of product. $^1$H NMR (300 MHz, CD$_3$OD) δ 3.67 (s, 3H), 3.65 (t, J=6.3 Hz, 2H), 2.95 (t, J=7.2 Hz, 2H), 2.79 (dd, J=7.6, 5.7 Hz, 2H), 2.59 (dd, J=7.6, 5.6 Hz, 2H), 1.80-1.57 (m, 4H). $^{13}$C NMR (75 MHz, CD$_3$OD) δ 175.28, 174.47, 52.21, 48.15, 40.25, 29.36, 28.21, 25.47, 24.50. HRESIMS m/z calcd for C$_9$H$_{18}$N$_2$O$_4$ [M+H]$^+$ 219.1340, found 219.1343.

169

Following the same procedure to prepare 166 gave 99% yield of product. $^1$H NMR (500 MHz, CD$_3$OD) δ 7.65 (d, J=15.5 Hz, 1H), 6.74 (d, J=15.5 Hz, 1H), 3.80 (s, 3H), 3.76 (t, J=6.5 Hz, 2H), 2.96 (t, J=7.5 Hz, 2H), 1.82-1.72 (m, 2H), 1.72-1.62 (m, 2H). $^{13}$C NMR (75 MHz, CD$_3$OD) δ 167.34, 165.98, 133.82, 131.90, 52.69, 48.50, 40.24, 25.58, 24.52. HRESIMS m/z calcd for C$_9$H$_{16}$N$_2$O$_4$ [M+H]$^+$ 217.1183, found 217.1184.

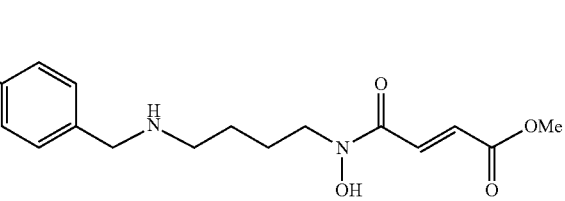

170

To compound 161 (0.01 g, 0.018 mmol) in 0.2 ml tetrahydrofuran were added benzoic anhydride (0.006 g, 0.027 mmol) and diisopropylethylamine (0.015 ml, 0.089 mmol). The reaction solution was stirred at 25° C. for 36 h before concentration. The residue was dissolved in ethyl acetate, washed with water, saturated NaHCO$_3$ and brine, then dried over sodium sulfate, filtered and concentrated. The residue was purified by silica gel chromatography using CH$_2$Cl$_2$/MeOH=10:1 to give 5 mg product as a yellowish oil. Yield: 64%. $^1$H NMR (500 MHz, CD$_3$OD) δ 7.85 (d, J=7.5 Hz, 2H), 7.67 (d, J=15.7 Hz, 1H), 7.57-7.51 (m, 1H), 7.51-7.44 (m, 2H), 7.42-7.34 (m, 4H), 6.72 (d, J=15.7 Hz, 1H), 4.58 (s, 2H), 3.91 (s, 2H), 3.79 (s, 3H), 3.72 (t, J=6.6 Hz, 2H), 2.80 (t, J=7.4 Hz, 2H), 1.80-1.69 (m, 2H), 1.62 (p, J=7.5 Hz, 2H).

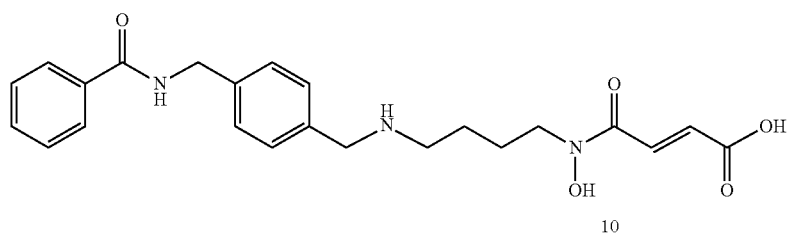

171

Following general procedure V gave 83% yield of product. $^1$H NMR (500 MHz, CD$_3$OD) δ 9.09 (t, J=6.1 Hz, 1H), 7.91-7.81 (m, 2H), 7.61 (d, J=15.6 Hz, 1H), 7.57-7.51 (m, 1H), 7.51-7.41 (m, 6H), 6.71 (d, J=15.6 Hz, 1H), 4.60 (d, J=6.1 Hz, 2H), 4.18 (s, 2H), 3.75 (t, J=6.1 Hz, 2H), 3.07 (t, J=7.7 Hz, 2H), 1.86-1.65 (m, 4H).

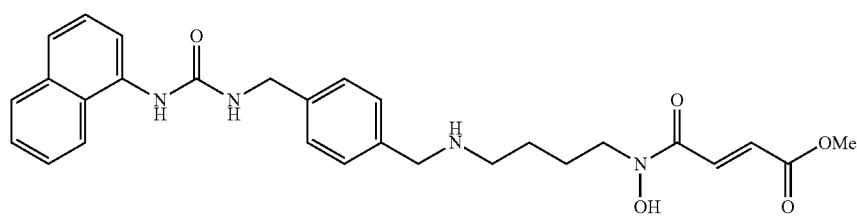

172

To compound 161 (0.013 g, 0.023 mmol) in 0.23 ml acetonitrile were added 1-naphathyl isocyanate (0.004 ml, 0.023 mmol) and diisopropylethylamine (0.020 ml, 0.115 mmol). The reaction solution was stirred at 25° C. for 2 h before concentration. The residue was dissolved in ethyl acetate, washed with saturated NaHCO$_3$ and brine, then dried over sodium sulfate, filtered and concentrated. The residue was purified by silica gel chromatography using CH$_2$Cl$_2$/MeOH=30:1, 10:1 to give 3 mg compound 173 as a grey oil and 4 mg compound 172. Yield of 173: 34%. $^1$H NMR (500 MHz, CD$_3$OD) δ 8.01 (d, J=7.5 Hz, 1H), 7.92-7.86 (m, 1H), 7.73-7.67 (m, 2H), 7.65 (d, J=15.7 Hz, 1H), 7.55-7.37 (m, 7H), 6.75 (d, J=15.7 Hz, 1H), 4.46 (d, J=4.3 Hz, 2H), 4.16 (s, 2H), 3.79 (s, 3H), 3.75 (t, 5.5 Hz, 2H), 3.05 (t, J=7.8 Hz, 2H), 1.85-1.63 (m, 4H).

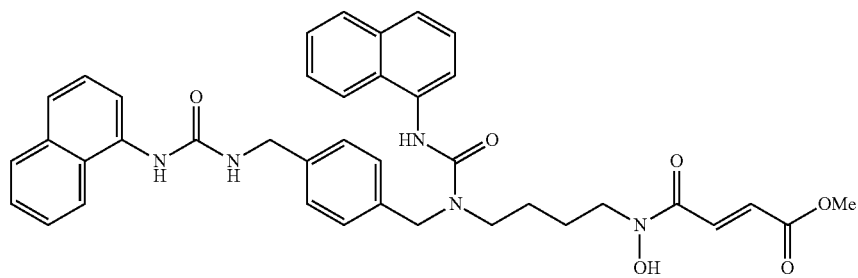

173

Yield: 20%. $^1$H NMR (500 MHz, CD$_3$OD) δ 8.06-7.96 (m, 1H), 7.95-7.83 (m, 2H), 7.82-7.65 (m, 4H), 7.58 (d, J=15.7 Hz, 1H), 7.54-7.34 (m, 11H), 6.48 (d, J=15.7 Hz, 1H), 4.71 (s, 2H), 4.46 (s, 2H), 3.85-3.66 (m, 5H), 3.51 (q, J=7.4 Hz, 2H), 1.86-1.63 (m, 4H).

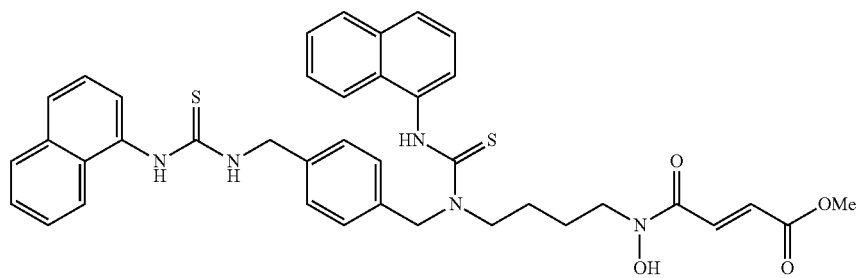

174

Following the same procedure to prepare 173 gave 24% yield of product. $^1$H NMR (500 MHz, CD$_3$OD) δ 7.98 (br s, 1H), 7.95-7.77 (m, 3H), 7.72 (s, 1H), 7.60-7.23 (m, 14H), 6.25 (br s, 1H), 5.20 (s, 2H), 4.79 (s, 2H), 3.82 (br s, 2H), 3.73 (s, 3H), 1.92-1.68 (m, 4H).

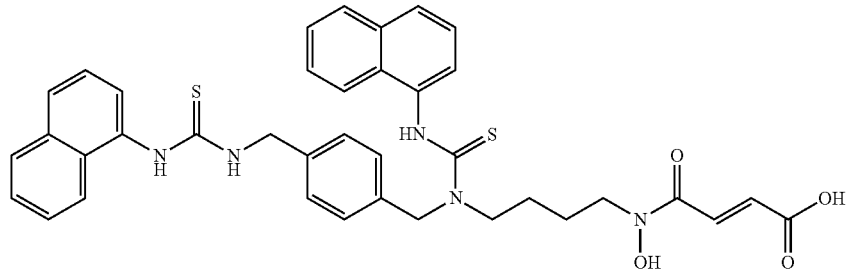

175

Following general procedure V gave 95% yield of product. $^1$H NMR (500 MHz, CD$_3$OD) δ 8.20-7.67 (m, 2H), 7.67-7.20 (m, 12H), 6.50 (br s, 1H), 5.20 (s, 2H), 4.80 (s, 2H), 3.84 (s, 2H), 3.73 (t, J=6.5 Hz, 2H), 1.91-1.77 (m, 2H), 1.77-1.65 (m, 2H).

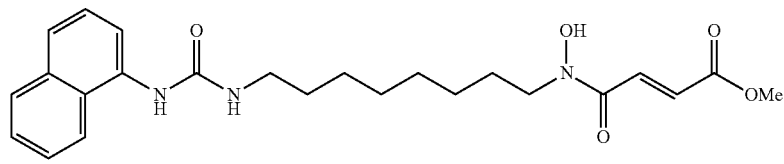

176

Following the same procedure to prepare 172 gave 53% yield of product. $^1$H NMR (300 MHz, CD$_3$OD) δ 8.00 (d, J=8.3 Hz, 1H), 7.94-7.78 (m, 1H), 7.75-7.58 (m, 3H), 7.58-7.34 (m, 3H), 6.73 (d, J=15.7 Hz, 1H), 6.35 (s, 1H), 3.78 (s, 3H), 3.68 (t, J=7.1 Hz, 2H), 3.23 (t, J=6.9 Hz, 2H), 1.80-1.60 (m, 2H), 1.61-1.46 (m, 2H), 1.46-1.20 (m, 8H).

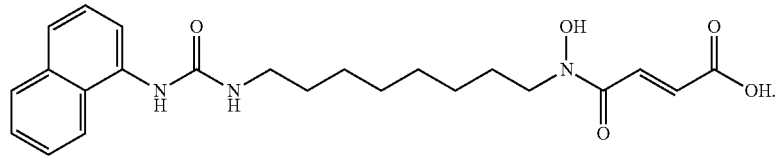

177

Following general procedure V gave 69% yield of product. $^1$H NMR (300 MHz, CD$_3$OD) δ 8.03 (d, J=7.6 Hz, 1H), 7.96-7.79 (m, 1H), 7.79-7.59 (m, 2H), 7.59-7.28 (m, 4H), 6.84 (d, J=15.3 Hz, 1H), 3.67 (t, J=7.1 Hz, 2H), 3.23 (t, J=6.9 Hz, 2H), 1.82-1.61 (m, 2H), 1.61-1.46 (m, 2H), 1.46-1.12 (m, 8H).

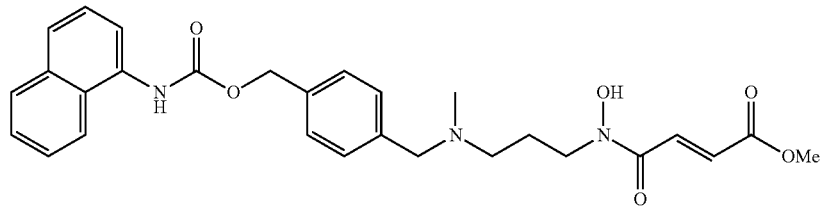

178

Following general procedure VI gave 58% yield of product. ¹H NMR (500 MHz, CD₃OD) δ 8.05-7.98 (m, 1H), 7.91-7.84 (m, 1H), 7.76-7.60 (m, 3H), 7.55-7.39 (m, 5H), 7.33 (d, J=7.6 Hz, 2H), 6.73 (d, J=15.7 Hz, 1H), 5.24 (s, 2H), 3.80 (t, J=5.9 Hz, 2H), 3.76 (s, 3H), 3.64 (s, 2H), 2.61 (t, J=6.1 Hz, 2H), 2.24 (s, 3H), 1.93 (p, J=6.2 Hz, 2H).

179

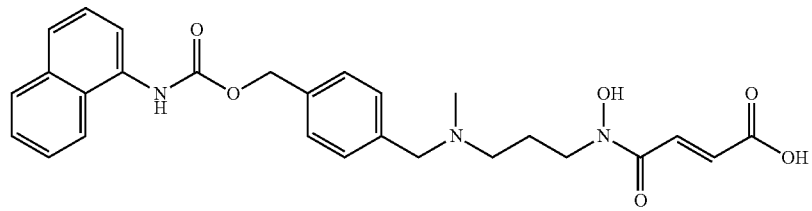

Following general procedure V gave 51% yield of product. ¹H NMR (300 MHz, CD₃OD) δ 8.04 (d, J=7.7 Hz, 1H), 7.94-7.80 (m, 1H), 7.72 (d, J=8.2 Hz, 1H), 7.63 (d, J=7.3 Hz, 1H), 7.58-7.27 (m, 8H), 6.89 (br s, 1H), 5.27 (s, 2H), 4.11 (s, 2H), 3.81 (t, J=6.6 Hz, 2H), 2.98 (t, J=7.1 Hz, 2H), 2.61 (s, 3H), 2.27-1.90 (m, 2H).

180

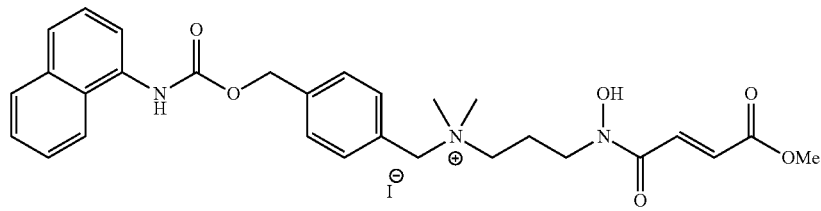

Following general procedure VII gave 95% yield of product. ¹H NMR (500 MHz, CD₃OD) δ 8.12-7.95 (m, 1H), 7.95-7.80 (m, 1H), 7.73 (d, J=8.2 Hz, 1H), 7.68-7.40 (m, 9H), 6.77 (d, J=15.7 Hz, 1H), 5.29 (s, 2H), 4.57 (s, 2H), 3.85 (t, J=6.2 Hz, 2H), 3.79 (s, 3H), 3.38-3.26 (m, 2H), 3.07 (s, 6H), 2.28 (p, J=6.5, 5.7 Hz, 2H).

181

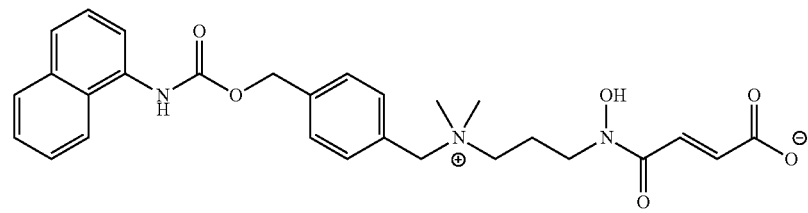

Following general procedure V gave 51% yield of product. ¹H NMR (300 MHz, CD₃OD) δ 8.18-7.97 (m, 1H), 7.98-7.81 (m, 1H), 7.72 (d, J=8.2 Hz, 1H), 7.68-7.18 (m, 9H), 6.91 (s, 1H), 5.30 (s, 2H), 4.54 (s, 2H), 3.84 (t, J=5.5 Hz, 2H), 3.45-3.22 (m, 2H), 3.04 (s, 6H), 2.42-2.18 (m, 2H).

182

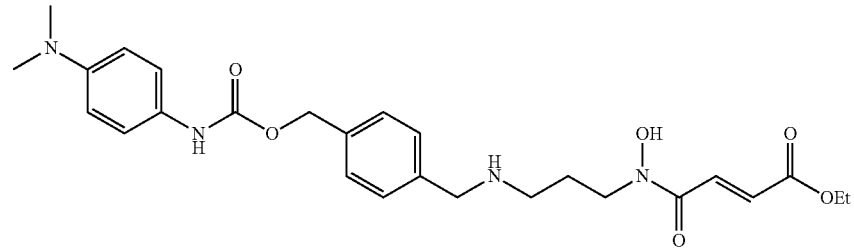

Following general procedure IV gave 36% yield of product. ¹H NMR (400 MHz, CD₃OD) δ 7.69 (d, J=15.7 Hz, 1H), 7.56-7.28 (m, 4H), 7.25 (d, J=8.4 Hz, 2H), 6.80-6.72 (m, 2H), 6.69 (d, J=15.7 Hz, 1H), 5.15 (s, 2H), 4.24 (q, J=7.1 Hz, 2H), 3.88 (s, 2H), 3.82 (t, J=5.6 Hz, 2H), 2.87 (s, 6H), 2.81 (t, J=6.2 Hz, 2H), 1.91 (p, J=6.0 Hz, 2H), 1.30 (t, J=7.1 Hz, 3H).

183

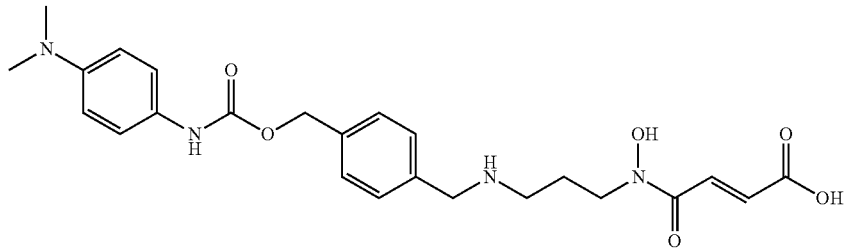

Following general procedure IV gave 88% yield of product. ¹H NMR (500 MHz, CD₃OD) δ 7.64-7.39 (m, 5H), 7.30 (d, J=24.9 Hz, 2H), 6.81 (s, 2H), 6.76 (d, J=15.4 Hz, 1H), 5.19 (s, 2H), 4.21 (s, 2H), 3.83 (t, J=6.4 Hz, 2H), 3.08 (t, J=7.5 Hz, 2H), 2.89 (d, J=1.8 Hz, 6H), 2.16-2.02 (m, 2H).

184

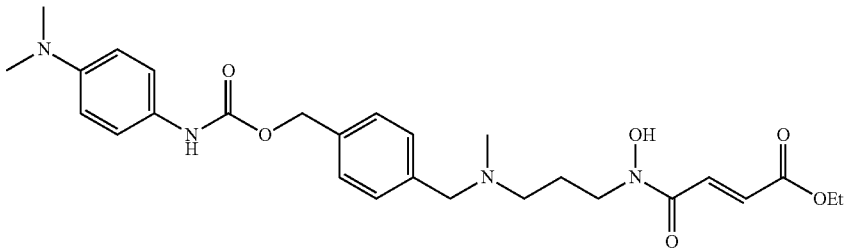

Following general procedure VI gave 71% yield of product. ¹H NMR (300 MHz, CD₃OD) δ 7.68 (d, J=15.7 Hz, 1H), 7.49-7.20 (m, 6H), 6.81-6.74 (m, 2H), 6.71 (d, J=15.7 Hz, 1H), 5.15 (s, 2H), 4.24 (q, J=7.1 Hz, 2H), 3.88-3.74 (m, 2H), 3.64 (s, 2H), 2.86 (s, 6H), 2.70-2.53 (m, 2H), 2.24 (s, 3H), 1.93 (p, J=7.3, 6.7 Hz, 2H), 1.30 (t, J=7.1 Hz, 3H).

185

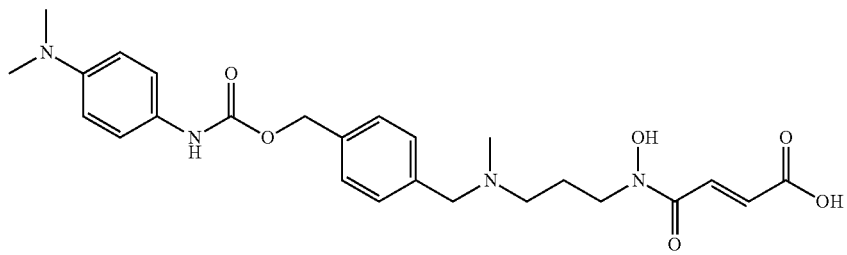

Following general procedure V gave 85% yield of product. ¹H NMR (500 MHz, CD₃OD) δ 7.67-7.36 (m, 5H), 7.35-7.17 (m, 2H), 6.83-6.68 (m, 3H), 5.20 (s, 2H), 4.33 (s, 2H), 3.82 (t, J=6.3 Hz, 2H), 3.21-3.09 (m, 2H), 2.88 (s, 6H), 2.79 (s, 3H), 2.22-2.10 (m, 2H).

186

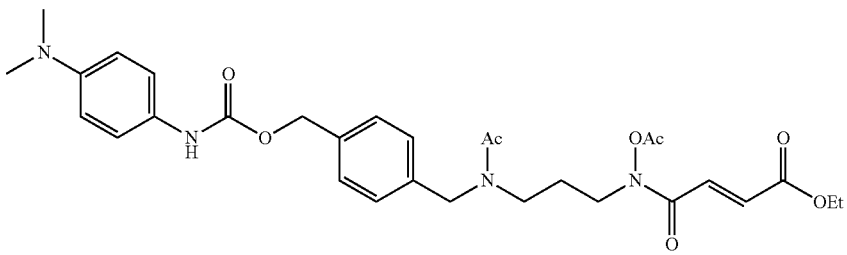

To compound 182 (0.02 mmol, 0.01 mmol) in 0.1 ml tetrahydrofuran were added acetic anhydride (0.004 ml, 0.04 mmol) and 0.1 ml saturated NaHCO$_3$. The mixture was stirred for 12 h. The aqueous layer was extracted with ethyl acetate 3 times. The combined organic phases were dried over sodium sulfate, filtered and concentrated. The residue was purified by silica gel chromatography using CH$_2$Cl$_2$/MeOH=30:1 to give 8 mg product as a colorless oil. Yield: 69%. $^1$H NMR (400 MHz, CD$_3$OD) δ 7.48-7.41 (m, 1H), 7.37 (d, J=8.0 Hz, 1H), 7.34-7.19 (m, 4H), 7.11 (d, J=15.8 Hz, 1H), 6.83-6.70 (m, 3H), 5.14 (d, J=8.5 Hz, 2H), 4.62 (d, J=11.5 Hz, 2H), 4.37-4.11 (m, 2H), 3.77 (q, J=5.9 Hz, 2H), 3.49-3.33 (m, 2H), 2.87 (s, 2H), 2.24 (d, J=5.4 Hz, 3H), 2.16 (dd, J=21.4, 1.2 Hz, 3H), 1.95-1.79 (m, 2H), 1.30 (t, J=7.2 Hz, 3H).

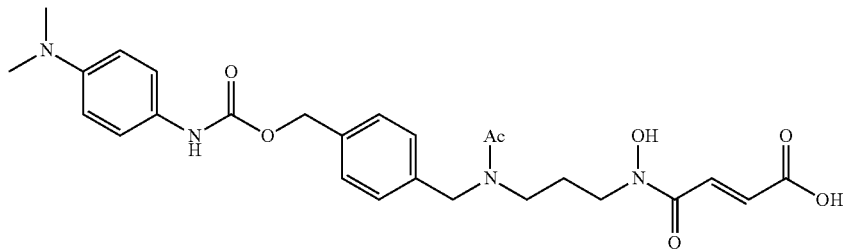

187

Following general procedure V gave 85% yield of product. $^1$H NMR (500 MHz, CD$_3$OD) δ 7.47-7.40 (m, 1H), 7.41-7.34 (m, 1H), 7.34-7.21 (m, 5H), 6.76 (d, J=8.7 Hz, 3H), 5.14 (d, J=10.0 Hz, 2H), 4.64 (d, J=21.3 Hz, 2H), 3.68 (t, J=7.1 Hz, 2H), 3.42-3.24 (m, 2H), 2.87 (s, 6H), 2.16 (d, J=30.0 Hz, 3H), 1.99-1.85 (m, 2H).

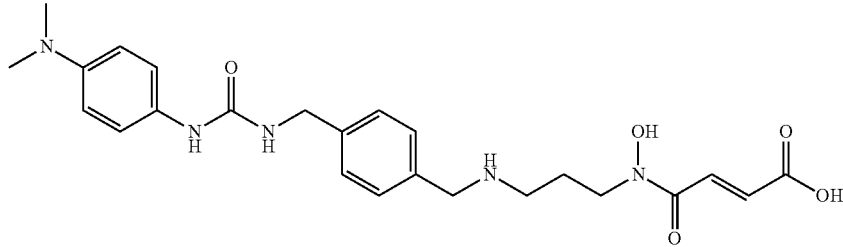

188

Following the same procedure to prepare 173 gave 41% yield of product. $^1$H NMR (300 MHz, CD$_3$OD) δ 7.55-7.35 (m, 4H), 7.25-7.13 (m, 3H), 6.90-6.70 (m, 3H), 5.13 (s, 1H), 4.40 (s, 2H), 4.16 (s, 2H), 3.87-3.73 (m, 2H), 3.05-2.94 (m, 2H), 2.86 (s, 6H), 2.18-1.96 (m, 2H).

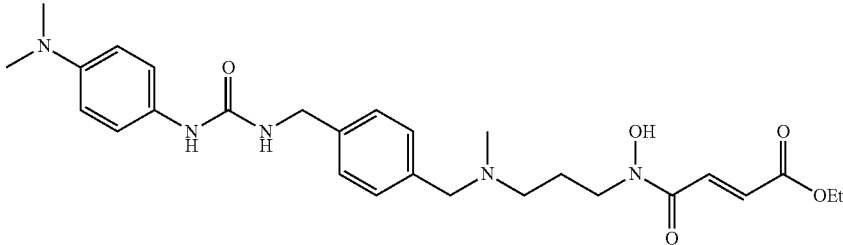

189

Following general procedure VI gave 67% yield of product. ¹H NMR (500 MHz, CD₃OD) δ 7.62 (d, J=15.8 Hz, 1H), 7.41 (s, 4H), 7.18 (d, J=9.0 Hz, 2H), 6.77 (d, J=9.1 Hz, 2H), 6.74 (d, J=15.8 Hz, 1H), 4.40 (s, 2H), 4.25 (q, J=7.1 Hz, 2H), 4.12 (s, 2H), 3.82 (t, J=6.4 Hz, 2H), 3.08-2.93 (m, 2H), 2.87 (s, 6H), 2.64 (s, 3H), 2.17-1.99 (m, 2H), 1.31 (t, J=7.1 Hz, 3H).

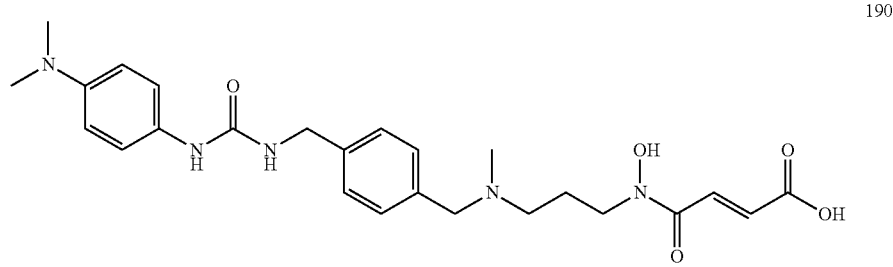 [SMILES: CN(CCCN(O)C(=O)/C=C/C(=O)O)Cc1ccc(CNC(=O)Nc2ccc(N(C)C)cc2)cc1]

190

Following general procedure V gave 61% yield of product. ¹H NMR (300 MHz, CD₃OD) δ 7.64-7.36 (m, 5H), 7.36-7.21 (m, 2H), 7.04-6.84 (m, 2H), 6.73 (d, J=15.5 Hz, 1H), 4.42 (s, 2H), 4.33 (s, 2H), 3.82 (t, 5.1 Hz, 2H), 3.17 (t, 4.8 Hz, 2H), 3.00-2.91 (m, 6H), 2.81 (s, 3H), 2.25-2.09 (m, 2H).

131.00, 130.90, 128.67, 80.26, 52.86, 51.98, 48.48, 48.10, 44.46, 28.78, 24.52, 24.12; HRESIMS m/z calcd for $C_{22}H_{34}N_3O_6$ [M+H]$^+$ 436.2443, found 436.2436.

191

192

To the mixture of tert-butyl N-(4-formylbenzyl)carbamate (0.094 g, 0.4 mmol) and amine 169 (0.079 g, 0.37 mmol) in 3.5 mL methanol at 0° C. was added acetic acid (0.062 mL, 1.1 mmol). After 30 min, sodium cyanoborohydride (0.12 g, 1.82 mmol) was added at 0° C. and the resulting mixture was stirred at room temp for 12 h before concentration. Water was added and aqueous layer was extracted with ethyl acetate 3 times. The combined organic phases were washed with sat NaHCO₃ and brine, dried over sodium sulfate, filtered and concentrated in vacuum. The residue was purified over silica gel using CH₂Cl₂:MeOH=10:1 as eluent to give 0.094 g product as a yellowish oil. Yield: 69%. ¹H-NMR (CD₃OD, 500 MHz): δ=7.65 (d, J=15.7 Hz, 1H), 7.43 (d, J=8.1 Hz, 2H), 7.37 (d, J=8.1 Hz, 2H), 6.75 (d, J=15.7 Hz, 1H), 4.25 (s, 2H), 4.16 (s, 2H), 3.80 (s, 3H), 3.76 (t, J=6.3 Hz, 2H), 3.11-3.01 (m, 2H), 1.85-1.64 (m, 4H), 1.44 (s, 9H); ¹³C-NMR (CD₃OD, 75 MHz): δ=167.14, 165.64, 158.23, 142.39, 133.70, 131.69, To compound 191 (0.023 g, 0.34 mmol) in 0.2 mL CH₂Cl₂ at 0° C. was added 0.1 mL trifluoroacetic acid. The reaction solution was stirred at 0° C. for 0.5 h before concentration in vacuo. The oil was dissolved in 0.5 mL tetrahydrofuran, to which was added the solution of LiOH monohydrate (0.022 g, 0.53 mmol) in 0.5 mL water. The resulting mixture was stirred at room temp for 2 h. The solution was cooled to 0° C. and HCl in dioxane (4 M, 0.11 mL) was added. After 5 min, the solvents were removed in vacuo. The residue was purified over silica gel using MeOH:H₂O=3:1 as eluent to give 0.016 g product as a white solid. Yield: 94%. ¹H NMR (CD₃OD, 400 MHz) δ=7.40 (s, 4H), 7.24 (d, J=15.7 Hz, 1H), 6.76 (d, J=15.7 Hz, 1H), 3.98 (s, 2H), 3.87 (s, 2H), 3.69 (t, J=6.2 Hz, 2H), 2.74 (t, J=7.1 Hz, 2H), 1.79-1.68 (m, 2H), 1.67-1.55 (m, 2H); ¹³C NMR (CD₃OD, 75 MHz) δ=173.96, 167.64, 140.35, 138.84, 137.91, 130.61, 129.71, 128.51, 53.36, 45.21, 26.48, 25.34; HRESIMS m/z calcd for $C_{16}H_{23}N_3O_4$ [M+H]$^+$ 322.1762, found 322.1794.

Synthesis of a Fluorescent Probe

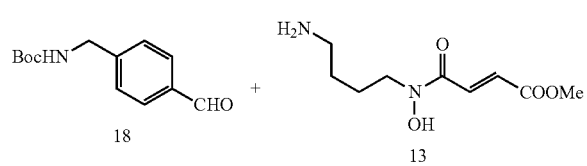
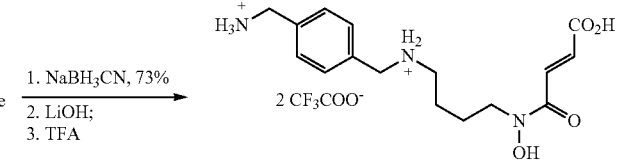

Synthesis of the fluorophore began with a reductive amination reaction of readily available aldehyde 18 and previously synthesized amine 13, followed by hydrolysis of the methyl ester and deprotection of tert-butyloxycarbonyl (Boc) group. The resulting ammonium salt (19) was then treated with fluorescein isothiocyanate (FITC) under mild basic conditions to afford the fluorophore 20. Its methyl ester, 21, was also synthesized in a similar fashion by skipping the hydrolysis reaction.

General Procedure VIII:

To the mixture of fluorescein isothiocyanate isomer I (0.01 g, 0.025 mmol) and amine 192 (0.016 g, 0.05 mmol) in 0.2 mL THF was added 0.2 mL sat NaHCO$_3$ at 0° C. The solution was warmed to room temp and stirred for 12 h. 2 M NaOH (0.12 mL) was added and the mixture was stirred at room temp for 5 min before concentration. The residue was purified over silica gel using CHCl$_3$:MeOH:H$_2$O=6:4:0.5 as eluent to give 0.007 g product as an orange solid. Yield: 37%. $^1$H NMR (CD$_3$OD, 300 MHz) δ=7.73 (s, 1H), 7.67 (dd, J=8.3 Hz, 2.1 Hz, 1H), 7.43 (s, 4H), 7.26 (d, J=16.0 Hz, 1H), 7.21-7.12 (m, 3H), 6.74 (d, J=15.6 Hz, 1H), 6.62-6.53 (m, 4H), 5.20 (s, 2H), 4.05 (s, 2H), 3.86 (s, 2H), 3.73 (t, J=5.4 Hz, 2H), 1.88-1.61 (m, 4H); $^{13}$C NMR (CD$_3$OD, 75 MHz) δ=183.57, 179.92, 173.95, 173.50, 167.98, 159.86, 143.15, 141.25, 140.74, 139.39, 134.80, 132.79, 132.19, 130.56, 130.35, 129.14, 128.88, 128.28, 128.21, 123.07, 114.46, 104.31, 55.35, 51.89, 44.41, 25.54, 24.94; HRESIMS m/z calcd for C$_{37}$H$_{33}$N$_4$O$_9$SNa [M]$^-$ 709.1975, found 709.1956.

Following general procedure VIII gave 18% yield of product. $^1$H NMR (500 MHz, CD$_3$OD) δ 8.14 (s, 1H), 7.76 (d, J=8.2 Hz, 1H), 7.44 (d, J=15.1 Hz, 1H), 7.16 (d, J=8.3 Hz, 1H), 6.81 (d, J=16.7 Hz, 1H), 6.78-6.61 (m, 4H), 6.61-6.45 (m, 2H), 3.91-3.51 (m, 4H), 2.90 (t, J=8.0 Hz, 1H), 1.82-1.58 (m, 4H), 1.48-1.27 (m, 8H). HRESIMS m/z calcd for C$_{33}$H$_{32}$N$_3$O$_9$SNa [M]$^-$ 646.1864, found 646.1874.

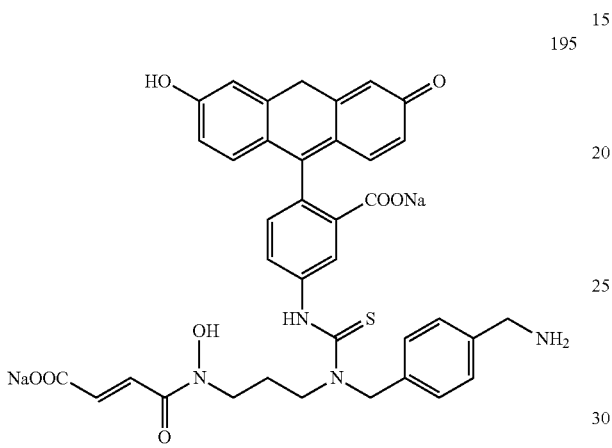

195

Following general procedure VIII gave 19% yield of product. $^1$H NMR (300 MHz, CD$_3$OD) δ 7.81 (s, 1H), 7.71-7.63 (m, 1H), 7.46-7.30 (m, 5H), 7.22-7.12 (m, 3H), 6.80 (d, J=15.6 Hz, 1H), 6.58-6.49 (m, 4H), 5.20 (s, 2H), 3.77 (s, 2H), 3.77 (d, J=6.6 Hz, 2H), 2.25-2.05 (m, 2H).

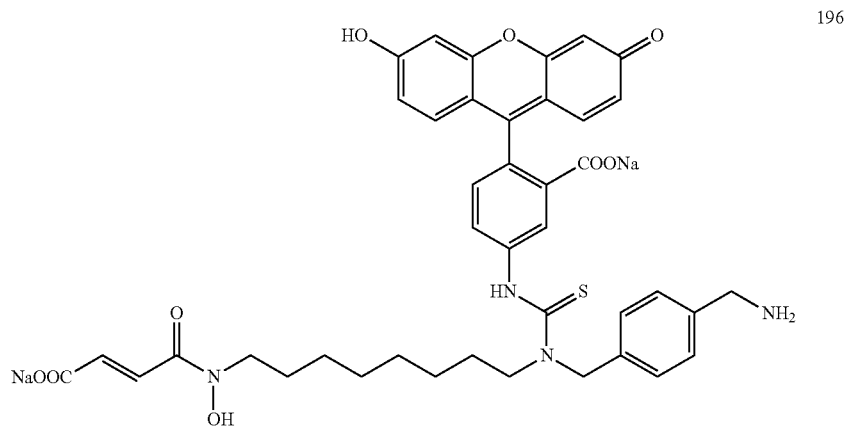

196

Following general procedure VIII gave 48% yield of product. $^1$H NMR (300 MHz, CD$_3$OD) δ 7.84-7.61 (m, 1H), 7.47 (s, 4H), 7.35 (d, J=17.4 Hz, 1H), 7.16 (dd, J=8.9, 4.1 Hz, 3H), 6.83 (d, J=15.6 Hz, 1H), 6.61 (d, J=7.7 Hz, 5H), 5.23 (s, 2H), 4.09 (s, 2H), 3.77 (t, 7.8 Hz, 2H), 3.68 (t, 6.6 Hz, 2H), 1.85-1.55 (m, 4H), 1.42-1.22 (m, 8H). HRESIMS m/z calcd for C$_{41}$H$_{41}$N$_4$O$_9$SNa [M]$^-$ 765.2599, found 765.2603.

197
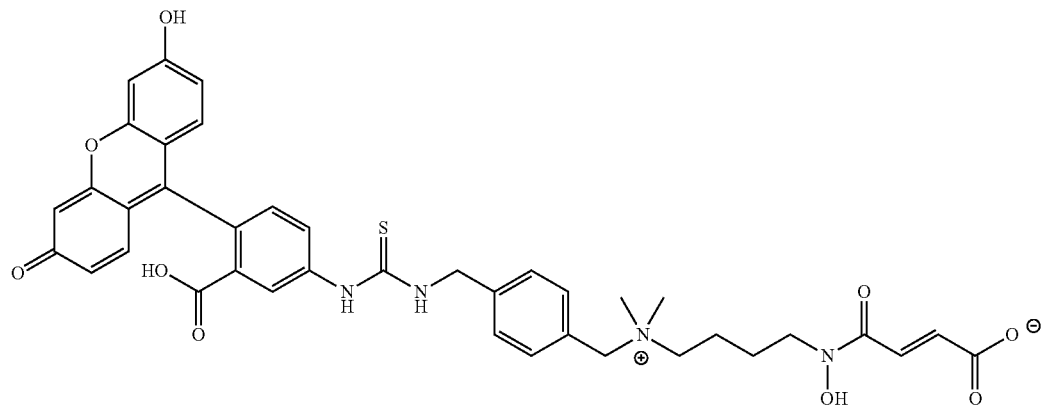
Following general procedure VIII gave 68% yield of product. ¹H NMR (300 MHz, CD₃OD) δ 7.82 (s, 1H), 7.54 (q, J=8.1 Hz, 5H), 7.42 (d, J=15.6 Hz, 1H), 7.22 (d, J=8.1 Hz, 1H), 7.14 (d, J=9.1 Hz, 2H), 6.84 (d, J=15.6 Hz, 1H), 6.62-6.44 (m, 5H), 4.97 (s, 2H), 4.48 (s, 2H), 3.79 (t, J=6.6 Hz, 2H), 2.99 (s, 6H), 2.00-1.81 (m, 2H), 1.83-1.66 (m, 2H). HRES-IMS m/z calcd for $C_{39}H_{37}N_4O_9SNa$ [M]⁻ 737.2286, found 737.2279.
198
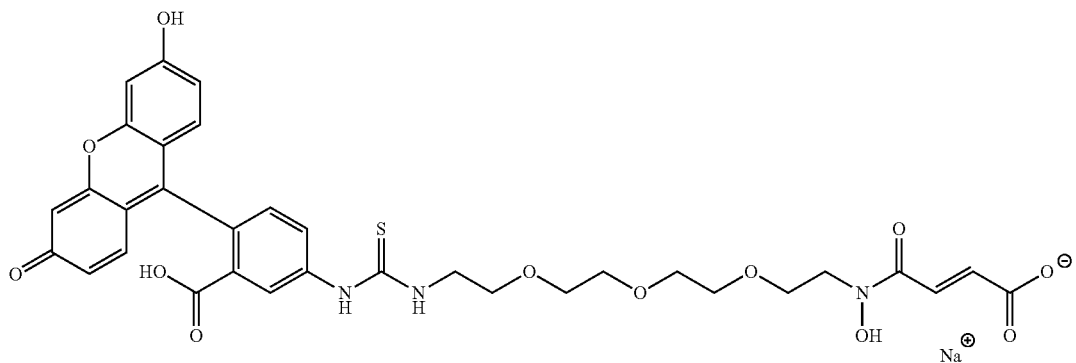
Following general procedure VIII gave 54% yield of product. ¹H NMR (300 MHz, CD₃OD) δ 8.02 (d, J=24.9 Hz, 1H), 7.80 (d, J=8.1 Hz, 1H), 7.37 (d, J=15.7 Hz, 1H), 7.19 (ddd, J=16.2, 10.6, 8.1 Hz, 4H), 6.85 (d, J=15.6 Hz, 1H), 6.67-6.59 (m, 5H), 3.90-3.79 (m, 5H), 3.71 (q, J=5.7 Hz, 4H), 3.66 (s, 4H), 3.62 (s, 4H). LC-Ms m/z calcd for $C_{33}H_{32}N_3O_{12}SNa$ [M+H₂]⁺ 695.2, found 695.2.
199
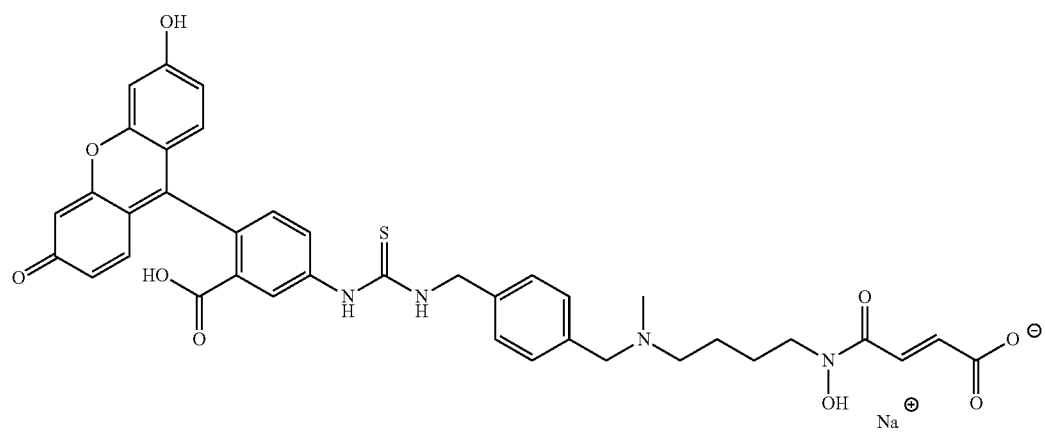

Following general procedure VIII gave 57% yield of product. $^1$H NMR (300 MHz, CD$_3$OD) δ 7.95 (s, 1H), 7.72 (d, J=7.9 Hz, 1H), 7.49-7.34 (m, 4H), 7.16 (dd, J=20.8, 8.6 Hz, 4H), 6.84 (d, J=15.5 Hz, 1H), 6.62 (d, J=9.4 Hz, 5H), 3.80 (s, 2H), 3.70 (t, 4.8 Hz, 2H), 2.70 (t, 6.0 Hz, 2H), 2.39 (s, 3H), 1.75-1.55 (m, 4H).

Determine the Dissociation Constants for Fluorophore 20 to JHDMs

To measure fluorescence polarization, a Perkin Elmer EnVision 2102 Multilabel plate reader equipped with FP-FITC optic module was used. Corning half-area, black, flat-bottom, polystyrene, 96-well plates (cat. #: 3993) were used for all FP studies. Auto-adjustment of focal height and gain was performed in the well containing 80 μL of 1 nM fluorophore 20, the recommended concentration of fluorescein for this plate reader.

Figure 8:
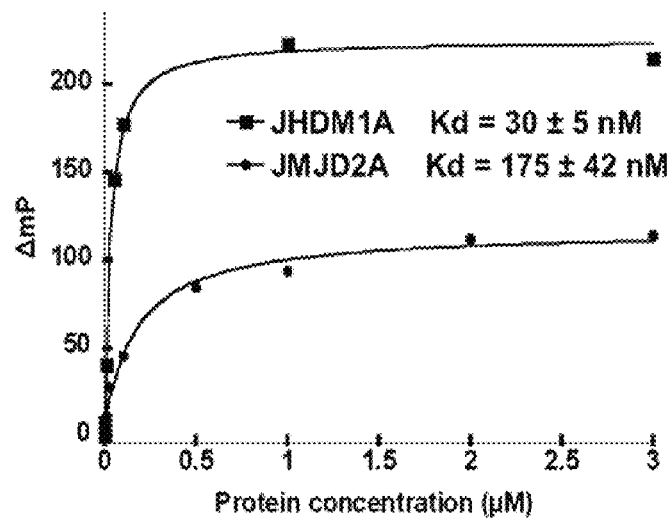
FIG. 8 is a graph of data that is used to determine the $K_d$ values for Compound 20 to JHDM1A and JMJD2A using FP assay.
Figure 10:
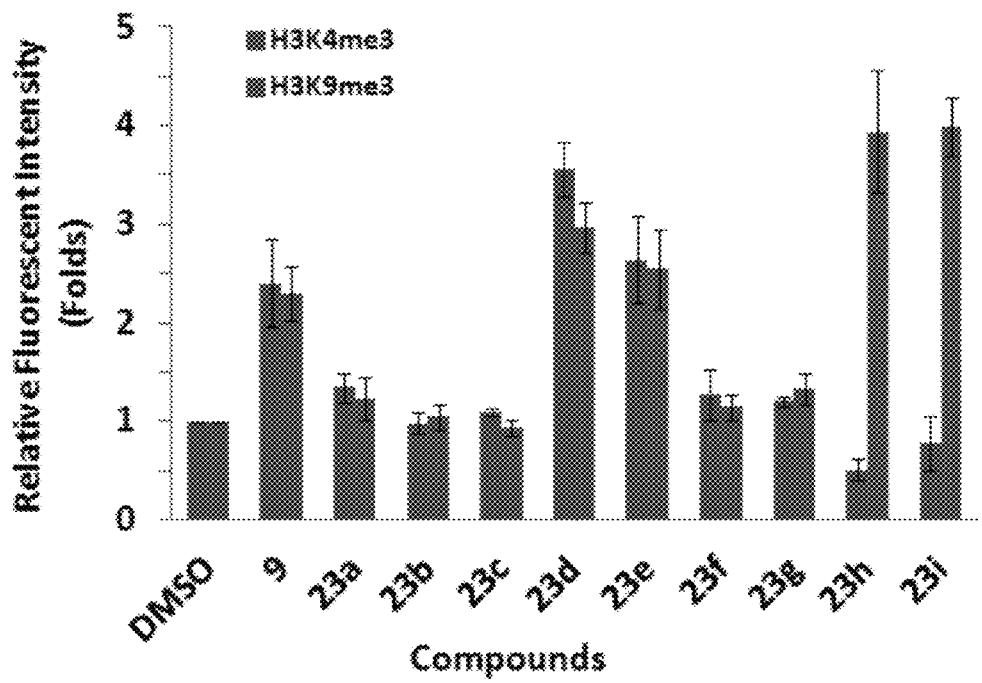
FIG. 10 is a bar graph representation of data for evaluation of the cellular activity of methylstat analogs (23a-i). KYSE150 cells were treated with DMSO or 2.5 µM of each compound for 48 h before immunostaining

The dissociation constant (Kd) for fluorophore 20 to GST-JMJD2A(1-420) was measured (See FIG. 8) by titrating 20 (1 nM) with purified JMJD2A using protocols reported by Rossi et al. in *Nat. Protoc.*, 2011, 6(3), 365-87. Fluorescence intensity values in parallel (i.e., $I_{\|}$) and perpendicular (i.e., $I\bot$) planes for each well were measured after 2 h of incubation at room temperature. For each experimental measurement, the protein background was subtracted, and the polarization (P) was calculated using these corrected values of $I_{\|}$ and $I\bot$ from the equation: $P=(I_{\|}-G \cdot I\bot)/(I_{\|}+G \cdot I\bot)$, where the G factor is derived from the instrument auto-adjustment step. Kaleida-Graph (Synergy Software) was used to fit the binding curve, which provided the Kd for 20 and GST-JMJD2A(1-420) as 175±42 nM. The Kd for 20 and JHDM1A was determined as 30±5 nM in a similar fashion.

Improving the Activity of Methylstat.

A more active (EC$_{50}$<100 nM) cellular probe for JHDMs can be developed based on the present inventors success in the discovery of a selective cellular probe for JHDMs, methylstat, and a high-affinity analog 20. One approach is to systematically optimize the structure of methylstat by synthesizing and evaluating the biological activity of its analogs. One can achieve this in silico by using virtual docking to assist the inhibitor design in each optimization cycle and use the structure-activity relationships (SARs) data to refine the docking algorithm.

It should be noted that although fluorophore 20 appears to have high affinity for JHDMs, its corresponding ester, 21, did not significantly induce hypermethylation of H3K4me3 or H3K9me3 in cells. A fluorescence-based imaging study showed that 21 was excluded from the nuclei. These results indicate that in some instances biochemical studies alone are not sufficient for the development of highly active cellular probes for JHDMs. Therefore, in some instances the cell-based quantitative immunostaining assay is used as the primary assay to analyze the activities of synthesized inhibitors.

Synthesis and Evaluation of the Cellular Activity of Methylstat Analogs.

Figure 9:
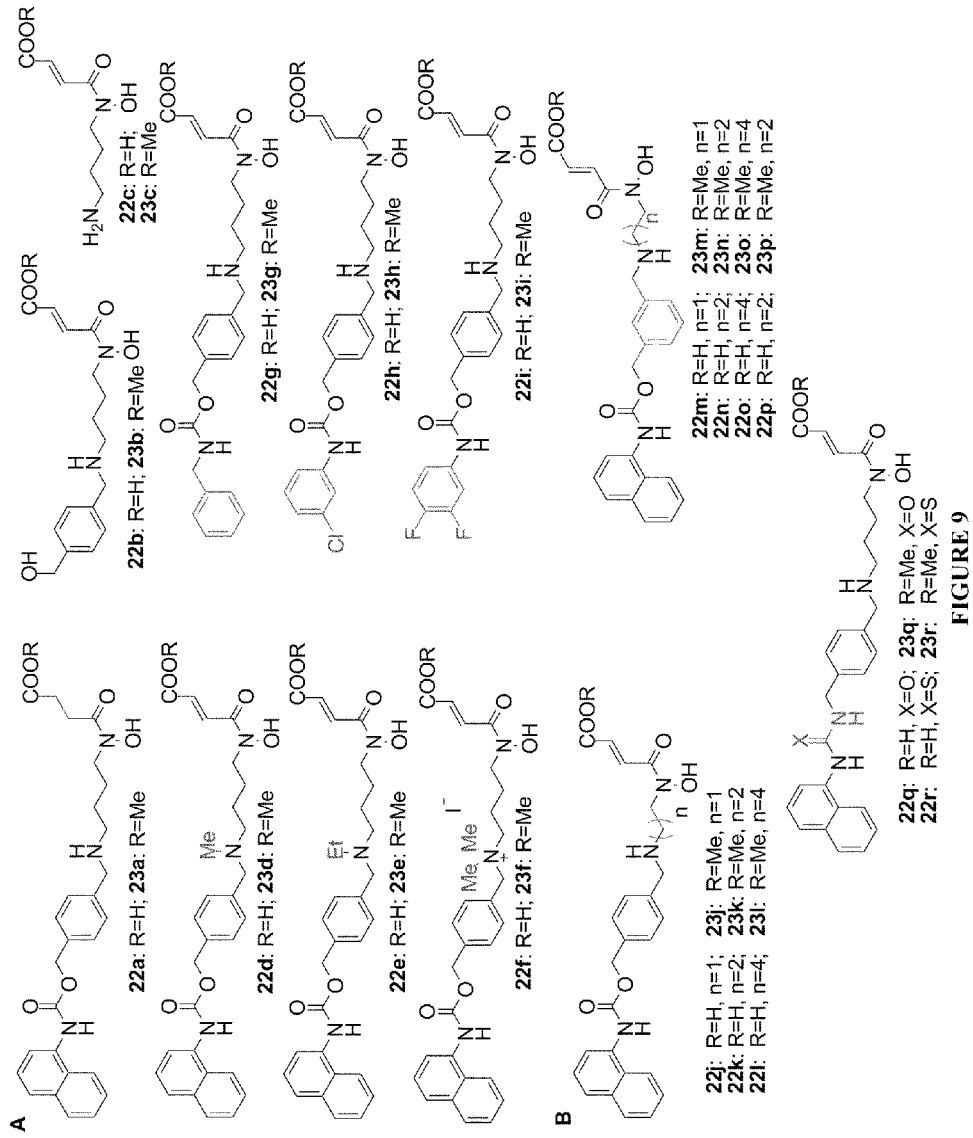
FIG. 9 shows chemical structures of methylstat analogs (23a-r) and their corresponding acids (22a-r) for SAR studies. Fragments in red are distinct from methylstat.

To develop a more active cellular probe for JHDMs, the structure-activity relationships (SARs) of methylstat was studied. See FIG. 9. Several analogs, 23a-i (See compound structure above), were synthesized using synthetic processes described herein. Cellular effects of these compounds were evaluated using H3K4me3- and H3K9me3-immunostaining assays. As shown in the bar graph below, the results indicate that compound 23a, which contains a more flexible αKG mimic, and truncated analogs of methylstat (i.e., 23b and 23c) showed significantly decreased cellular activity; the naphthalene ring of methylstat can be replaced by another aromatic group (i.e., 23h and 23i) but not an alkyl group (i.e., 23g); the amine functional group can be either a secondary or a tertiary amine (i.e., 23d, 23e, 23h, and 23i), but further alkylation of 23d to the ammonium salt 23f reduced its activity.

To further study SAR for methylstat, additional analogs, 23j-p are synthesized to evaluate the cellular activities. Some of these analogs vary the linker lengths (i.e., 23j-l) while others vary the hydrophobic region of the lysine-mimicking fragment (i.e., 23m-p). Because compound 20 showed significantly higher affinity to JHDMs, the carbamate group is changed to a urea (i.e., 23q) or a thiourea (i.e., 23r) to evaluate these functional groups on cellular activity. These compounds are evaluated in the quantitative immunostaining assays. In addition, corresponding acids 22a-r are synthesized and are tested for the JMJD2A enzyme inhibition.

Develop a More Active JHDM Cellular Probe

Figure 11:
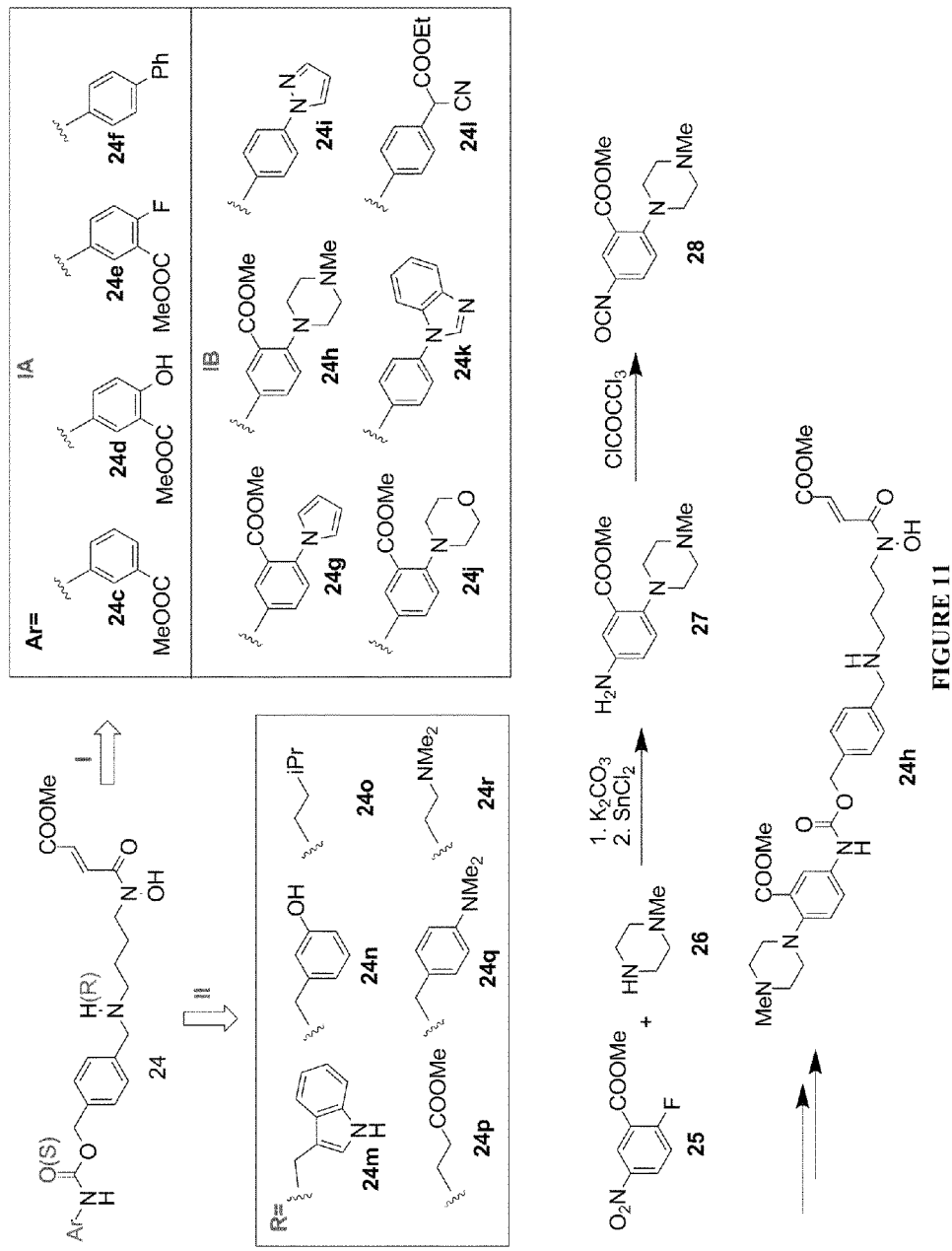
FIG. 11 shows some of the representative chemical structure of JHDM inhibitors of the present invention and synthetic scheme for producing compounds in Series 1B.

Based on SAR data, two new series of bivalent JHDM inhibitors 24 are designed. Series 1 compounds replace the naphthalene group of methylstat with other aromatic groups. Compounds in series 1A can be synthesized using commercially available isocyanates or isothiocyantes in the similar fashion as methylstat described herein (see FIG. 11, top). The corresponding isocyanates or isothiocyanates for compounds in series 1B are not commercially available, but can be synthesized in 3 steps using commercial materials, as shown in FIG. 11 bottom. For example, synthesis of 24h can begin with an aromatic nucleophilic substitution reaction using a fluorobenzene derivative, 25, and amine 26 under strong basic conditions followed by reduction of the nitro group. Treatment of the resulting aniline 27 with trichloromethyl chloromethylformate produces isocyanate 28, and the corresponding isothiocyanate can be prepared by reacting 27 with thiocarbonylbisimidazole. These isocyanates or isothiocyanates can then be converted to methylstat analogs using procedures described herein.

Compounds in series 2 each have an additional substitution on the amine nitrogen. They can be prepared by reductive amination reactions using methylstat and the corresponding commercially available aldehydes. Alternatively, they can also be synthesized by direct alkylations of methylstat with the corresponding alkyl halides under basic conditions.

Figure 12:
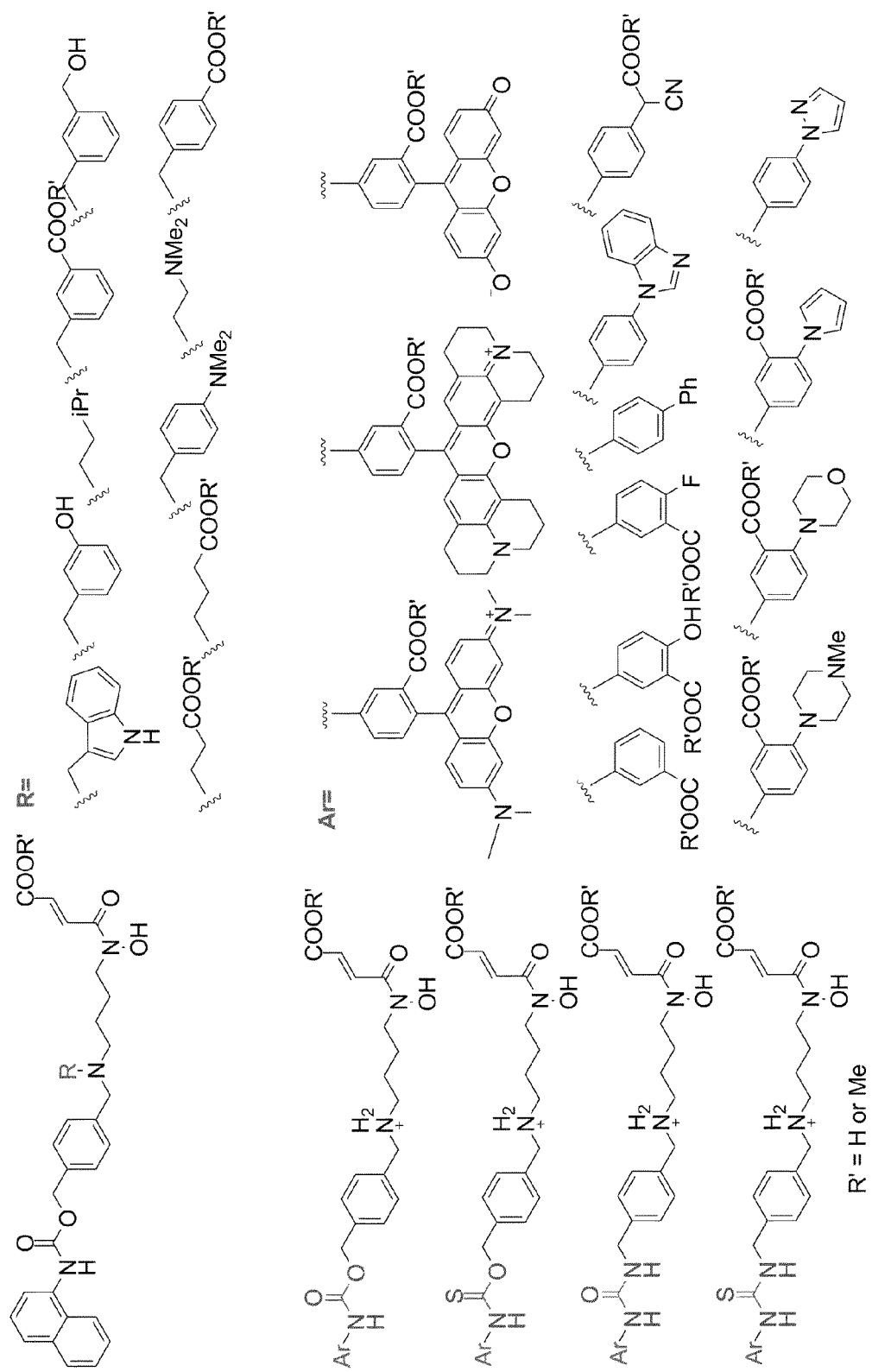
FIG. 12 shows some of the additional representative compounds believed to have potentially improved activity and specificity for JHDM inhibition activity.

FIG. 12 shows some of the additional compounds believed to have potentially improved activity and specificity for JHDM inhibition activity.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A compound of the formula: M-L-K, wherein M is a methyllysine mimic, L is a linker, and K is an α-ketoglutarate mimic, wherein the methyllysine mimic is of the formula:

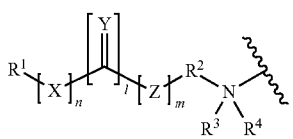

wherein
- each of l, m and n is independently 0 or 1;
- each of X and Z is independently O, S, or $NR^5$;
- Y is O, S or $NR^5$;
- $R^1$ is aryl, aralkyl, heteroaryl or fluorescein;
- $R^2$ is alkylene or a moiety of the formula $—R^6—Ar^1—R^7—$, wherein each of $R^6$ and $R^7$ is independently alkylene, and $Ar^1$ is arylene;
- $R^3$ is hydrogen, alkyl, aralkyl, heteroalkyl or heteroaralkyl;
- $R^4$ is hydrogen, alkyl, or absent; and
- each of $R^5$ is independently hydrogen or alkyl.

2. The compound according to claim 1, wherein $R^1$ is phenyl, naphthyl, benzyl, or naphthylalkyl, each of which is optionally substituted, or fluorescein.

3. The compound according to claim 1, wherein X is NH.

4. The compound according to claim 1, wherein Y is O.

5. The compound according to claim 1, wherein Z is O.

6. The compound according to claim 1, wherein $R^2$ is $C_3$-$C_8$ alkylene.

7. The compound according to claim 1, wherein $R^6$ and $R^7$ are methylene.

8. The compound according to claim 1, wherein $Ar^1$ is phenylene.

9. The compound according to claim 1, wherein $R^3$ is H or methyl.

10. The compound according to claim 1, wherein $R^4$ is alkyl or absent.

11. The compound according to claim 1, wherein the α-ketoglutarate mimic is of the formula:

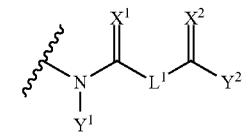

wherein
- $Y^1$ is $OR^8$, or $—NHR^8$;
- each of $X^1$ and $X^2$ is independently O, S, or $NR^9$;
- $Y^2$ is $—OR^8$, $—SR^{10}$, or $—NR^{11}R^{12}$;
- each of $R^8$ is independently hydrogen, alkyl, or a hydroxyl protecting group;
- each of $R^9$ is independently hydrogen, alkyl, or a nitrogen protecting group;
- $R^{10}$ is hydrogen, alkyl, or a sulfur protecting group;
- $R^{11}$ is hydrogen or alkyl;
- $R^{12}$ is hydrogen, alkyl, or a nitrogen protecting group; and
- $L^1$ is alkylene, alkenylene, arene, or alkynylene.

12. The compound according to claim 11, wherein $R^8$ is hydrogen or $C_1$-$C_4$ alkyl.

13. The compound according to claim 11, wherein $X^1$ and $X^2$ are O.

14. The compound according to claim 11, wherein $Y^2$ is $—OR^8$.

15. The compound according to claim 11, wherein $L^1$ is $C_2$-$C_6$ alkylene or $C_2$-$C_6$ alkenylene.

16. A composition comprising a compound of claim 1 and a pharmaceutically acceptable excipient.

* * * * *